(12) United States Patent
Faries, Jr. et al.

(10) Patent No.: US 7,307,245 B2
(45) Date of Patent: Dec. 11, 2007

(54) MEDICAL ITEM THERMAL TREATMENT SYSTEMS AND METHOD OF MONITORING MEDICAL ITEMS FOR COMPLIANCE WITH PRESCRIBED REQUIREMENTS

(75) Inventors: Durward I. Faries, Jr., Las Vegas, NV (US); Bruce R. Heymann, Vienna, VA (US); Calvin Blankenship, Frostburg, MD (US); David Hendrix, Ashburn, VA (US)

(73) Assignee: Patented Medical Solutions, LLC, Las Vegas, NV (US)

( * ) Notice: Subject to any disclaimer, the term of this patent is extended or adjusted under 35 U.S.C. 154(b) by 0 days.

(21) Appl. No.: 11/490,205

(22) Filed: Jul. 21, 2006

(65) Prior Publication Data

US 2007/0015975 A1  Jan. 18, 2007

Related U.S. Application Data

(60) Continuation of application No. 11/332,859, filed on Jan. 17, 2006, which is a continuation of application No. 10/805,487, filed on Mar. 22, 2004, now Pat. No. 7,041,941, which is a continuation-in-part of application No. 09/982,832, filed on Oct. 23, 2001, now Pat. No. 6,722,782, which is a division of application No. 09/539,183, filed on Mar. 30, 2000, now Pat. No. 6,467,953, said application No. 10/805,487 is a continuation-in-part of application No. 10/076,112, filed on Feb. 15, 2002, now Pat. No. 6,768,085, said application No. 10/805,487 is a continuation-in-part of application No. 10/695,487, filed on Oct. 29, 2003, which is a continuation of application No. 10/127,675, filed on Apr. 23, 2002, now Pat. No. 6,660,974, which is a continuation-in-part of application No. 09/413,532, filed on Apr. 7, 1998, now Pat. No. 6,294,762, which is a continuation-in-part of application No. PCT/US98/06951, filed on Apr. 7, 1998.

(60) Provisional application No. 60/042,737, filed on Apr. 7, 1997, provisional application No. 60/126,874, filed on Mar. 30, 1999, provisional application No. 60/301,829, filed on Jul. 2, 2001, provisional application No. 60/456,394, filed on Mar. 21, 2003, provisional application No. 60/456,398, filed on Mar. 21, 2003, provisional application No. 60/467,582, filed on May 5, 2003, provisional application No. 60/472,554, filed on May 23, 2003, provisional application No. 60/486,216, filed on Jul. 11, 2003.

(51) Int. Cl.
*H05B 1/02* (2006.01)
*F27B 17/00* (2006.01)
*G05B 11/30* (2006.01)

(52) U.S. Cl. ................. 219/413; 219/385; 219/413; 219/509; 237/2 A; 702/177; 165/254

(58) Field of Classification Search .............. None
See application file for complete search history.

(56) References Cited

U.S. PATENT DOCUMENTS

| | | | |
|---|---|---|---|
| 522,866 A | 7/1894 | Weinhagen et al. |
| 558,979 A | 4/1896 | Noble |
| 675,647 A | 6/1901 | Andersen et al. |
| 785,524 A | 3/1905 | Shea |
| 803,352 A | 10/1905 | Meyer |
| 1,062,111 A | 5/1913 | Nylander |
| 1,092,643 A | 4/1914 | Goolsby |
| 1,110,919 A | 9/1914 | Gamble |
| 1,223,274 A | 4/1917 | Hallock |
| 1,390,500 A | 9/1921 | Christian |
| 1,493,450 A | 5/1924 | Richardson |
| 1,659,719 A | 2/1928 | Blake |
| 1,726,212 A | 8/1929 | Bucky |
| 1,770,832 A | 7/1930 | Bass |
| 1,794,215 A | 2/1931 | Titus |
| 1,838,026 A | 12/1931 | Williams |
| 1,847,573 A | 3/1932 | Rupp |
| 1,847,954 A | 3/1932 | Fisher |
| 1,960,417 A | 5/1934 | Pain, Jr. |
| 1,982,213 A | 11/1934 | Hopkins |

| | | | | | | |
|---|---|---|---|---|---|---|
| 1,987,119 A | 1/1935 | Long | | 4,464,563 A | 8/1984 | Jewett |
| 1,995,302 A | 3/1935 | Goldstein | | 4,468,137 A | 8/1984 | Hilsum et al. |
| 2,063,902 A | 12/1936 | Beasley | | 4,476,877 A | 10/1984 | Barker |
| 2,087,586 A | 7/1937 | Tishman | | 4,481,410 A | 11/1984 | Bortnick |
| 2,124,293 A | 7/1938 | Goldstein | | 4,490,884 A | 1/1985 | Vickers |
| 2,175,099 A | 10/1939 | Abbott | | 4,495,402 A | 1/1985 | Burdick et al. |
| 2,204,764 A | 6/1940 | Mayo | | 4,509,532 A | 4/1985 | DeVries |
| 2,214,215 A | 9/1940 | Watermann et al. | | 4,523,078 A | 6/1985 | Lehmann |
| 2,254,994 A | 9/1941 | Butland | | 4,531,941 A | 7/1985 | Zasuwa |
| 2,470,481 A | 5/1949 | Freeman | | 4,532,414 A | 7/1985 | Shah et al. |
| 2,576,874 A | 11/1951 | Acton | | 4,551,136 A | 11/1985 | Mandl |
| 2,713,112 A | 7/1955 | Mills et al. | | 4,585,441 A | 4/1986 | Archibald |
| 2,741,099 A | 4/1956 | Beane | | 4,605,840 A | 8/1986 | Koopman |
| 2,766,907 A | 10/1956 | Wallace, Jr. | | 4,613,327 A | 9/1986 | Tegrarian et al. |
| 2,841,132 A | 7/1958 | Philipp | | 4,614,514 A | 9/1986 | Carr et al. |
| 2,885,526 A | 5/1959 | Paulding | | 4,626,243 A | 12/1986 | Singh et al. |
| 2,910,981 A | 11/1959 | Wilson et al. | | 4,628,186 A | 12/1986 | Bergemann et al. |
| 2,994,760 A | 8/1961 | Pecoraro et al. | | 4,647,756 A | 3/1987 | Willis |
| 3,051,582 A | 8/1962 | Muckler et al. | | 4,651,813 A | 3/1987 | Witt et al. |
| 3,140,716 A | 7/1964 | Harrison et al. | | 4,657,004 A | 4/1987 | Coffey |
| 3,193,339 A | 7/1965 | Cooper | | 4,678,460 A | 7/1987 | Rosner |
| 3,241,603 A | 3/1966 | Nagata | | 4,680,445 A | 7/1987 | Ogawa |
| 3,247,851 A | 4/1966 | Seibert | | 4,682,979 A | 7/1987 | Girouard |
| 3,255,812 A | 6/1966 | Bayane et al. | | 4,684,367 A | 8/1987 | Schaffer et al. |
| 3,329,202 A | 7/1967 | Birman | | 4,705,505 A | 11/1987 | Fried |
| 3,353,589 A | 11/1967 | Tope et al. | | 4,707,587 A | 11/1987 | Greenblatt |
| 3,370,153 A | 2/1968 | Du Fresne et al. | | 4,709,135 A | 11/1987 | Dietrich et al. |
| 3,386,498 A | 6/1968 | Funfstuck | | 4,726,193 A | 2/1988 | Burke et al. |
| 3,475,590 A | 10/1969 | Pins | | 4,735,609 A | 4/1988 | Comeau et al. |
| 3,485,245 A | 12/1969 | Lahr et al. | | 4,745,248 A | 5/1988 | Hayes |
| 3,536,132 A | 10/1970 | Pecoraro et al. | | 4,747,450 A | 5/1988 | Ikegame et al. |
| 3,551,641 A | 12/1970 | Truhan | | 4,747,826 A | 5/1988 | Sassano |
| 3,590,215 A | 6/1971 | Anderson et al. | | 4,756,299 A | 7/1988 | Podella |
| 3,612,059 A | 10/1971 | Ersek | | 4,759,749 A | 7/1988 | Verkaart |
| 3,612,165 A | 10/1971 | Haynes | | 4,772,778 A | 9/1988 | Ogawa |
| 3,614,385 A | 10/1971 | Horstman | | 4,781,548 A | 11/1988 | Alderson et al. |
| 3,629,552 A | 12/1971 | Edging | | 4,782,212 A | 11/1988 | Bakke |
| 3,640,277 A | 2/1972 | Adelberg | | 4,801,777 A | 1/1989 | Auerbach |
| 3,651,695 A | 3/1972 | Brown | | 4,804,367 A | 2/1989 | Smith et al. |
| 3,704,625 A | 12/1972 | Seto et al. | | 4,808,159 A | 2/1989 | Wilson |
| 3,713,302 A | 1/1973 | Reviel | | 4,814,570 A | 3/1989 | Takizaki |
| 3,777,187 A | 12/1973 | Kohn | | 4,823,554 A | 4/1989 | Trachtenberg et al. |
| 3,826,305 A | 7/1974 | Fishman | | 4,832,689 A | 5/1989 | Mauerer et al. |
| 3,858,106 A | 12/1974 | Launius | | 4,844,074 A | 7/1989 | Kurucz |
| 3,861,213 A | 1/1975 | Parker | | 4,847,470 A | 7/1989 | Bakke |
| 3,864,976 A | 2/1975 | Parker | | 4,859,360 A | 8/1989 | Suzuki et al. |
| 3,879,171 A | 4/1975 | Tulis | | 4,874,033 A | 10/1989 | Chatelain et al. |
| 3,895,741 A | 7/1975 | Nugent | | 4,874,359 A | 10/1989 | White et al. |
| 3,908,652 A | 9/1975 | Weissinger | | 4,878,537 A | 11/1989 | Verkaart |
| 3,940,742 A | 2/1976 | Hudspeth et al. | | 4,878,588 A | 11/1989 | Ephraim |
| 4,024,377 A | 5/1977 | Henke | | 4,883,117 A | 11/1989 | Dobbs et al. |
| 4,038,519 A | 7/1977 | Foucras | | 4,894,207 A | 1/1990 | Archer et al. |
| 4,084,080 A | 4/1978 | McMahan | | 4,900,308 A | 2/1990 | Verkaart |
| 4,090,514 A | 5/1978 | Hinck et al. | | 4,906,816 A | 3/1990 | Van Leerdam |
| 4,098,123 A | 7/1978 | Granzow, Jr. | | 4,910,386 A | 3/1990 | Johnson |
| 4,167,663 A | 9/1979 | Granzow, Jr. et al. | | 4,916,386 A | 4/1990 | Schulz |
| 4,189,995 A | 2/1980 | Lohr et al. | | 4,923,681 A | 5/1990 | Cox et al. |
| 4,233,495 A | 11/1980 | Scoville et al. | | 4,934,336 A | 6/1990 | White |
| 4,293,762 A | 10/1981 | Ogawa | | 4,935,604 A | 6/1990 | Allen et al. |
| 4,309,592 A | 1/1982 | Le Boeuf | | 4,961,320 A | 10/1990 | Gutmann |
| 4,318,276 A | 3/1982 | Sato et al. | | 4,994,021 A | 2/1991 | Smith et al. |
| 4,328,676 A | 5/1982 | Reed | | 5,013,889 A | 5/1991 | Bakke |
| 4,331,859 A | 5/1982 | Thomas et al. | | 5,019,047 A | 5/1991 | Kriesel |
| 4,336,435 A | 6/1982 | Kashyap et al. | | 5,042,455 A | 8/1991 | Yue et al. |
| 4,356,383 A | 10/1982 | Dahlberg | | 5,059,182 A | 10/1991 | Laing |
| 4,364,234 A | 12/1982 | Reed | | 5,061,241 A | 10/1991 | Stephens, Jr. et al. |
| 4,375,813 A | 3/1983 | Hessel | | 5,061,630 A | 10/1991 | Knopf et al. |
| 4,384,578 A | 5/1983 | Winkler | | 5,063,994 A | 11/1991 | Verkaart |
| 4,407,133 A | 10/1983 | Edmonson | | 5,073,167 A | 12/1991 | Carr et al. |
| 4,419,568 A | 12/1983 | VanOverloop | | 5,075,167 A | 12/1991 | Yamauchi et al. |
| 4,430,078 A | 2/1984 | Sprague | | 5,081,697 A | 1/1992 | Manella |
| 4,448,204 A | 5/1984 | Lichtenstein | | 5,096,822 A | 3/1992 | Rosenkrans, Jr. et al. |
| 4,455,478 A | 6/1984 | Guibert | | 5,097,898 A | 3/1992 | Verkaart |

| | | | | | | |
|---|---|---|---|---|---|---|
| 5,106,373 A | 4/1992 | Augustine et al. | | 5,538,399 A | 7/1996 | Johnson |
| 5,108,372 A | 4/1992 | Swenson | | 5,540,561 A | 7/1996 | Johnson |
| 5,125,069 A | 6/1992 | O'Boyle | | 5,540,901 A | 7/1996 | Riley |
| 5,125,900 A | 6/1992 | Teves | | 5,564,915 A | 10/1996 | Johnson |
| 5,129,033 A | 7/1992 | Ferrara et al. | | 5,567,119 A | 10/1996 | Johnson |
| 5,153,827 A | 10/1992 | Coutre et al. | | 5,567,136 A | 10/1996 | Johnson |
| 5,169,389 A | 12/1992 | Kriesel | | 5,572,873 A | 11/1996 | Lavigne et al. |
| 5,172,347 A | 12/1992 | Masuda | | 5,575,563 A | 11/1996 | Chiu et al. |
| 5,180,896 A | 1/1993 | Gibby et al. | | 5,584,811 A | 12/1996 | Ross et al. |
| 5,183,994 A | 2/1993 | Bowles, Sr. et al. | | RE35,501 E | 5/1997 | Ross et al. |
| 5,184,613 A | 2/1993 | Mintz | | 5,634,426 A | 6/1997 | Tomlinson et al. |
| 5,195,976 A | 3/1993 | Swenson | | 5,647,854 A | 7/1997 | Olsen et al. |
| 5,205,820 A | 4/1993 | Kriesel | | 5,649,910 A | 7/1997 | Kriesel et al. |
| 5,211,631 A | 5/1993 | Sheaff | | 5,653,905 A | 8/1997 | McKinney |
| 5,217,064 A | 6/1993 | Kellow et al. | | 5,658,250 A | 8/1997 | Blomquist et al. |
| 5,232,439 A | 8/1993 | Campbell et al. | | 5,658,252 A | 8/1997 | Johnson |
| 5,241,951 A | 9/1993 | Mason et al. | | 5,658,478 A | 8/1997 | Roeschel et al. |
| 5,243,172 A | 9/1993 | Hazan et al. | | 5,661,978 A | 9/1997 | Holmes et al. |
| 5,243,833 A | 9/1993 | Coelho et al. | | 5,669,877 A | 9/1997 | Blomquist |
| 5,245,693 A | 9/1993 | Ford et al. | | 5,681,284 A | 10/1997 | Herskowitz |
| 5,250,032 A | 10/1993 | Carter, Jr. et al. | | 5,683,381 A | 11/1997 | Carr et al. |
| 5,254,094 A | 10/1993 | Starkey et al. | | 5,690,614 A | 11/1997 | Carr et al. |
| 5,261,411 A | 11/1993 | Hughes | | 5,695,473 A | 12/1997 | Olsen |
| 5,261,875 A | 11/1993 | Spears et al. | | 5,707,431 A | 1/1998 | Verkaart et al. |
| 5,263,323 A | 11/1993 | Maus et al. | | 5,713,864 A | 2/1998 | Verkaart |
| 5,263,929 A | 11/1993 | Falcone et al. | | 5,720,728 A | 2/1998 | Ford |
| 5,276,310 A | 1/1994 | Schmidt et al. | | 5,729,653 A | 3/1998 | Magliochetti et al. |
| 5,279,558 A | 1/1994 | Kriesel | | 5,733,263 A | 3/1998 | Wheatman |
| 5,279,598 A | 1/1994 | Sheaff | | 5,738,442 A | 4/1998 | Paron et al. |
| 5,282,264 A | 1/1994 | Reeves et al. | | 5,743,878 A | 4/1998 | Ross et al. |
| 5,282,683 A | 2/1994 | Brett | | 5,755,275 A | 5/1998 | Rose et al. |
| 5,290,230 A | 3/1994 | Ainsworth et al. | | 5,772,409 A | 6/1998 | Johnson |
| 5,296,684 A | 3/1994 | Essig et al. | | 5,779,364 A | 7/1998 | Cannelongo et al. |
| 5,297,234 A | 3/1994 | Harms et al. | | 5,786,568 A | 7/1998 | McKinney |
| 5,308,335 A | 5/1994 | Ross et al. | | 5,788,669 A | 8/1998 | Peterson |
| 5,315,830 A | 5/1994 | Doke et al. | | 5,788,671 A | 8/1998 | Johnson |
| 5,318,540 A | 6/1994 | Athayde et al. | | 5,806,528 A | 9/1998 | Magliochetti |
| 5,330,431 A | 7/1994 | Herskowitz | | 5,807,332 A | 9/1998 | Augustine et al. |
| 5,333,326 A | 8/1994 | Faries, Jr. et al. | | 5,810,771 A | 9/1998 | Blomquist |
| 5,338,157 A | 8/1994 | Blomquist | | 5,817,146 A | 10/1998 | Augustine |
| 5,342,313 A | 8/1994 | Campbell et al. | | 5,823,746 A | 10/1998 | Johnson |
| 5,345,923 A | 9/1994 | Luebke et al. | | 5,824,000 A | 10/1998 | Pavlo et al. |
| 5,348,539 A | 9/1994 | Herskowitz | | 5,840,068 A | 11/1998 | Cartledge |
| 5,364,371 A | 11/1994 | Kamen | | 5,858,303 A | 1/1999 | Schiffmann et al. |
| 5,364,385 A | 11/1994 | Harms et al. | | 5,868,195 A | 2/1999 | Westbrooks, Jr. |
| 5,370,674 A | 12/1994 | Farrell | | 5,868,250 A | 2/1999 | Brackett |
| 5,381,510 A | 1/1995 | Ford et al. | | 5,875,282 A | 2/1999 | Jordan et al. |
| 5,389,078 A | 2/1995 | Zalesky et al. | | 5,876,370 A | 3/1999 | Blomquist |
| 5,397,875 A | 3/1995 | Bechtold, Jr. | | 5,879,143 A | 3/1999 | Cote et al. |
| 5,399,007 A | 3/1995 | Marconet | | 5,879,329 A | 3/1999 | Ginsburg |
| 5,399,166 A | 3/1995 | Laing | | 5,891,096 A | 4/1999 | Hyun et al. |
| 5,408,576 A | 4/1995 | Bishop | | 5,893,843 A | 4/1999 | Rodrigues |
| 5,408,577 A | 4/1995 | Weber, Jr. et al. | | 5,897,207 A | 4/1999 | Hartmann |
| 5,411,480 A | 5/1995 | Kriesel | | 5,910,210 A | 6/1999 | Violi et al. |
| 5,411,482 A | 5/1995 | Campbell | | 5,919,218 A | 7/1999 | Carr |
| 5,415,282 A | 5/1995 | Kienholz | | 5,924,289 A | 7/1999 | Bishop, II |
| 5,417,274 A | 5/1995 | Verkaart | | 5,928,196 A | 7/1999 | Johnson et al. |
| 5,420,962 A | 5/1995 | Bakke | | 5,935,099 A | 8/1999 | Peterson et al. |
| 5,423,759 A | 6/1995 | Campbell | | 5,935,106 A | 8/1999 | Olsen |
| 5,424,512 A | 6/1995 | Turetta et al. | | 5,954,485 A | 9/1999 | Johnson et al. |
| 5,433,704 A | 7/1995 | Ross et al. | | 5,954,700 A | 9/1999 | Kovelman |
| 5,451,209 A | 9/1995 | Ainsworth et al. | | 5,961,492 A | 10/1999 | Kriesel et al. |
| 5,474,538 A | 12/1995 | Stihler et al. | | 5,961,700 A | 10/1999 | Oliver |
| 5,482,373 A | 1/1996 | Hutchinson | | 5,977,520 A | 11/1999 | Madson, Jr. et al. |
| 5,483,799 A | 1/1996 | Dalto | | 5,986,239 A | 11/1999 | Corrigan, III et al. |
| 5,485,408 A | 1/1996 | Blomquist | | 5,989,238 A | 11/1999 | Ginsburg |
| 5,492,534 A | 2/1996 | Athayde et al. | | 6,024,539 A | 2/2000 | Blomquist |
| 5,512,043 A | 4/1996 | Verkaart | | 6,035,102 A | 3/2000 | Bakke |
| 5,514,095 A | 5/1996 | Brightbill et al. | | 6,039,926 A | 3/2000 | Goldman |
| 5,523,055 A | 6/1996 | Hansen et al. | | 6,045,648 A | 4/2000 | Palmgren et al. |
| 5,524,643 A | 6/1996 | Faries, Jr. et al. | | 6,061,303 A | 5/2000 | Gauthier et al. |
| 5,531,697 A | 7/1996 | Olsen et al. | | 6,062,429 A | 5/2000 | West et al. |
| 5,531,698 A | 7/1996 | Olsen | | 6,096,007 A | 8/2000 | Haan et al. |

| | | |
|---|---|---|
| 6,102,044 A | 8/2000 | Naidyhorski |
| 6,117,122 A | 9/2000 | Din et al. |
| 6,124,572 A | 9/2000 | Spilger et al. |
| 6,129,702 A | 10/2000 | Woias et al. |
| 6,139,528 A | 10/2000 | Kistner et al. |
| 6,142,974 A | 11/2000 | Kistner et al. |
| 6,146,359 A | 11/2000 | Carr et al. |
| 6,174,300 B1 | 1/2001 | Kriesel et al. |
| 6,175,099 B1 | 1/2001 | Shei et al. |
| 6,175,688 B1 | 1/2001 | Cassidy et al. |
| 6,221,045 B1 | 4/2001 | Duchon et al. |
| 6,221,051 B1 * | 4/2001 | Hjertman et al. ........... 604/189 |
| 6,248,077 B1 | 6/2001 | Elson et al. |
| 6,254,572 B1 | 7/2001 | Knifper et al. |
| 6,257,759 B1 | 7/2001 | Witonsky et al. |
| 6,259,067 B1 | 7/2001 | Faries, Jr. et al. |
| 6,261,261 B1 | 7/2001 | Gordon |
| 6,264,049 B1 | 7/2001 | Shteynberg |
| 6,294,111 B1 | 9/2001 | Shacklett, III et al. |
| 6,294,762 B1 | 9/2001 | Faries, Jr. et al. |
| 6,316,750 B1 | 11/2001 | Levin |
| 6,371,121 B1 | 4/2002 | Faries, Jr. et al. |
| 6,376,805 B2 | 4/2002 | Faries, Jr. et al. |
| 6,384,380 B1 | 5/2002 | Faries, Jr. et al. |
| 6,464,666 B1 | 10/2002 | Augustine et al. |
| 6,467,953 B1 | 10/2002 | Faries, Jr. et al. |
| 6,524,239 B1 * | 2/2003 | Reed et al. ................. 600/300 |
| 6,527,462 B2 | 3/2003 | Arledge et al. |
| 6,553,336 B1 * | 4/2003 | Johnson et al. ............ 702/188 |
| 6,566,631 B2 | 5/2003 | Faries, Jr. et al. |
| 6,660,974 B2 | 12/2003 | Faries, Jr. et al. |
| 6,722,782 B2 | 4/2004 | Faries, Jr. et al. |
| 6,736,788 B1 * | 5/2004 | Mongomery et al. ...... 604/4.01 |
| 6,740,059 B2 | 5/2004 | Flaherty |
| 6,748,164 B1 | 6/2004 | Kuzyk |
| 6,768,085 B2 | 7/2004 | Faries, Jr. et al. |
| 6,824,528 B1 | 11/2004 | Faries, Jr. et al. |
| 6,850,252 B1 * | 2/2005 | Hoffberg .................... 715/716 |
| 6,869,538 B2 * | 3/2005 | Yu et al. ..................... 604/113 |
| 7,031,602 B2 | 4/2006 | Faries, Jr. et al. |
| 7,031,778 B2 * | 4/2006 | Hsiung et al. ................ 700/29 |
| 7,041,941 B2 | 5/2006 | Faries, Jr. et al. |
| 7,090,658 B2 | 8/2006 | Faries, Jr. et al. |
| 7,176,030 B2 | 2/2007 | Faries, Jr. et al. |
| 2001/0009610 A1 | 7/2001 | Augustine et al. |
| 2002/0147426 A1 | 10/2002 | Faries, Jr. et al. |
| 2002/0156451 A1 | 10/2002 | Lenker |
| 2002/0158058 A1 | 10/2002 | Faries, Jr. et al. |
| 2002/0184906 A1 | 12/2002 | Faries, Jr. |
| 2003/0075183 A1 | 4/2003 | Faries, Jr. et al. |
| 2003/0114795 A1 | 6/2003 | Faries, Jr. et al. |
| 2003/0135388 A1 | 7/2003 | Martucci et al. |
| 2003/0172937 A1 | 9/2003 | Faries, Jr. et al. |
| 2003/0216831 A1 * | 11/2003 | Hart et al. .................. 700/235 |
| 2003/0222933 A1 | 12/2003 | Choi |
| 2004/0170409 A1 | 9/2004 | Faries, Jr. et al. |
| 2004/0189258 A1 | 9/2004 | Lehmann et al. |
| 2005/0222933 A1 * | 10/2005 | Wesby ......................... 705/36 |
| 2006/0065276 A1 | 3/2006 | Kammer et al. |
| 2006/0086361 A1 | 4/2006 | Kammer et al. |
| 2006/0091128 A1 | 5/2006 | Kammer et al. |

FOREIGN PATENT DOCUMENTS

| | | |
|---|---|---|
| DE | 37 42 927 A1 | 7/1989 |
| DE | 197 52 578 A1 | 6/1999 |
| EP | 0927552 A1 | 7/1999 |
| GB | 2029677 A | 3/1980 |
| NZ | 331678 A | 3/2000 |
| WO | WO 98/45658 | 10/1998 |
| WO | WO 99/22786 | 5/1999 |
| WO | WO 99/58127 | 11/1999 |

OTHER PUBLICATIONS

Health Devices, vol. 25, No. 10, Oct. 1996.
Minco Products, Inc., Bulletin CT198, 1996.
Eurotherm Controls, Inc., Model 2116 Temperature Controller, 1997.
Ellenwood, Drop Detector, IBM Technical Bulletin, vol. 12, No. 5, Oct. 1969.
Cbi Medical, Inc., IV Fluid Warmer Model 8362, 1992.
Cahill, New Name, New Helmsman, JEMS, Aug. 1996.
Koolatron, Canadian Company announces the release of a precision control unit, Aug. 1997.
CBi Healthcare Systems, Inc., *Controlled Temperature Cabinet System*, JEMS, Mar. 1997.
Koolatron, *P-34 PC-3 Precision Control Thermoelectric Cooler/Warmer*, Jan. 1998.
Anton, *500 miles from nowhere, it'll give you a cold drink or a warm burger. . .*, Technology Update, 1993.
Koolatron, *1997 U.S. $ Price List*, 1997.
Kellow et al., *Drug Adulteration In Prehospital Emergency Medical Services*, Oct. 1994.

\* cited by examiner

*Primary Examiner*—J. Pelham
(74) *Attorney, Agent, or Firm*—Edell, Shapiro & Finnan, LLC

(57) ABSTRACT

Various present invention devices enable adherence to requirements for medical items. A medical item of the present invention includes a monitoring or data recording device to monitor and/or record medical solution conditions. The device may further include indicators to indicate compliance of the medical solution with prescribed requirements (e.g., manufacturer, medical standard or regulation, etc.). The medical item may alternatively include a barcode or transponder to uniquely identify the medical item to a thermal treatment system measuring and storing conditions in a central database. The present invention further includes various thermal treatment systems that monitor medical items for prescribed requirements and display the monitored parameters to medical personnel. In addition, the present invention may place time stamp information on medical items to enable determination by medical personnel of compliance with prescribed requirements.

72 Claims, 35 Drawing Sheets

WARMING/COOLING SYSTEM REPORT

310 {
- BASED UPON DATA COLLECTED BY DATE/TIME: _____
- REPORT GENERATION DATE/TIME: _____
- OPERATING TECHNICIAN: _____
}

304 — PATIENT INFORMATION:
- PATIENT'S NAME: _____
- PATIENT'S ID#: _____
- BLOOD TYPE: _____

308 — FACILITY INFORMATION:
- FACILITY NAME: _____
- FACILITY LOCATION: _____
- DOCTOR'S INFORMATION: _____
- TYPE OF PROCEDURE: _____

302 — ITEM WARMING/COOLING DATA:
- TYPE OF ITEM/FLUID: _____
- INTENDED USE: _____
- START DATE: _____
- START TIME: _____
- DURATION: _____
- START TEMPERATURE: _____
- REMOVAL TEMPERATURE: _____
- FLUID FLOW PRESSURE (IF APPLICABLE): _____

306 — WARMING/COOLING SYSTEM INFO:
- SYSTEM ID: _____
- WARMING/COOLING CHAMBER ID (IF APPLICABLE): _____
- SERIAL NUMBER: _____
- MANUFACTURER'S NUMBER: _____
- LAST INSPECTED DATE: _____
- INSPECTED BY: _____
- NEXT INSPECTION DATE: _____

FIG.12A

```
           MM/DD/YY
           HH:MM
43.0° C   15:15
42.8° C   15:30
42.7° C   15:45
42.9° C   16:00
42.7° C   16:15
42.9° C   16:30
START TIME 15:15    END TIME 16:30
```
FIG.12B
```
                 MM/DD/YY
                 HH:MM
*43.0° C  15:15   *43.0° C  16:45
*42.8° C  15:30   *42.8° C  17:00
*42.7° C  15:45   *42.7° C  17:15
*42.9° C  16:00   *42.9° C  17:30
*42.7° C  16:15   *42.7° C  17:45
*42.9° C  16:30   *42.9° C  18:00
START TIME 15:15    END TIME 18:00
```
FIG.12C
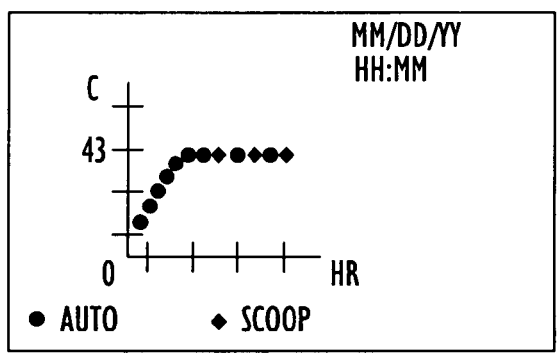
FIG.12D
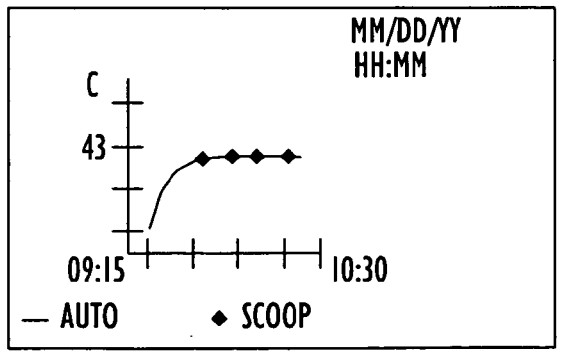
FIG.12E

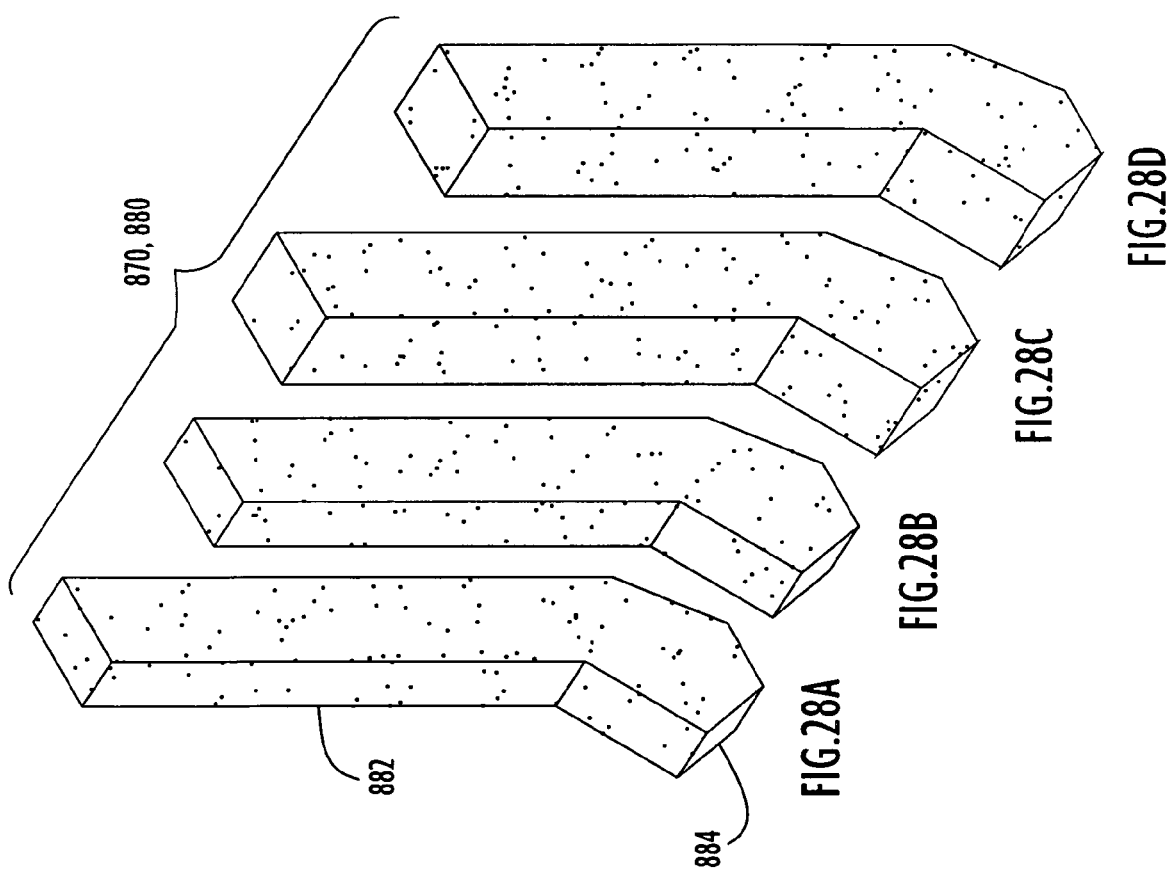

| 38° C 0:24 | RELOAD | 32° C 0:18 | 24° C 0:01 |
|---|---|---|---|
| 43° C 1:15 | 40° C 0:29 | OVERTEMP | 26° C 0:03 |
| 41° C 0:33 | RELOAD | 43° C 2:42 | RELOAD |
| RELOAD | 29° C 0:8 | 41° C 0:32 | 42° C 0:30 |

| 100° F 0:24 | RELOAD | 90° F 0:18 | 75° F 0:01 |
|---|---|---|---|
| 109° F 1:15 | 104° F 0:29 | OVERTEMP | 79° F 0:03 |
| 106° F 0:33 | RELOAD | 109° F 2:42 | RELOAD |
| RELOAD | 84° F 0:8 | 106° F 0:32 | 108° F 0:30 |

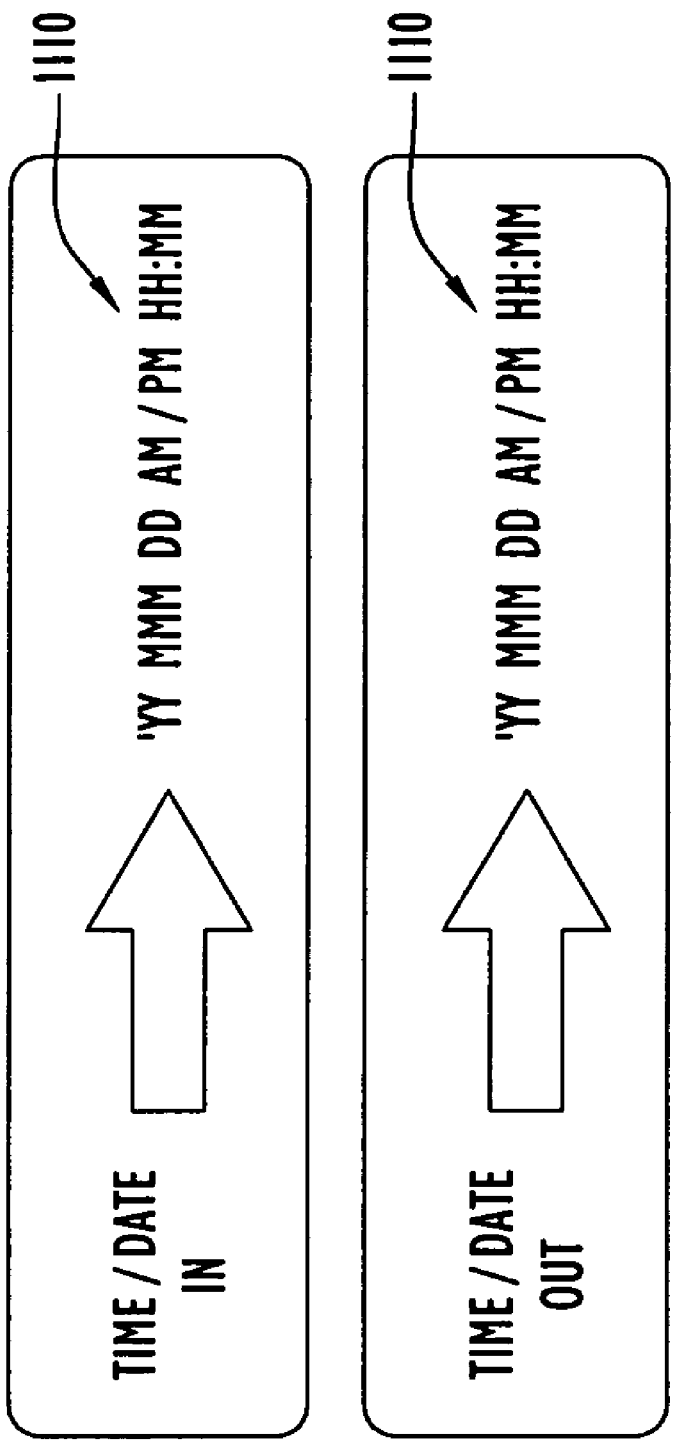

MEDICAL ITEM THERMAL TREATMENT SYSTEMS AND METHOD OF MONITORING MEDICAL ITEMS FOR COMPLIANCE WITH PRESCRIBED REQUIREMENTS

CROSS-REFERENCE TO RELATED APPLICATIONS

This application is a continuation of U.S. patent application Ser. No. 11/332,859, entitled "Medical Item Thermal Treatment Systems and Method of Monitoring Medical Items for Compliance with Prescribed Requirements" and filed Jan. 17, 2006, which is a continuation of U.S. patent application Ser. No. 10/805,487, entitled "Medical Item Thermal Treatment Systems and Method of Monitoring Medical Items for Compliance with Prescribed Requirements" and filed Mar. 22, 2004, now U.S. Pat. No. 7,041,941, which is a Continuation-in-Part of U.S. patent application Ser. Nos.: 09/982,832, entitled "Method and Apparatus for Monitoring Temperature of Intravenously Delivered Fluids and Other Medical Items" and filed Oct. 23, 2001, now U.S. Pat. No. 6,722,782, which is a divisional of U.S. patent application Ser. No. 09/539,183, entitled "Method and Apparatus for Monitoring Temperature of Intravenously Delivered Fluids and Other Medical Items" and filed Mar. 30, 2000, now U.S. Pat. No. 6,467,953, which claims priority from U.S. Provisional Patent Application Ser. No. 60/126,874, entitled "Method and Apparatus for Monitoring Temperature of Intravenously Delivered Fluids" and filed Mar. 30, 1999; 10/076,112, entitled "Medical Solution Warming System and Method of Heating and Maintaining Medical Solutions at Desired Temperatures" and filed Feb. 15, 2002, now U.S. Pat. No. 6,768,085, which claims priority from U.S. Provisional Patent Application Ser. No. 60/301,829, entitled "Medical Solution Warming System and Method of Heating and Maintaining Medical Solutions at Desired Temperatures" and filed Jul. 2, 2001; and 10/695,487, entitled "Warming System and Method for Heating Various Items Utilized in Surgical Procedures" and filed Oct. 29, 2003, which is a continuation of U.S. patent application Ser. No. 10/127,675, entitled "Warming System and Method for Heating Various Items Utilized in Surgical Procedures" and filed Apr. 23, 2002, now U.S. Pat. No. 6,660,974, which is a continuation-in-part of U.S. patent application Ser. No. 09/810,418, entitled "Warming System and Method for Heating Various Items Utilized in Surgical Procedures" and filed Mar. 19, 2001, now U.S. Pat. No. 6,376,805, which is a continuation of U.S. patent application Ser. No. 09/413,532, entitled "Warming System and Method for Heating Various Items Utilized in Surgical Procedures" and filed Oct. 6, 1999, now U.S. Pat. No. 6,294,762, which is a continuation-in-part of International Application No. PCT/US98/06951, entitled "Warming System and Method for Heating Various Items Utilized in Surgical Procedures" and filed Apr. 7, 1998, which claims priority from U.S. Provisional Patent Application Ser. No. 60/042,737, entitled "Warmer Cabinet for Use in Surgical Procedures" and filed Apr. 7, 1997.

In addition, U.S. patent application Ser. No. 10/805,487 claims priority to U.S. Provisional Patent Application Ser. Nos.: 60/456,394, entitled "Medical Solution Warming System and Method of Heating and Maintaining Medical Solutions at Desired Temperatures with Indications of Medical Solution Heating Time" and filed Mar. 21, 2003; 60/456,398, entitled "Temperature Control System and Method for Heating Medical Items and Providing Indications of Heating Time" and filed Mar. 21, 2003; 60/467,582, entitled "Medical Item Thermal Treatment System and Method of Monitoring and Reporting Time and Temperature of Thermally Treated Items" and filed May 5, 2003; 60/472,554, entitled "Method and Apparatus for Placing Time Stamp Information on Medical Items" and filed May 23, 2003; and 60/486,216, entitled "Method and Apparatus for Monitoring and Controlling Use of a Medical Item Thermal Treatment System" and filed Jul. 11, 2003. The disclosures of the above-mentioned patents and patent applications are incorporated herein by reference in their entireties.

BACKGROUND OF THE INVENTION

1. Technical Field

The present invention pertains to medical item thermal treatment and/or monitoring systems, such as the types disclosed in U.S. Pat. No. 5,408,576 (Bishop); U.S. Pat. No. 6,259,067 (Faries, Jr. et al.); U.S. Pat. No. 6,294,762 (Faries, Jr. et al.); U.S. Pat. No. 6,371,121 (Faries, Jr. et al.); U.S. Pat. No. 6,384,380 (Faries, Jr., et al.); U.S. Pat. No. 6,376,805 (Faries, Jr. et al.); U.S. Pat. No. 6,467,953 (Faries, Jr. et al.); U.S. Pat. No. 6,566,631 (Faries, Jr. et al.) and U.S. Pat. No. 6,660,974 (Faries, Jr. et al.); U.S. Patent Application Publication Nos.: 2002/0147426 (Faries, Jr. et al.) and 2003/0114795 (Faries, Jr. et al.); and U.S. patent application Ser. No. 09/380,507, entitled "Method and Apparatus for Pressure Infusion and Temperature Control of Infused Liquids" and filed Apr. 24, 2000. The disclosures of the foregoing patents, patent publications and patent applications are incorporated herein by reference in their entireties. In particular, the present invention is directed toward monitoring intravenous solution or other medical items for compliance with prescribed requirements (e.g., manufacturer, medical standards or regulations, etc.) from the time the solution is prepared through disposal of the solution after use in a medical procedure. In other words, the medical solution or other medical items are monitored from manufacture at a manufacturing plant, through transport and/or storage to an end user or medical facility, through subsequent thermal treatment by that user and during administration to a patient. In this manner, a complete record of temperature and/or other conditions for the medical item is ascertained to determine and/or indicate to medical personnel compliance with the prescribed requirements.

2. Discussion of Related Art

Various types of medical items require heating to a selected temperature prior to utilization in a medical procedure. Generally, the medical items may be heated for limited time intervals to preserve their effectiveness. These items typically include intravenous solutions, irrigation fluids, surgical instruments, bottles and blankets. Intravenous (IV) fluids, for example, are typically stored in a cool environment and, consequently, require heating to precise temperatures to prevent thermal shock and injury from occurring during infusion of the fluid into a patient. Similarly, irrigation fluids can be warmed or cooled to various temperatures depending upon their intended use. These types of fluids are typically provided to a patient utilizing a flexible bag or container filled with the fluid and delivered via a fluid line that conveys the fluid from the bag to the patient.

Some medical items can only be heated for a limited period of time, or in accordance with controlled warming cycles, in order to avoid adversely affecting their effectiveness. For example, some fluids, such as whole blood or fluids containing medication, should be warmed evenly to a specific temperature and can be rendered unusable or unsafe if all or a portion of the fluid is overheated.

In order to provide the necessary heated items for use in medical procedures, the related art provides devices for regulating and/or monitoring temperature of medical items. For example, ovens may be disposed within operating rooms to heat items to desired temperatures. Further, U.S. Pat. No. 4,419,568 (Van Overloop) discloses a wet dressings heater having a base with side walls defining a cavity, and an insert connected to the base and defining at least one recess in the cavity for receiving wet dressings. A heater has an electrical heating element in close proximity to the insert recess for heating the wet dressings, while the temperature of the heating element is controlled in a desired temperature range for those wet dressings.

U.S. Pat. No. 4,495,402 (Burdick et al.) discloses a warmer for heating wet dressings and other articles disposed within a heating and storage compartment. The articles are arranged within the compartment in stacked relation and disposed on a plate that is supplied with thermal energy from a heater. The plate includes a center aperture whereby a first thermal sensor is disposed in the aperture in contact with a bottom most article. Control circuitry is disposed beneath the plate to control the heater to maintain temperature of the bottom most article at a desired level based on the temperatures sensed by the first thermal sensor and a second thermal sensor responsive to heater temperature.

U.S. Pat. No. 4,859,360 (Suzuki et al.) discloses a blood bag having a temperature-monitoring device in the form of a tag or label adhered to the bag outer surface. The temperature-monitoring device includes plural reversible temperature indicators each associated with a specific temperature range to indicate a current temperature of the blood, and an irreversible temperature indicator to indicate that the blood has currently or previously reached a predetermined temperature. The reversible indicators individually provide visual indications in response to the current blood temperature being within a corresponding range, while the irreversible indicator maintains a visual indication once the predetermined temperature has been reached.

U.S. Pat. No. 5,408,576 (Bishop) discloses an intravenous fluid warmer having a cabinet structure to accommodate a plurality of intravenous fluid bags. A temperature sensor and pad of heating filaments are disposed within the cabinet structure, whereby the temperature sensor enables automatic temperature regulation of the pad of heating filaments to heat the intravenous fluid bags. The heating filaments are covered by a rubber layer to prevent melting of the bags during heating. A temperature indicator disposed on the cabinet structure permits a user to ascertain when a desired temperature is attained, whereby an intravenous fluid bag is removed from the intravenous fluid warmer via an opening defined in a side of the cabinet structure.

U.S. Pat. No. 5,986,239 (Corrigan, III et al.) discloses a conductive warmer for flexible plastic bags. The warmer includes a heat-conducting member of thermally conductive material having a plurality of fins which are parallel and spaced apart to define a plurality of bag-receiving compartments. The fins are connected to a back portion of the heat-conducting member to which a heating element is attached in a heat-exchanging relationship. The heating element conducts heat through the back portion and fins of the heat-conducting member to the bags.

The devices described above suffer from several disadvantages. In particular, temperature and heating requirements are typically prescribed for medical solutions or other medical items from various sources (e.g., manufacturer, medical standard or regulation, etc.). These requirements typically prescribe a particular temperature range, expiration date or time and certain time intervals for heating the medical solution in order to maintain the solution efficacy. The above-described devices generally do not monitor medical items for or indicate compliance with these prescribed requirements throughout the life of the medical item (e.g., from manufacture through use and disposal). For example, the above-described warming devices may provide a temperature indication during heating, but do not monitor the heating time intervals for the medical items, the medical item temperatures during storage or usage outside of the device or the medical item expiration date. Although the Suzuki et al. device is secured to and monitors temperature of a blood bag, there is no manner for that device to monitor or indicate the heating intervals and/or passage of the expiration date or time for the blood bag. Thus, medical personnel may unknowingly administer to patients solutions and/or medication that are unusable and/or have reduced potency due to non-compliance with prescribed requirements (e.g., an exceeded expiration date, prolonged exposure to heat, attainment of temperatures outside the prescribed range, etc.), thereby risking serious injury to patients.

OBJECTS AND SUMMARY OF THE INVENTION

Accordingly, it is an object of the present invention to monitor medical item conditions and indicate compliance with prescribed requirements from the time the item is prepared through item disposal after use (e.g., throughout the life of the medical item) to prevent use of compromised medical items with patients.

It is another object of the present invention to thermally treat medical items and monitor medical item conditions (e.g., heating time, temperature, etc.) for, and/or indicate compliance with, prescribed requirements.

Yet another object of the present invention is to control usage of thermal treatment systems.

Still another object of the present invention is to monitor medical item conditions during thermal treatment and generate hardcopy or electronic reports indicating those conditions.

A further object of the present invention is to mark or otherwise transcribe information associated with a medical item on that medical item to notify medical personnel of the medical item status with respect to prescribed requirements.

The aforesaid objects may be achieved individually and/or in combination, and it is not intended that the present invention be construed as requiring two or more of the objects to be combined unless expressly required by the claims attached hereto.

According to the present invention, various devices enable medical personnel or users to adhere to medical regulatory and medical item manufacturer requirements relating to medical item heating time, temperature and/or other conditions in order to ensure patient safety. For example, intravenous (IV) fluid bags are typically heated to precise temperatures to prevent thermal shock and injury from occurring during infusion of the IV fluid into a patient. Generally, the fluid bags may be heated for limited time intervals to preserve their effectiveness. These time limits may be prescribed by medical standards or regulations, or by the manufacturer of the fluid. A medical solution container or other medical item of the present invention includes a monitoring or data recording device to monitor and/or record medical solution conditions. The device may further include indicators to indicate compliance of the medical solution with prescribed requirements (e.g., manufacturer, medical standard or regulation, etc.), typically pertaining to medical solution temperature and heating time intervals sufficient to maintain efficacy of the medical solution. The monitoring device may be embedded within or disposed on a container wall or, alternatively, be disposed within the solution, and may utilize a wireless communication link to transfer recorded information.

The medical solution container may alternatively include an electronic memory device attached to or contained within the medical solution container. The memory device is capable of recording information received from an external device, such as a thermal treatment system that has been configured to store warming cycle time, temperature and/or other information in the respective container embedded devices. The container may further include electronically activated visible indicators that are triggered based upon compliance with prescribed requirements.

The medical solution container may alternatively include an external barcode or transponder, where the solution container is identified with a unique bar code and/or transponder signal or code that identifies the container to a thermal treatment system measuring medical solution conditions. The thermal treatment system may transmit event data and/or other information pertaining to the container to a central database.

In another embodiment, the medical solution container may include electrochromic ink cells and a control circuit. The control circuit monitors external and/or internal conditions of the container environment and triggers individual electrochromic cells in response to the presence of one or more conditions (e.g. max temperature limit exceeded, max humidity exceeded, etc.) to indicate compliance with prescribed requirements. Alternatively, monitoring may be performed by an external unit, such as a thermal treatment system or a box used to transport medical solutions or other sensitive components. In this case, the container includes the electrochromic cells (and, preferably, text identifying the meaning of each) and a conducting lead to connect the container and corresponding electrochromic cells to the external monitoring unit. The unit monitors the container environment and activates selected electrochromic cells upon the container to cause the electrochromic cell to change color (e.g., from clear to opaque, etc.) upon determining that allowable conditions have been exceeded. In addition, the electrochromic cell on the container may be manually activated by pressing a current source button upon the container to cause the electrochromic cell to change color, thereby allowing a manual over-ride to indicate medical item status with respect to the prescribed requirements.

The present invention further includes various thermal treatment systems that monitor medical solution containers or other medical items for prescribed requirements (e.g., temperature, heating time intervals, etc.) and display the monitored parameters to medical personnel. These systems may be utilized with conventional medical solution containers or the containers described above to monitor solution conditions. The thermal treatment systems may be monitored and controlled via an information device containing operational parameters. Moreover, the systems may monitor the time, temperature and/or other conditions of thermally treated items to generate reports (e.g., printed reports, displays, reports in electronic form, etc.) for users.

In addition, the present invention may place time stamp information on medical solution containers (e.g., bags or bottles containing saline or intravenous (IV) solutions, antibiotics or other drugs, blood, etc.) or other medical items (e.g., instruments, blankets, etc.) to enable determination by medical personnel of compliance with prescribed requirements (e.g., residence time within a thermal treatment system, the remaining effective or utilization life of the medical solution or other item, etc.).

The above and still further objects, features and advantages of the present invention will become apparent upon consideration of the following detailed description of specific embodiments thereof, particularly when taken in conjunction with the accompanying drawings, wherein like reference numerals in the various figures are utilized to designate like components.

BRIEF DESCRIPTION OF THE DRAWINGS

FIGS. 12A-12I are schematic illustrations of exemplary reports produced by the system of FIG. 10 in accordance with the present invention.

FIGS. 28A-28D are views in perspective of exemplary guides of the system of FIG. 27A.

FIGS. 31A-31B are schematic illustrations of exemplary display screens for the system of FIG. 30 with temperature indications in Celsius and Fahrenheit, respectively.

FIGS. 37A-37B are schematic illustrations of exemplary labels with time stamp information for placement on a medical item according to the present invention.

DETAILED DESCRIPTION OF THE PREFERRED EMBODIMENTS

The present invention enables monitoring of a medical item (e.g., medical solution containers or bags, etc.) for compliance with prescribed requirements (e.g., manufacturer, medical standard or regulation, etc.) to ensure the medical item maintains efficacy and remains pharmaceutically acceptable. The present invention enables monitoring (e.g., continuously and/or at any intervals, etc.) of the medical item at each or any of the stages (e.g., manufacture, transport, storage, thermal treatment, use with patients, etc.) from the time the solution is prepared through disposal of the solution after use in a medical procedure. In other words, a medical solution or other medical items are monitored (e.g., temperature, heating time, age or utilization life, etc.) from manufacture at a manufacturing plant, through transport and/or storage to an end user or medical facility, through subsequent thermal treatment by the end user and/or during administration of the solution to a patient. In this manner, a complete record of temperature and/or other conditions for the medical item is ascertained to determine and/or indicate to medical personnel compliance with the prescribed requirements. Thus, the present invention basically enables users to conform to regulatory and medical item manufacturer requirements, typically relating to medical item heating time, utilization life and temperature, in order to ensure patient safety.

Figure 1:
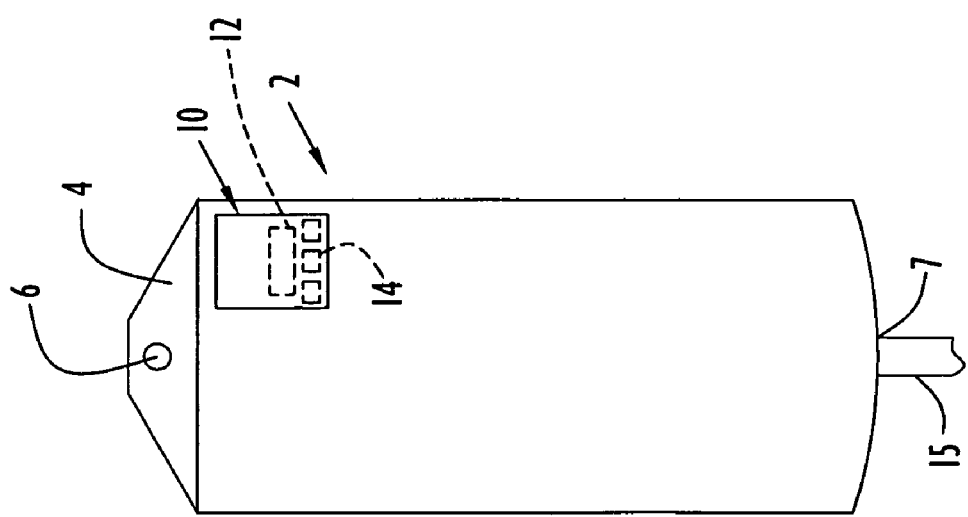
FIG. 1 is a view in perspective of a medical solution container including a monitoring device to monitor solution conditions according to the present invention.

A medical item including a monitoring device according to the present invention is illustrated in FIG. 1. Initially, a medical item 2 is preferably an intravenous solution bag; however, the medical item may be implemented by a wide variety of medical items (e.g., medical solution containers, saline solutions, IV solutions and/or lines, instruments, blankets, antibiotics or other drugs, blood, irrigation fluid and/or lines, etc.). Specifically, intravenous solution bag 2 is in the form of a conventional intravenous solution bag and is constructed of plastic or other materials commonly utilized for forming those types of bags. The solution bag may contain various types of solutions, such as saline solution, blood, antibiotic or other drugs, or any other intravenously administered solution. Intravenous solution bag 2 further includes a generally triangular projection 4 attached to and extending from the bag upper portion. Projection 4 preferably includes a truncated upper portion having an opening or hole 6 defined therein for interfacing an intravenous pole or other support structure (not shown). The bag lower portion includes an outlet 7 and associated fluid conduits 15 to interface an intravenous tube (not shown) and enable the solution to flow through the tube from the outlet to a patient.

Generally, intravenous solutions are required to be within a specific temperature range prior to and/or during infusion to avoid injury to a patient as described above. For example, fluids intravenously administered to a patient have a temperature near the patient body temperature, preferably in the approximate range of 86° F.-104° F., and should not exceed a maximum temperature to maintain solution efficacy. Further, the solutions typically have a prescribed utilization life or expiration date and heating time in order to maintain their efficacy as described above. The present invention monitors conditions of the solution bag in order to ensure compliance with the prescribed requirements (e.g., from the medical item manufacturers, medical standard or regulation, etc.). In particular, solution bag 2 further includes a monitoring or data recording device 10. The monitoring device includes or is coupled to sensors 16 (FIG. 2) to monitor the solution bag from the time the bag is filled with fluid to the process of dispensing the fluid to the patient. The monitoring device measures and stores information (e.g., age of solution, time, temperature, humidity, heating interval, maximum temperature attained, manufacturing date, expiration date or time, amount or volume of solution, strength of solution, diluent, directions, etc.). The measured information may be measured either on a periodic basis or in response to an incremental positive or negative change in a monitored parameter (e.g., a change in temperature, humidity, etc.).

Monitoring device 10 is typically attached to the interior or exterior bag surface in a manner enabling the sensors to measure solution conditions. The monitoring device may be attached to or embedded within the bag surface at any desired locations via any conventional or other techniques (e.g., adhesive, welding, lamination, etc.). For example, the monitoring device may be attached to the bag during bag construction, where a pouch or receptacle (not shown) may be adhered or sealed to the bag interior or exterior surface to receive the monitoring device. Alternatively, the monitoring device may be disposed within the bag interior in a suspended or floating state within the solution. In this case, the monitoring device may include any conventional or other suitable floatation devices to suspend the device within the solution.

The monitoring device may further include a display 12 and/or indicators 14 to indicate measured parameters to medical personnel. The display may be of any shape, size or type (e.g., LED, LCD, etc.), may be disposed at any location on the monitoring device or bag and may display any information. Indicators 14 are preferably implemented by light emitting diodes (LED) and may indicate to medical personnel conditions and/or compliance with prescribed requirements. The indicators may be disposed at any locations on the monitoring device or bag and may be activated based upon a local assessment of the recorded information or based upon an external assessment of the recorded information by an external processor. In addition, the activation of the indicators may be based upon local or external assessment of the recorded information with respect to stored predetermined parameters relating to the prescribed requirements. The monitoring device further includes an interface 20 (FIG. 2) to facilitate communications with an external device 21 as described below and transfer recorded information. The external device may be coupled to an external database for storage and retrieval of information.

Figure 2:
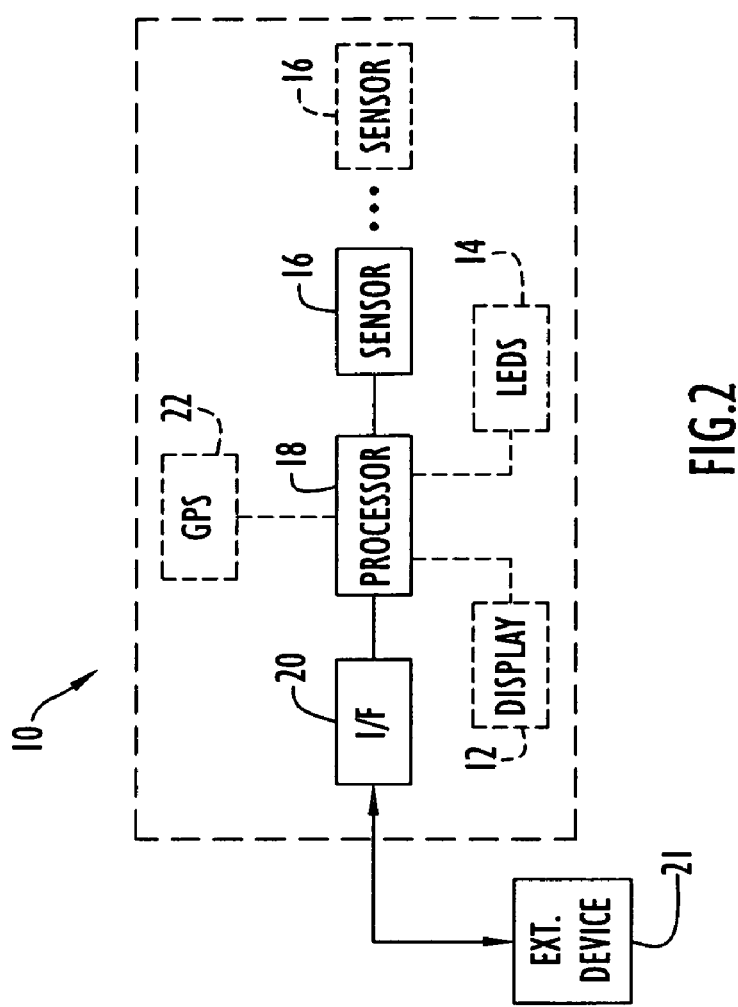
FIG. 2 is a schematic block diagram of the monitoring device of FIG. 1.

Referring to FIG. 2, monitoring device 10 includes one or more sensors 16, a processor 18 and an interface 20. A power source (not shown), preferably in the form of batteries, provides power to the components. The monitoring device may further include display 12 and/or indicators 14 as described above. Processor 18 is typically implemented by a conventional microprocessor and controls operation of the monitoring device. However, the processor may alternatively be implemented by any hardware or circuitry. The processor is coupled to display 12, indicators 14, sensors 16 and interface 20. Sensors 16 are preferably implemented by various conventional or other sensors (e.g., proximity sensors, pressure sensors, temperature sensors (e.g., RTD, infrared, etc.), presence sensors, weight sensors, volume sensors, flow sensors, fluid sensors, fluid level sensors, etc.) to measure corresponding conditions (e.g., solution temperature, humidity, fluid level, etc.). The sensors may be disposed in a common monitoring device housing or be external of the monitoring device within the solution bag to measure the corresponding conditions. The measured parameters are provided to processor 18, where the processor may record the measured conditions and time of measurement for storage and/or display. The stored values may be downloaded to an external device 21 as described below. The monitoring device may further record item locations (e.g., manufacturing plant, storage locations, transport, medical facility, etc.) and/or other information to correspond with the time, temperature and/or other recordings as described below.

The monitoring device is typically activated at the fluid bag manufacturing plant. As the bag is being produced, solution temperatures and/or other conditions are recorded in the processor (or an external) memory. In addition, the monitoring device may store solution information from the manufacturer or other source (e.g., name, strength, amount or volume, expiration date or time, date prepared and diluent, location, directions, etc.). The monitoring device records the temperature of the solution and/or other conditions as the bag moves from the manufacturer, through shipping and storage to the end user or medical facility. The monitoring device further records solution temperature and/ or other conditions in the event of thermal treatment of the bag by the end user and during administration of solution to the patient. This provides medical personnel or the medical facility with a complete record of temperature and/or other conditions for each solution bag to enable determination of compliance with prescribed requirements (e.g., age, temperature, re-warming, heating intervals, etc.) based on the information in the record.

The processor may further include information associated with the prescribed requirements (e.g., age, temperature, heating intervals, no re-warming, etc.) and determine compliance with those requirements based on the measured values. This enables the requirements to be programmable, where the monitoring device may be used for any medical solutions and/or prescribed requirements. The measured values and/or a compliance indication may be indicated to medical personnel via display 12 and/or indicators 14. For example, the processor may control the display to indicate the measured values, prescribed requirements and/or an indication (e.g., message, symbol, etc.) of non-compliance with those requirements. The indicators may be of different colors to indicate compliance (e.g., a green LED), marginal compliance (e.g., a yellow LED) or non-compliance (e.g., a red LED) with any of those requirements (e.g., the indicators may be associated with any quantity of the requirements (e.g., expiration date, temperature, heating interval, re-warming, etc.) to indicate non-compliance with those requirements). Thus, the monitoring device continuously monitors medical items for compliance with prescribed requirements at each stage of the solution life and immediately indicates non-compliance or a compromised solution to medical personnel.

Interface 20 is coupled to processor 18 and facilitates communications with an external device 21 for transfer of information. The interface is typically in the form of a conventional wireless transceiver (e.g., RF, infrared, etc.) to communicate with the external device. The external device may be in the form of a corresponding wireless transmitter/ receiver (e.g., RF, infrared, etc.) of a processing device or system (e.g., computer station or system, hand-held device, etc.). The recorded information in the processor may be downloaded at any time by the use of the wireless transmitter/receiver. A user positions the solution bag in close proximity to the wireless transmitter/receiver, where the external device instructs the monitoring device to transmit the recorded information from memory. Alternatively, the interface may be in the form of a connector or port for connection to a corresponding port of the external device (e.g., connection to the processing device or system) via a cable. The interface receives an instruction from the external device and forwards the request to the processor to retrieve the desired information. The processor further controls interface 20 to provide the information to the requesting device.

The information transmitted to the external device includes raw data that is processed by the external wireless transmitter/receiver or processing system to produce a user friendly format (e.g., a data sheet, a line graph that charts the temperatures over time and location, etc.). The resulting information may be presented on a screen for the user to view, printed for documentation purposes or stored in local or remote database accessible by users or medical personnel.

Location information (e.g., codes for a manufacturer loading dock, hospital receiving or Operating Room, etc.) may be entered into the external device by the user (e.g., by keying into the wireless transmitter/receiver or processing device the location code) for subsequent transmission to the monitoring device for storage. This enables monitored parameters to be associated with the location of the bag. Alternatively, the monitoring device may further include a conventional Global Positioning System (GPS) transceiver 22 to communicate with a GPS satellite to obtain location and/or time information. The transceiver may be implemented by any conventional or other GPS transceiver and is coupled to and controlled by processor 18 to retrieve the information for storage.

The external device may further enable entry or provide various information (e.g., start date and start time of solution or other item heating/cooling, the time interval the solution or other item was heated/cooled, the temperature the solution or other item attained during heating/cooling and/or the time and temperature of the solution or other item when the solution was removed from the system (e.g., partial or complete history of time and solution or other item temperature, facility information (e.g., including name, location, etc.), patient information (e.g., including patient identification number, patient age, patient name, patient sex, patient medications, patient diagnoses, patient commodities and conditions, patient lab values, patient allergies and sensitivities, patient weight and height, patient pregnancy and lactation status, dosage information, etc.), doctor information, type of procedure, the solution information described above, type of instruments or other item being heated/cooled, amount or quantity of solution or other item being heated/cooled, etc.) for transmission to and storage in the monitoring device. The external devices may be disposed at various locations (e.g., manufacturing plant, transport station, medical facility, etc.) to enable entry and/or retrieval of information. Alternatively, the information may be entered into the monitoring device or retrieved for display on display 12 via processor input devices (e.g., keypad, etc.). The monitoring device may further determine and/or indicate various conditions relating to the entered information. For example, a monitoring device equipped with fluid sensors may determine and/or indicate, via display 12 and/or indicators 14, when an appropriate dosage has been administered to a patient. Moreover, the monitoring device may include a unique identifier, where external device 21 may retrieve and store information from the monitoring device in a local or remote central database based on the identifier for subsequent access by users or medical personnel. This enables information for the particular bag to be retrieved and examined and/or be utilized for tracking, inventory and/or availability purposes. By way of example, solution bags 2 may communicate with external devices disposed at various locations (e.g., manufacturing plant, transport, storage, medical facility, etc.) to enable the bags to be located or tracked (e.g., via location codes or the GPS). The information may further be stored in a database and accessed to determine inventory and/or solution availability for the particular location. In addition, the monitoring device and/or centrally stored information may immediately notify medical personnel of compromised solutions (e.g., expired, damaged, contaminated, unsafe, etc.), thereby enabling easy identification and segregation of those compromised items until proper disposal. The processor and/or interface may utilize any conventional or other suitable protocol to communicate with and transfer information with the external device.

In operation, the solution bag is constructed with fluid and appropriate information is stored in the monitoring device. The bag is transported to an intended facility, where the monitoring device continuously monitors the solution. Prior to use, medical personnel may view the monitoring device (and/or access the central database) to determine compliance with prescribed requirements. The monitoring device continues to monitor the solution and indicate compliance during thermal treatment and/or administration of solution to a patient. The monitoring device may be disposable with the bag or re-programmed for use with subsequent bags.

The monitoring device may further be configured to communicate with a thermal treatment system as described below to transfer the recorded information. In this case, the thermal treatment system includes the wireless transmitter/receiver or connection port to continuously communicate with interface 20 of the monitoring device as described above. The recorded information may be utilized by the thermal treatment system to control heating of the solution bag to a desired set point temperature.

Figure 3:
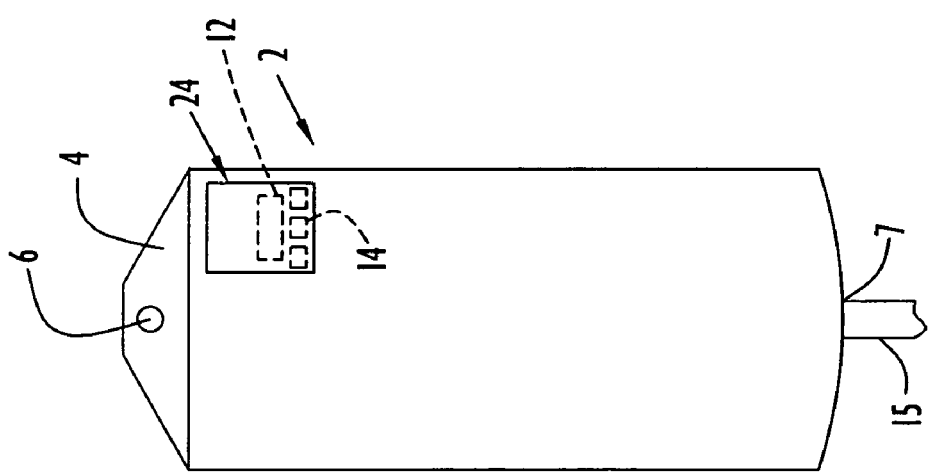
FIG. 3 is a view in perspective of a medical solution container including a memory device to record and/or indicate solution conditions according to the present invention.

A medical item including a memory device to store information pertaining to conditions measured by a thermal treatment system according to the present invention is illustrated in FIG. 3. Initially, medical item 2 is substantially similar to the medical item described above and is preferably an intravenous solution bag, but may be a wide variety of medical items (e.g., medical solution containers, saline solutions, IV solutions and/or lines, instruments, blankets, antibiotics or other drugs, blood, irrigation fluid and/or lines, etc.). Specifically, intravenous solution bag 2 includes a generally triangular projection 4 attached to and extending from the bag upper portion and including opening or hole 6 defined therein as described above for interfacing an intravenous pole or other support structure (not shown). The bag lower portion includes an outlet 7 and associated fluid conduits 15 to interface an intravenous tube (not shown) and enable the solution to flow through the tube from the outlet to a patient as described above.

The present invention records conditions of the solution bag measured by a thermal treatment system in order to ensure compliance with the prescribed requirements. In particular, solution bag 2 further includes a memory device 24. The memory device records information received from an external device 21, such as a thermal treatment system treating the solution bag. The thermal treatment system is configured to measure and transmit warming cycle, time-temperature and other information (e.g., start date and start time of solution or other item heating/cooling, the time interval the solution or other item was heated/cooled, the temperature the solution or other item attained during heating/cooling and/or the time and temperature of the solution or other item when the solution was removed from the system (e.g., partial or complete history of time and solution or other item temperature), the facility, patient and/or solution information described above, doctor information, type of procedure, type of instruments or other item being heated/cooled, amount or quantity of solution or other item being heated/cooled, etc.) to the memory device as described below.

Memory device 24 is typically attached to or embedded within the bag surface and may be disposed at any desired locations via any conventional or other techniques (e.g., adhesive, welding, lamination, etc.). For example, the monitoring device may be attached to the bag during bag construction, where a pouch or receptacle (not shown) may be adhered or sealed to the bag interior or exterior surface to receive the memory device. Alternatively, the memory device may be disposed within the bag interior in a suspended or floating state within the solution. In this case, the memory device may include any conventional or other suitable floatation devices to suspend the device within the solution.

The memory device may further include a display 12 and/or indicators 14 to indicate measured parameters to medical personnel. The display may be of any shape, size or type (e.g., LED, LCD, etc.), may be disposed at any location on the memory device or bag, and may display any information. Indicators 14 are preferably implemented by light emitting diodes (LED) and may indicate to medical personnel conditions and/or compliance with prescribed requirements as described above. The indicators may be disposed at any locations on the memory device or bag and may be activated based upon a local assessment of the recorded information or based upon an external assessment of the recorded information by an external processor as described above. For example, the memory device may activate a visible indicator each time a warming cycle is initiated by a thermal treatment system or trigger a visible indicator in response to exceeding a pre-determined maximum number of warming cycles or heating interval, the solution temperature being beyond an acceptable temperature range, rewarming of the bag, etc. The activation of the indicators may be based upon various criteria (e.g., stored logical data and concurrently measured physical data, etc.). In addition, the activation of the indicators may be based upon the local or external assessment of the recorded information with respect to stored predetermined parameters relating to the prescribed requirements. The memory device further includes an interface 20 (FIG. 4) to facilitate communications with a thermal treatment system as described below and receive information.

Figure 4:
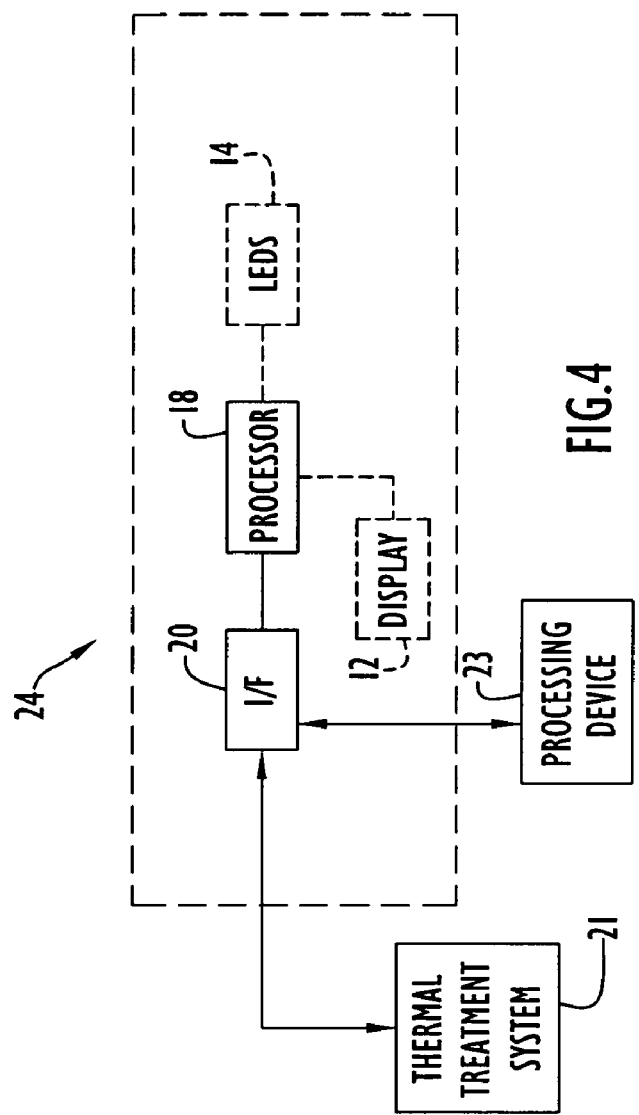
FIG. 4 is a schematic block diagram of the memory device of FIG. 3.

Referring to FIG. 4, memory device 24 includes processor 18 and interface 20. A power source (not shown), preferably in the form of batteries, provides power to the components. The memory device may further include display 12 and/or indicators 14 as described above. Processor 18 is substantially similar to the processor described above and controls operation of the memory device. The processor is coupled to display 12, indicators 14 and interface 20. Interface 20 facilitates communications with an external device 21 to transfer information. The external device is typically in the form of a thermal treatment system as described below that treats the solution bag. The thermal treatment system may include various sensors (e.g., proximity sensors, pressure sensors, temperature sensors (e.g., RTD, infrared, etc.), presence sensors, weight sensors, volume sensors, flow sensors, fluid sensors, fluid level sensors, etc.) to measure conditions of the solution (e.g., temperature, heating intervals, time, humidity, etc.) for transfer to the memory device. The interface may be in the form of a conventional wireless transceiver as described above to communicate with a wireless transmitter/receiver of the thermal treatment system or, alternatively, may be in the form of a conventional connector to physically connect to a port or connector of the thermal treatment system. The thermal treatment system receives the solution bag and measures various conditions or parameters either periodically or in response to changes in conditions (e.g., measures conditions each predetermined time interval, in response to changing conditions, etc.). The measured parameters are transmitted from the thermal treatment system to processor 18, where the measured conditions and time of measurement may be stored in the processor (or an external) memory and/or displayed. The memory device may further record locations (e.g., medical facility, etc.) and other information (e.g., patient, solution and/or facility information, etc.) received from the thermal treatment system. This information may correspond with the time, temperature and/or other recordings as described above. The location and other information may be entered by a user via system input devices.

The interface may further facilitate communications between the memory device and an external device 23 for downloading the recorded information to that external device. In this case, external device 23 may be in the form of a processing device or system (e.g., computer station or system, hand-held device, etc.). The recorded information in the memory device may be downloaded at any time by the use of the wireless transmitter/receiver or physical connector. A user positions the solution bag to communicate with the external device (e.g., in close proximity to the device for a wireless link, in a manner enabling the connector to engage the external device port or connector, etc.), where the external device instructs the memory device to transmit the recorded information from memory. The interface receives the instruction and forwards the request to the processor to retrieve the desired information. The processor further controls interface 20 to provide the information to the requesting device.

The information transmitted to external device 23 includes raw data that is processed by the external device to produce a user friendly format (e.g., a data sheet, a line graph that charts the temperatures over time and location, etc.). The resulting information may be presented on a screen for the user to view, printed for documentation purposes or stored in a local or remote database accessible by users or medical personnel as described above. The memory device may include a unique identifier to associate the bag with the stored information as described above. This enables locating or tracking of bags based on stored location information, and ascertaining solution inventory and availability as described above. The processor and/or interface may utilize any conventional or other suitable protocol to communicate with and transfer information with the external processing device and thermal treatment system.

The processor may further include information associated with the prescribed requirements and determine compliance with those requirements based on the measured values as described above. This enables the requirements to be programmable, where the memory device may be used for any medical solutions and/or prescribed requirements. The measured values and/or a compliance indication may be indicated to medical personnel via display 12 and/or indicators 14. For example, the processor may control the display to indicate the measured values, prescribed requirements and/or an indication (e.g., message, symbol, etc.) of non-compliance with those requirements as described above. The indicators may be of different colors to indicate compliance (e.g., a green LED), marginal compliance (e.g., a yellow LED) or non-compliance (e.g., a red LED) with those requirements as described above. The memory device may be disposable with the bag or re-programmed for use with subsequent bags.

Figure 5:
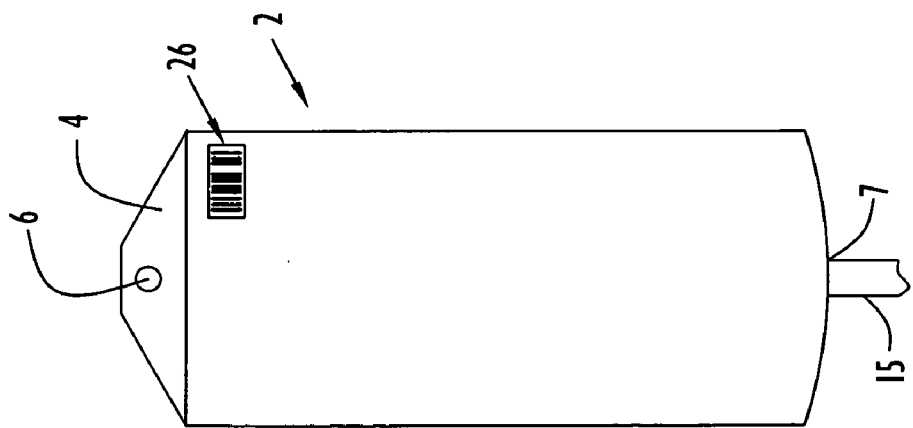
FIG. 5 is a view in perspective of a medical solution container including a bar code serving to identify the medical solution container according to the present invention.

The solution bags described above include devices to basically store measured conditions and other information for respective solutions within those bags. Alternatively, the information for medical items may be stored based on an item identifier in a central storage unit or database accessible by users or medical personnel. A medical item including an identifier in the form of a bar code is illustrated in FIG. 5. Initially, medical item 2 is substantially similar to the medical items described above and is preferably an intravenous solution bag, but may be a wide variety of medical items (e.g., medical solution containers, saline solutions, IV solutions and/or lines, instruments, blankets, antibiotics or other drugs, blood, irrigation fluid and/or lines, etc.). Specifically, intravenous solution bag 2 includes a generally triangular projection 4 attached to and extending from the bag upper portion and including opening or hole 6 defined therein as described above for interfacing an intravenous pole or other support structure (not shown). The bag lower portion includes an outlet 7 and associated fluid conduits 15 to interface an intravenous tube (not shown) and enable the solution to flow through the tube from the outlet to a patient as described above.

Solution bag 2 further includes a bar code 26 disposed on the bag. The bar code includes a unique identifier associated with the bag to identify the bag to a thermal treatment system treating the solution bag. The thermal treatment system is configured to measure and transmit warming cycle, time-temperature and/or other information (e.g., start date and start time of solution or other item heating/cooling, the time interval the solution or other item was heated/cooled, the temperature the solution or other item attained during heating/cooling and/or the time and temperature of the solution or other item when the solution was removed from the system (e.g., partial or complete history of time and solution or other item temperature), doctor information, type of procedure, type of instruments or other item being heated/cooled, amount or quantity of solution or other item being heated/cooled, etc.) to a central storage unit or database accessible by users or medical personnel as described below. The database may further receive the patient, solution and/or facility information described above for the medical item (e.g., entered by a user via thermal treatment system input devices or a workstation). Bar code 26 is typically attached to or embedded within the bag surface and may be disposed at any desired locations on the bag via any conventional or other techniques (e.g., adhesive, welding, lamination, etc.). For example, the bar code may be attached to the bag during bag construction, where the bar code may be adhered or sealed to the bag interior or exterior surface. The bar code may be updated and reapplied to the solution bag to provide any desired additional information (e.g., requirements, manufacturing date, operational parameters, etc.).

A thermal treatment system receives the bag and includes a bar code reader to ascertain the item identification as described below. The thermal treatment system may include various sensors (e.g., proximity sensors, pressure sensors, temperature sensors (e.g., RTD, infrared, etc.), presence sensors, weight sensors, volume sensors, flow sensors, fluid sensors, fluid level sensors, etc.) to measure solution conditions and provides information (e.g., temperature, heating intervals, time, humidity, etc.) for transfer to a central storage unit. The thermal treatment system measures various conditions or parameters either periodically or in response to changes in conditions (e.g., measures conditions each predetermined time interval, in response to changing conditions, etc.). The measured parameters are transmitted from the thermal treatment system to a central storage unit to record the measured conditions and information. A common interface may be employed to permit a wide range of devices (e.g., ranging from thermal treatment systems, intelligent storage rooms, workstations, etc.) to report information (e.g., the solution, patient and/or facility information described above, etc.) related to the treatment of each container (e.g., with a bar code) to a central database. The thermal treatment system may further record item locations (e.g., medical facility, storage facility, etc.) to correspond with the recorded information as described above. The central storage unit may be local or accessed by the thermal treatment system via a network as described below. The transferred information may be retrieved by users or medical personnel to monitor the solution bag for compliance with the prescribed requirements. Further, the stored information may be utilized for item tracking, inventory and/or availability purposes as described above.

Figure 6:
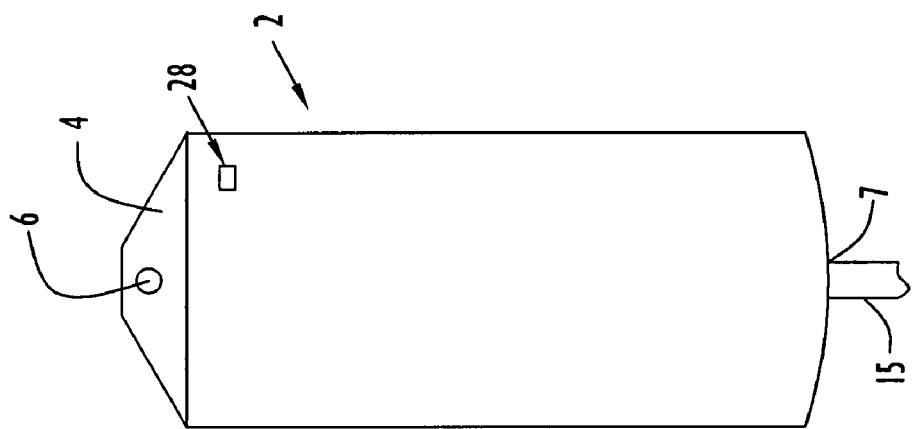
FIG. 6 is a view in perspective of a medical solution container including a transponder unit according to the present invention.

A medical item including an identifier in the form of a transponder unit according to the present invention is illustrated in FIG. 6. Initially, medical item 2 is substantially similar to the medical items described above and is preferably an intravenous solution bag, but may be a wide variety of medical items (e.g., medical solution containers, saline solutions, IV solutions and/or lines, instruments, blankets, antibiotics or other drugs, blood, irrigation fluid and/or lines, etc.). Specifically, intravenous solution bag 2 includes a generally triangular projection 4 attached to and extending from the bag upper portion and including opening or hole 6 defined therein as described above for interfacing an intravenous pole or other support structure (not shown). The bag lower portion includes an outlet 7 and associated fluid conduits 15 to interface an intravenous tube (not shown) and enable the solution to flow through the tube from the outlet to a patient as described above.

Solution bag 2 further includes an identifier in the form of a transponder unit 28. The transponder unit provides a unique identifier associated with the bag that identifies the bag to a thermal treatment system treating that bag. The thermal treatment system is configured to measure and transmit warming cycle, time-temperature and/or other information (e.g., start date and start time of solution or other item heating/cooling, the time interval the solution or other item was heated/cooled, the temperature the solution or other item attained during heating/cooling and/or the time and temperature of the solution or other item when the solution was removed from the system (e.g., partial or complete history of time and solution or other item temperature), doctor information, type of procedure, type of instruments or other item being heated/cooled, amount or quantity of solution or other item being heated/cooled, etc.) to a central storage unit or database accessible by users or medical personnel as described below. The database may further receive the patient, solution and/or facility information described above for the medical item (e.g., entered by a user via thermal treatment system input devices or a workstation). The transponder unit may be attached to or embedded within the bag surface and may be disposed at any desired locations on the bag via any conventional or other techniques (e.g., adhesive, welding, lamination, etc.). For example, the transponder unit may be adhered or sealed to the bag interior or exterior surface.

Figure 7:
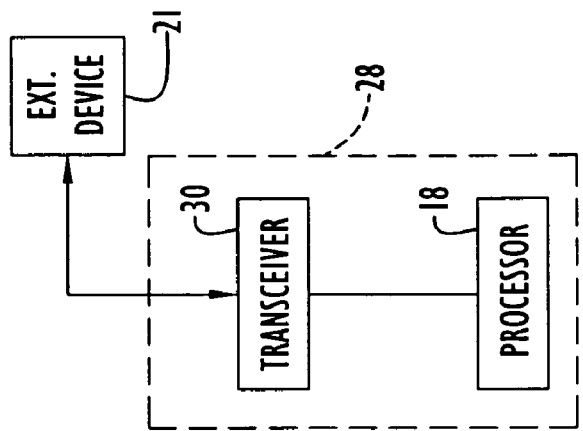
FIG. 7 is schematic block diagram of the transponder unit of FIG. 6.

Referring to FIG. 7, transponder unit 28 includes processor 18 and a transceiver 30. A power source (not shown), preferably in the form of batteries, provides power to the components. Processor 18 is substantially similar to the processor described above and controls operation of the transponder unit. Transceiver 30 facilitates communications with an external device 21 in the form of a thermal treatment system as described below that treats the solution bag. The transceiver may be in the form of a conventional wireless transceiver (e.g., RF, infrared, etc.) to communicate with a corresponding wireless transmitter/receiver of the thermal treatment system.

The thermal treatment system receives the bag and includes the wireless transmitter/receiver to receive transmissions from the transponder unit to ascertain the item identification. The thermal treatment system further includes various sensors (e.g., proximity sensors, pressure sensors, temperature sensors (e.g., RTD, infrared, etc.), presence sensors, weight sensors, volume sensors, flow sensors, fluid sensors, fluid level sensors, etc.) to measure solution conditions and provide information (e.g., temperature, heating intervals, time, humidity, etc.) for transfer to a central storage unit. The thermal treatment system measures various conditions or parameters either periodically or in response to changes in conditions (e.g., measures conditions each predetermined time interval, in response to changing conditions, etc.). The measured parameters are transmitted from the thermal treatment system to a central storage unit to record the measured conditions and information. Alternatively, the transponder unit may receive and store the measured parameters and other information from the thermal treatment system in the processor (or an external) memory as described above. A common interface may be employed to permit a wide range of devices (e.g., ranging from thermal treatment systems, intelligent storage rooms, etc.) to report information (e.g., the solution, patient and/or facility information described above, etc.) related to the treatment of each container (e.g., with a transponder unit) to a central database. The thermal treatment system may further record item locations (e.g., medical facility, storage facility, etc.) to correspond with the recorded information as described above. The central storage unit may be local or accessed by the thermal treatment system via a network as described below. The transferred information may be retrieved by users or medical personnel to monitor the solution bag for compliance with the prescribed requirements. Further, the stored information may be utilized for tracking, inventory and/or availability purposes as described above. The transponder unit may be disposable with the bag or re-programmed for use with subsequent bags.

Figure 8:
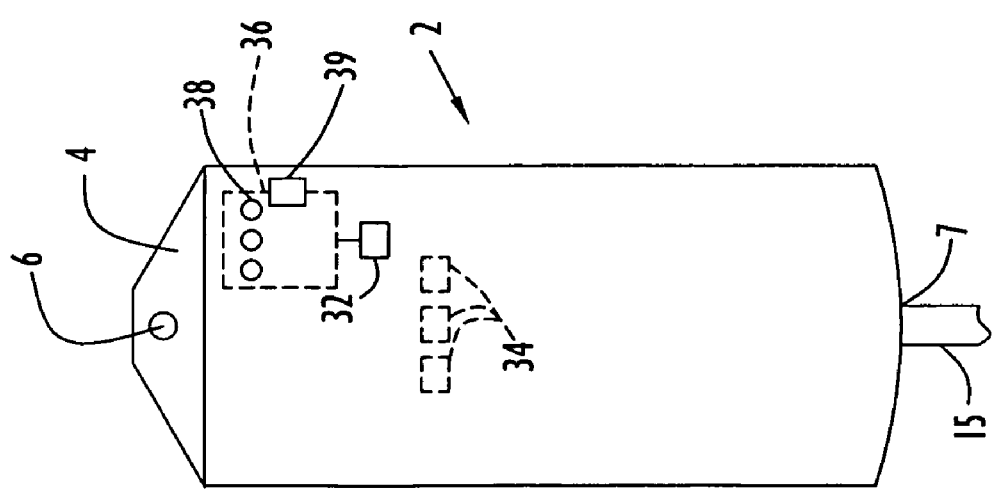
FIG. 8 is a view in perspective of a medical solution container including electrochromatic cells to indicate solution conditions according to the present invention.

A medical item including electrochromic ink cells to indicate solution compliance with prescribed requirements according to the present invention is illustrated in FIG. 8. Initially, medical item 2 is substantially similar to the medical items described above and is preferably an intravenous solution bag, but may be a wide variety of medical items (e.g., medical solution containers, saline solutions, IV solutions and/or lines, instruments, blankets, antibiotics or other drugs, blood, irrigation fluid and/or lines, etc.). Specifically, intravenous solution bag 2 includes a generally triangular projection 4 attached to and extending from the bag upper portion and including opening or hole 6 defined therein as described above for interfacing an intravenous pole or other support structure (not shown). The bag lower portion includes an outlet 7 and associated fluid conduits 15 to interface an intravenous tube (not shown) and enable the solution to flow through the tube from the outlet to a patient as described above.

Solution bag 2 further includes electrochromic ink cells 38 and a control circuit 32 that monitors external and/or internal conditions of the container environment and triggers individual electrochromic cells in response to one or more conditions (e.g., max temperature limit exceeded, max humidity exceeded, re-warming, solution expired, etc.) to indicate compliance with prescribed requirements. Examples of electrochromic ink cells that may be employed by the present invention are disclosed in U.S. Pat. No. 6,294,111 (Shacklett, III et al.), the disclosure of which is incorporated herein by reference in its entirety. The ink cells may be of any quantity, shape or size and may be disposed on a label 36 affixed to the bag. The label may be of any size or shape with the ink cells being arranged thereon in any fashion. The control circuit may include various sensors and triggers an appropriate electrochromic cell upon conditions specific to the contents of the bag being exceeded. One or more cells are associated with a particular condition (e.g., a particular temperature, humidity, a temperature or time interval exceeded, passage of an expiration date, re-warming of the bag, etc.) to notify a user or medical personnel of the occurrence of that condition. The prescribed requirements may be programmed into the control circuit based upon the specific contents of the bag to allow the requirements to be tailored to the needs of the bag.

The ink cells and/or label may be attached to or embedded within the bag surface and may be disposed at any desired locations on the bag via any conventional or other techniques (e.g., adhesive, welding, lamination, etc.). For example, the ink cells and/or label may be adhered or sealed to the bag interior or exterior surface.

Figure 9:
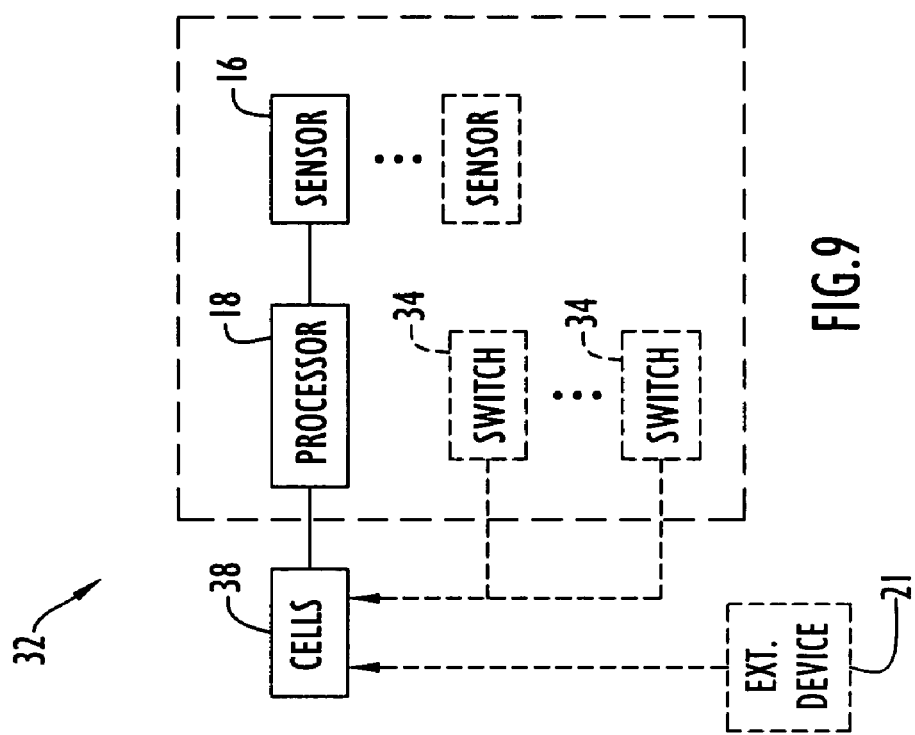
FIG. 9 is a schematic block diagram of a control circuit for the electrochromatic cells of FIG. 8.

Referring to FIG. 9, control circuit 32 includes one or more sensors 16 and processor 18. A power source (not shown), preferably in the form of batteries, provides power to the components. Processor 18 is substantially similar to the processor described above and controls operation of the control circuit. The processor is coupled to sensors 16 and ink cells 38. Sensors 16 are preferably implemented by various sensors (e.g., proximity sensors, pressure sensors, temperature sensors (e.g., RTD, infrared, etc.), presence sensors, weight sensors, volume sensors, flow sensors, fluid sensors, fluid level sensors, etc.) to measure corresponding conditions (e.g., solution temperature, humidity, etc.). The sensors may be disposed within the control circuit or be external of the circuit within the solution bag to measure the corresponding conditions. The measured parameters are provided to processor 18, where the processor includes information associated with the prescribed requirements. The processor determines compliance with those requirements based on the measured values to activate the appropriate ink cells associated with the condition. The ink cells may be activated by the processor altering voltage signals provided to these cells. Activation of the cell produces a color change (e.g., change from one color to another, clear to opaque, opaque to clear, etc.) to indicate conditions. This enables the requirements to be programmable, where the ink cells and control circuit may be used for any medical solutions and/or prescribed requirements. The measured values and/or a compliance indication may be indicated to medical personnel via the ink cells. For example, the processor may control the ink cells to indicate the measured values, prescribed requirements and/or an indication (e.g., message, symbol, etc.) of non-compliance with those requirements.

The solution bag may alternatively include the ink cells with the control circuit being disposed within an external device 21. The external device may be in the form of a thermal treatment system or a housing used to transport medical solutions or other sensitive components. In this case, solution bag 2 includes the electrochromic ink cells (and, preferably, text identifying the meaning of each) and a conducting lead to an external location upon the bag where a remote monitoring clip 39 can be attached to connect the electrochromic cells to the external device. The external device monitors the bag environment and provides control signals to activate selected electrochromic cells on the bag to cause the corresponding electrochromic cell to change color (e.g., from clear to opaque, from one color to another, etc.) upon determining that allowable conditions have been exceeded. This allows a user or medical personnel to view a visible identification mark on the bag indicating that bag contents have exceeded allowed storage conditions and may be compromised.

In addition, solution bag 2 may include one or more current source buttons or switches 34 each associated with a corresponding electrochromic cell to activate that cell (e.g., change color, etc.) as described above. The buttons provide voltage signals to activate the corresponding cell in response to actuation and basically serve as a manual over-ride to allow a user or medical personnel to indicate and/or identify the bag contents as compromised.

Figure 10:
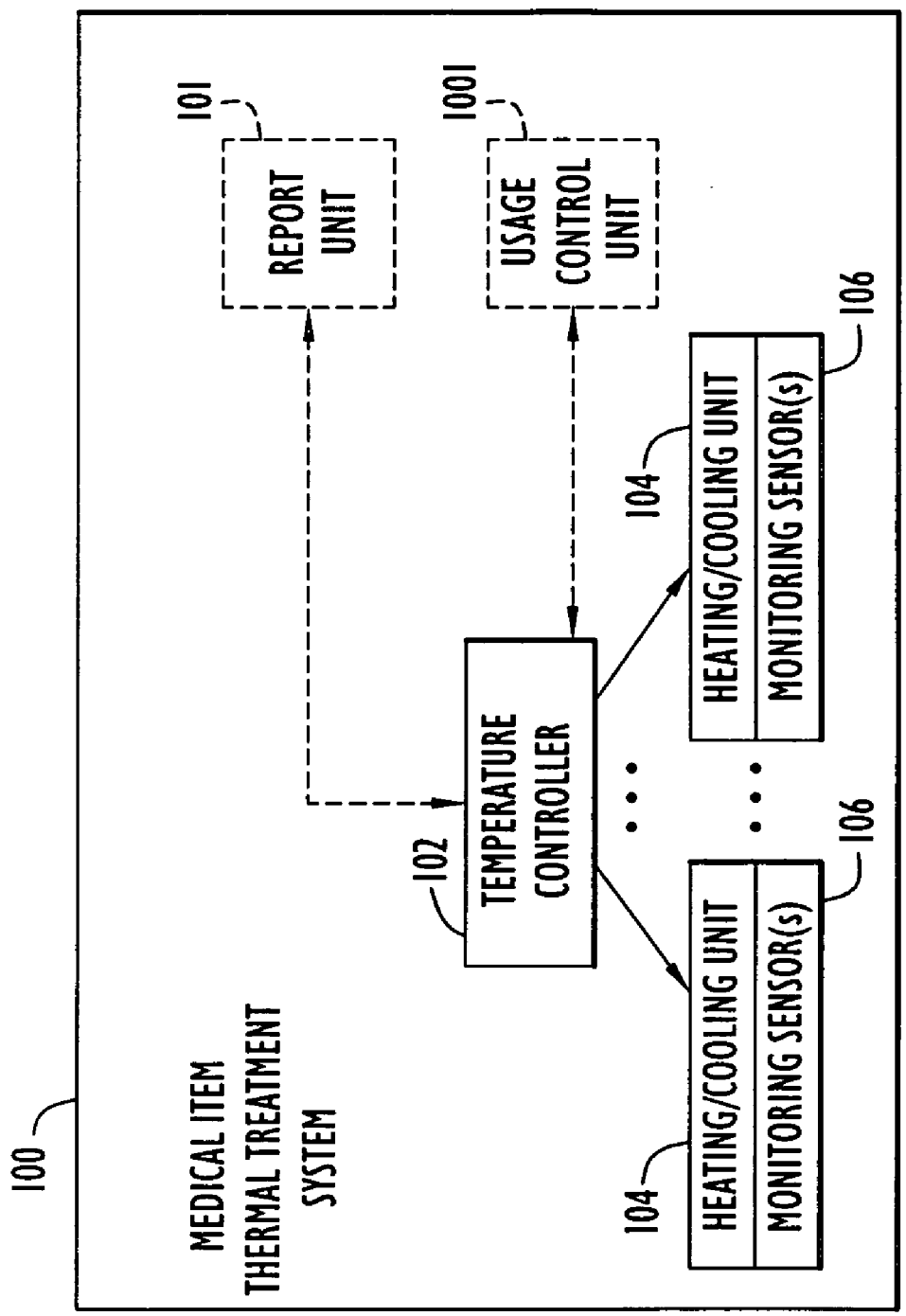
FIG. 10 is a system level block diagram of an exemplary thermal treatment system that monitors thermally treated items and may generate reports and/or control system usage according to the present invention.

The medical items described above enable measurement and/or recordation of medical item conditions from the manufacturing plant through transport, storage, thermal treatment and/or administration to a patient. This enables the medical item to be monitored at each or any of the stages throughout the life of the medical item and to notify users or medical personnel of compliance with prescribed requirements. Thermal treatment systems thermally treating solution bags (e.g., conventional solution bags or the bags described above) or other medical items may monitor and/or record solution conditions for compliance with the prescribed requirements according to the present invention. In addition, the present invention may enable control of thermal treatment system use. An exemplary medical item thermal treatment system 100 to monitor and/or record medical item conditions and/or employing usage control according to the present invention is illustrated in FIG. 10. The system may thermally treat a wide variety of medical items (e.g., medical solution containers, saline solutions, IV solutions and/or lines, instruments, blankets, antibiotics or other drugs, blood, irrigation fluid and/or lines, etc.). Specifically, system 100 may be of any of the types of thermal treatment systems disclosed in the aforementioned patents, patent publications and patent applications and includes a temperature controller 102, one or more heating/cooling units 104 and one or more monitoring sensors 106 associated with each heating/cooling unit. The heating/cooling units (and/or corresponding sensors) are associated with a corresponding individual medical item or a system compartment receiving medical items to be treated. The system may further include a report unit 101 and a usage control unit 1001. The report unit facilitates collection of measured information to generate a report, while the usage control unit enables control of system operation as described below.

Temperature controller 102 may be implemented by any conventional or other controller or microprocessor (e.g., chip, card, processor, circuitry, etc.) and controls heating/cooling units 104 to thermally treat a corresponding system compartment and/or medical item to a desired temperature. Monitoring sensors 106 are disposed in the proximity of a corresponding heating/cooling unit 104 or medical item to detect various conditions (e.g., the insertion, presence and/or removal of a medical item within the system, the medical item and/or heating/cooling unit temperature, etc.). Monitoring sensors 106 may be implemented by any conventional or other sensors (e.g., proximity sensors, pressure sensors, temperature sensors (e.g., RTD, infrared, etc.), presence sensors, weight sensors, volume sensors, flow sensors, fluid sensors, fluid level sensors, etc.) to measure and provide any information, and are coupled to temperature controller 102. The temperature controller and/or monitoring sensors may be further coupled to report unit 101 and/or usage control unit 1001.

Temperature controller 102 typically includes input devices (not shown) to receive a desired or set point temperature for each medical item and/or system compartment from a user and a display (not shown) to display the desired and/or measured temperatures for each medical item and/or compartment. The temperature controller compares the set point temperature for a medical item and/or compartment to the corresponding measured temperature and controls the associated heating/cooling unit accordingly to maintain the medical item and/or compartment at or near the desired temperature. For example, the temperature controller may disable heating (or enable cooling) in response to a measured temperature exceeding a desired temperature. Conversely, the temperature controller may enable heating (or disable cooling) in response to a measured temperature below a desired temperature. Heating/cooling units 104 may be implemented by any conventional or other heating and/or cooling devices (e.g., heating pad or coils, refrigeration coils, thermoelectric device, etc.).

Figure 11:
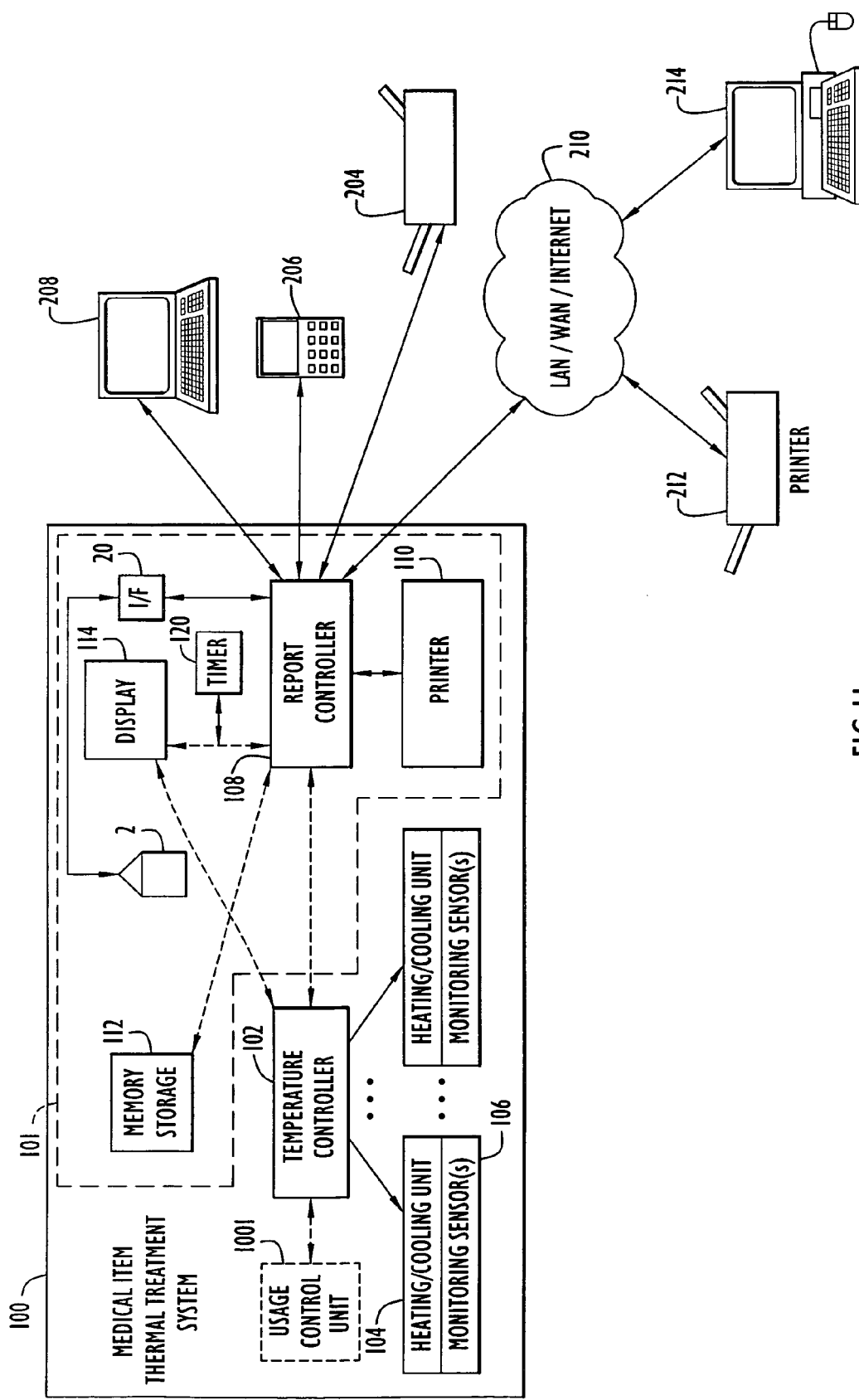
FIG. 11 is a block diagram of the report unit within the system of FIG. 10 to generate and/or print reports according to the present invention.

Referring to FIG. 11, report unit 101 includes a report controller 108, interface 20, a printer 110, memory storage 112, a display 114 and/or a timer 120. The system includes devices to measure, record and/or provide a report (e.g., hardcopy or electronic form) of system conditions (e.g., time, date, temperature, fluid loss or removal, etc.) as described below. The report provides medical personnel documentation for their files on the heating/cooling characteristics. The primary information produced is the start date and start time of solution or other item heating/cooling, the time interval the solution or other item was heated/cooled, the temperature the solution or other item attained during heating/cooling and/or the time and temperature of the solution or other item when the solution was removed from the system (e.g., partial or complete history of time and solution or other item temperature). The report may further include a variety of information (e.g., doctor information, type of procedure, type of instruments or other item being heated/cooled, amount or quantity of solution or other item being heated/cooled, etc.). Specifically, report controller 108 is coupled to temperature controller 102 and receives various information (e.g., enablement/disablement of units 104, temperature, etc.) related to thermal treatment of the medical item. The report controller may receive any additional information (e.g., the facility, patient and/or solution information described above, doctor information, etc.) from medical personnel or users via report controller input devices (not shown). The report controller may be implemented by any conventional or other controller or microprocessor (e.g., chip, card, processor, circuitry, etc.). Alternatively, the temperature controller and report controller may be implemented by a single controller (e.g., temperature controller 102).

The report controller further maintains the date, elapsed heating/cooling time and occurrence time of an event or condition (e.g., the time when medical items are inserted and/or removed from the system, etc.). The time may be measured and/or displayed by the report controller or by timer 120 as described below. The report controller may measure the elapsed time or record an occurrence time based on signals received from the temperature controller and/or input devices. For example, the report controller may initiate measurement of a time interval in response to the temperature controller indicating enablement of heating/cooling units 104, and may store the elapsed and/or occurrence time in response to any condition (e.g., when solution or other item is removed). The report controller may further measure elapsed time or record elapsed and/or occurrence time in response to medical personnel manually entering information on the report controller input devices (e.g., start and stop keys). The report controller collects the appropriate information and arranges the information into a report. The report may be arranged in any fashion and include any desired information. The report controller may further provide corresponding information to solution bag 2 via interface 20 as described above. The interface may be in the form of a wireless transmitter/receiver (e.g., RF, infrared, etc.) or a connector or port to communicate with the solution bag as described above. Alternatively, the interface may be in the form of a bar code reader to identify a particular medical item and enable the report controller to transmit corresponding information to a central database for review, tracking, inventory and/or availability purposes as described above. Moreover, the report and/or information may be stored in a memory device (e.g., local memory, removable memory, card, disk, etc.) for later retrieval as described below. In addition, the report controller and/or timer are coupled to display 114 to display the elapsed (or running) time, report or any desired information to medical personnel. The information displayed may be selected via report controller input devices, or the display may include display controls (e.g., buttons, keys, etc.). The report may further be printed by the report controller via printer 110. The printer, timer and display may be implemented by any conventional or other printer, timing and/or display devices.

A memory storage device 112 is coupled to report controller 108 and is used to store the collected information. Basically, the report controller logs records containing system information (e.g., the date/time that a medical item is inserted into system 100, the date/time that the medical item is removed from the system, temperatures, etc.). In this manner, use of the medical item warming/cooling system is documented with recorded log entries. Log triggering events can be user defined via report controller input devices that allow the system to be configured to record information in response to a wide variety of detected conditions and/or at particular times or periodic intervals. The memory storage can be used to store a wide variety of information related to use of the system and the thermal treatment of individual medical items and can be any type of storage media. For example, memory storage device 112 can include, but is not limited to, an electronic memory chip, a smart card, a floppy disk, a fixed or removable magnetic disk. The report controller may be configured to support one or more of those memory storage types.

The system may record information regarding each medical item placed in the system. The information collected and/or recorded by the report controller and/or produced in a report can include, but is not limited to: the date/time that a medical item was placed into/removed from the medical item warming/cooling system, the temperature of the medical item upon being placed into/removed from the medical item warming/cooling system, the temperature of the medical item at specific points in time while stored in the medical item warming/cooling system, start date and time that the medical item began to be heated/cooled, the length of time that the medical item was heated/cooled, the temperature that the medical item was heated/cooled to during the heating/cooling cycle and/or the amount of solution or other item residing, placed in or removed from the system. The report may also include related information, such as patient information (e.g., name, identification number and/or the other patient information described above), facility information (e.g., name, location and/or the other facility information described above), doctor information, the type of procedure, the solution information described above, the type of item being heated/cooled, the amount or quantity of fluid or other item being heated/cooled (e.g., fluid (or other item) level, volume or weight), the flow rate of fluid that is being heated/cooled, the pressure of fluid flow as the fluid is heated/cooled and any other desired information. The thermal treatment system may employ any type of sensors or sensing devices (e.g., temperature sensors, presence sensors, weight sensors, volume sensors, pressure sensors, flow sensors, fluid sensors, fluid level sensors, etc.) as described above to measure and provide any desired information to the report controller for inclusion in a report. The recordation or collection may occur automatically or via user entered information (e.g., start, stop and/or record keys) as described above.

Report controller 108 stores and retrieves information from memory storage 112 in order to produce a report with any desired information. The report may be transmitted to printer device 110 that may be integrated within medical warming/cooling system 100. The report may further be displayed by the report controller on display 114. The printer basically provides a report in hardcopy form. The report controller may control the printer to produce the report at specified times (e.g., termination of heating/cooling, at particular times of day, after a particular quantity of uses, etc.) or in response to requests from medical personnel via report controller input devices (e.g., print key). The printer may print the report on any desired hardcopy medium. Preferably, the printer places the information onto a label that may be attached to a medical file and/or to the medical item. The information may be printed during or after the item heating/cooling, or be stored on a memory device and printed at a desired time as described above. The printer may further provide additional copies of the report in response to user requests, or a medium automatically creating duplicates may be utilized (e.g., carbon-less paper, etc.).

The report or other information may alternatively be provided in electronic form. The report controller may facilitate communication with other devices for transference or downloading of the report or other information to those devices. For example, the information may be downloaded or transmitted over a network or other communications medium to another device (e.g., PDA, computer, another thermal treatment system, etc.) for viewing, storage and/or printing. Further, the report controller may transmit the report or other information to solution bag 2 via interface 20 or identify the solution bag or other medical item via an identifier (e.g., bar code or transponder) and transfer corresponding information to a central database as described above. An externally attached device can be connected to warming/cooling system 100 via a direct local connection or via a network connection. Network connections to report controller 108 can include any combination of cable-based or radio-based local area network (LAN), wide area network (WAN), or Internet network links. The external local device or network connection can use a cable-based or radio-based connection to a port, or network card, on system 100.

Moreover, the report controller may facilitate retrieval of information (e.g., the patient, facility and/or solution information described above, doctor information, item (e.g., instrument, etc.) information, etc.) from a database, network or other source for the report.

Report controller 108 is capable of transmitting generated reports or any desired information to internally mounted printer 110, a locally connected external printer 204, a locally connected personal digital assistant (PDA) 206 and/or a locally connected computer workstation 208 (e.g., including or coupled to the central database storing medical item information). Further, report controller 108 is capable of transmitting generated reports via a LAN/WAN/Internet network 210 to remotely connected devices, such as a network connected printer 212 and/or a network connected computer workstation 214 (e.g., including or coupled to the central database for storing medical item information). In addition, plural systems 100 may be coupled to a network to enable a workstation to access the system reports or medical item information remotely (e.g., via a LAN, Internet server or website, etc.) to enable monitoring of medical item compliance with prescribed requirements.

Information is collected by report controller 108 and stored in memory storage 112, typically in real-time, as events occur. Reports or medical item information can be generated and printed/displayed or transmitted (e.g., to the medical item, external devices or databases, etc.) in a timely manner to allow a local or remote (e.g., at network workstation or computer 214) user to monitor the status of one or more systems and the status of medical items undergoing thermal treatment. Alternatively, reports or other information can be generated and printed/displayed or transmitted at a time of a user choosing. For example, a user either local to or remote from a system is able to monitor the temperature of medical items and the time that medical items have been stored within a medical item warming/cooling system based upon reports printed or shown on a display device. The user may access stored information relating to one or more medical item warming/cooling systems 100 by requesting (e.g., via report controller input devices, a remote workstation, etc.) that a report be produced or displayed to a specific printer or display (e.g., local or remote). Further, the information stored by the medical item or solution bag 2 may be downloaded to an external device as described above to monitor conditions.

The present invention generates and/or transmits reports to a display, printer, medical item or external device based upon concurrently monitored information, or based upon information stored within a memory storage device. The printed reports or transmitted information create a permanent log record that documents events that occur within the medical item warming/cooling system. Thus, a valuable, previously unavailable source of historical information is available to doctors, nurses, technicians, and hospital staff for use in support of patient record keeping, compliance with medical standards, scheduling routine maintenance, detecting malfunctioning devices, assessing costs to a specific operating team or medical patient, and adjusting the number and types of medical item warming/cooling systems to meet demand based upon actual use. The reports or information may be generated, displayed, transmitted and/or printed at particular times or concurrently with system operation (e.g., as information is measured and/or collected) to provide current system information (e.g., the printouts and/or displays may be updated continuously with report information).

Figure 12F:
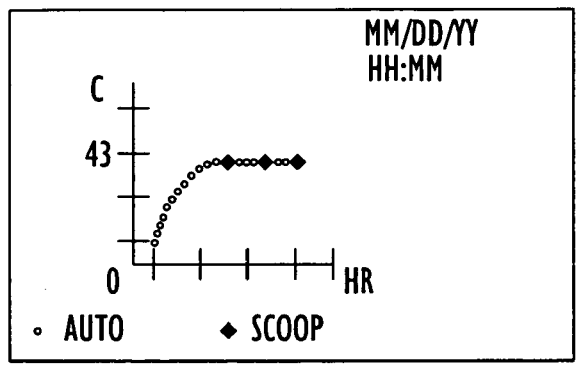
Figure 12G:
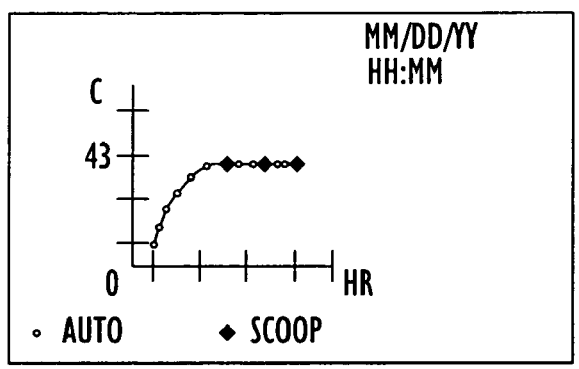
Figure 12H:
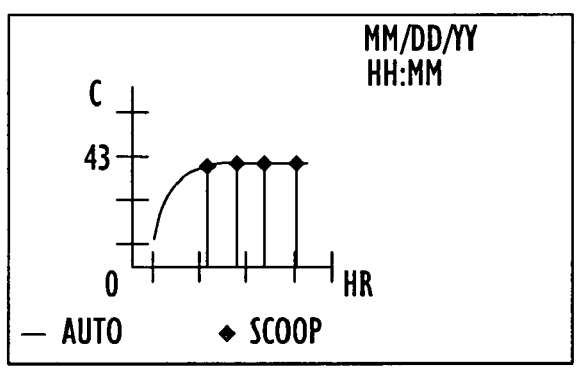
Figure 12I:
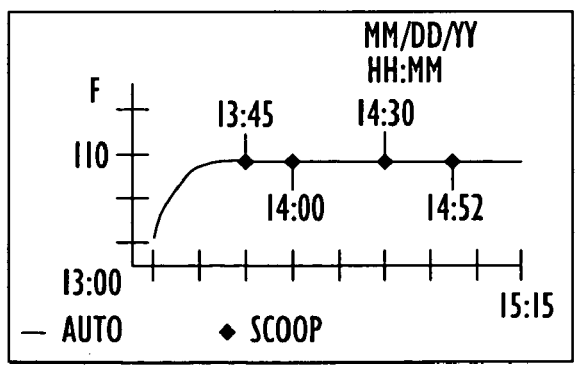

An exemplary report of information that may be produced by report controller 108 and transmitted to and/or printed or displayed on locally or remotely connected devices (e.g., display, medical item, printer, etc.) is illustrated in FIG. 12A. The report can include a wide variety of information. Exemplary report information may include medical item warming/cooling data 302 (e.g., type of item/fluid, intended use, start date, start time, duration, start temperature, removal temperature, fluid flow pressure (if applicable) and/or the other solution information described above). Other exemplary report information may include patient information 304 (e.g., patient name, patient id#, blood type and/or the other patient information described above), warming/cooling system information 306 (e.g., warming/cooling system ID, warming/cooling chamber ID, warming/cooling system serial number, manufacturer's number, last inspected date, inspected by and next inspection date), facility information 308 (e.g., facility name, facility location, doctor's information, type of procedure and/or the other facility information described above) and report metadata 310 (e.g., data collected date/time, report generation date/time and operating technician).

The report controller may provide any desired information (or any portions of the information to provide a more consolidated report) arranged in any fashion. For example, the report or transmitted information can include only a system ID number and select item warming/cooling data. The report can be adapted to display a wide variety of information that addresses a wide variety of warming/cooling system configurations. Further, generated reports will vary depending upon the configuration and use of the respective medical item warming/cooling systems and the information desired for a medical item. The information can be displayed locally or upon any printer/display connected to the medical item warming/cooling system. Further, information stored in a medical item may be downloaded as described above.

Alternative exemplary reports are illustrated in FIGS. 12B-12I. The reports of FIGS. 12B-12C include the date (e.g., month, day year (MM/DD/YY) or any other desired format), current time (e.g., hours and minutes (HH:MM) or any other desired format), start and end time (e.g., hours and minutes or any other desired format) of item heating/cooling and item temperatures at various points in time. The item temperatures are arranged, by way of example only, in a columnar format. The times may be at any desired periodic intervals or in response to a particular condition. For example, reports for IV solution warming (e.g., FIGS. 18, 21, 22, 27A and 30) or open basin (e.g., FIG. 20) type systems may indicate the temperature of solution or solution containers measured at any desired time interval (e.g., fifteen minutes, two minutes, one minute, etc.). Alternatively, reports for an open basin type system (e.g., FIG. 20) may indicate the time and temperature of solution when the solution is removed or scooped from the basin. These reports may further indicate the amount of solution residing, placed in and/or removed or scooped from the basin.

The reports of FIGS. 12D-12I generally provide time and temperature information in graphical form. In particular, these reports include the date (e.g., month, day year (MM/DD/YY) or any other desired format), current time (e.g., hours and minutes (HH:MM) or any other desired format) and graphs showing solution or other item temperature in relation to time. The graphs include an abscissa or 'X' axis associated with time and an ordinate or 'Y' axis associated with temperature. The time axis may extend for several hours (e.g., FIGS. 12D and 12F-12H) or for a particular time interval or time of day (e.g., FIGS. 12E and 12I). A series of temperature symbols (e.g., dots) are placed on the graph to indicate the temperature of solution or other item at a given time (e.g., FIGS. 12D and 12F). The temperature symbols may be connected by or reside on a line (e.g., FIG. 12G), or the line may be utilized (without the temperature symbols) to provide a continuous report of time and temperature (e.g., FIGS. 12E, 12H and 12I). In addition, a removal symbol (e.g., diamond) may reside in the line (e.g., FIGS. 12E, 12G-12I) or series of temperature symbols (e.g., FIGS. 12D and 12F) to indicate times when solution or other items are removed. The time of removal may be indicated by reference lines extending from the removal symbols to the time axis (e.g., FIG. 12H), or by placing the actual removal time (e.g., in hours and minutes (HH:MM) or any other desired format) proximate the removal symbol (e.g., FIG. 12I). These reports are typically utilized by open basin type systems (e.g., FIG. 20), where the reports may further indicate the amount of solution residing, placed in and/or removed or scooped from the basin. However, the reports may be utilized by any types of medical item thermal treatment systems, such as those disclosed in the aforementioned patents, patent publications and patent applications. The reports described above may be printed, transmitted and/or displayed at particular times or continuously and updated as data is collected (e.g., the graphs and/or columns may be updated with information as time progresses, etc.). The continuous reports are generally utilized for IV warming type systems and medical items (e.g., bag or line warmers, medical items, solution bags, etc.) to provide a continuous printout, display or history of item temperature, but may be utilized with any medical item thermal treatment system.

Figure 13:
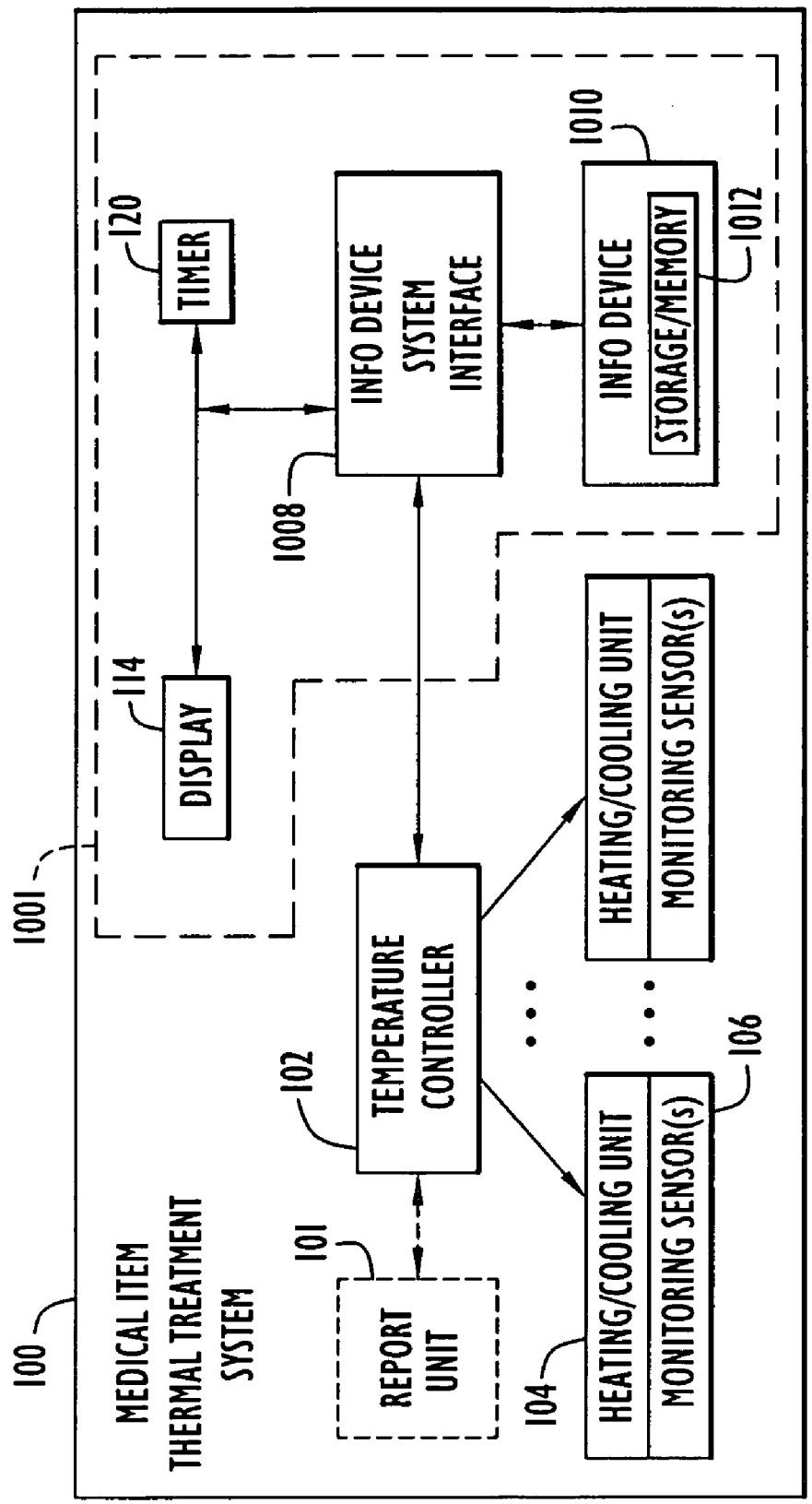
FIG. 13 is a block diagram of the usage control unit within the system of FIG. 10 to control system usage according to the present invention.

Usage control unit 1001 enables control of thermal treatment system use. Referring to FIG. 13, usage control unit 1001 includes an information device system interface 1008, an information device 1010 with storage or memory 1012, display 114 and/or timer 120.

Information device 1010 is preferably in the form of a chip or integrated circuit, but may be implemented by any type of device including a memory or storage (e.g., a microprocessor with memory, a chip, a floppy, magnetic or optical disk, CD-ROM, USB disk, smart card, etc.). The information device (e.g., chip) is typically provided to a user by a system service provider for installation in the thermal treatment system. Basically, the user plugs the information device into a receptacle on or within the system to couple the information device to system interface 1008. However, the coupling between the system interface and information device may be accomplished in any fashion (e.g., direct connection, infrared, RF transmission, cellular, Bluetooth, etc.). The system interface collects information from temperature controller 102 and/or monitoring sensors 106 during system operation and stores the collected information on information device 1010, preferably in storage device or memory 1012. The system interface may be implemented by any conventional or other device (e.g., microprocessor, controller, processing system, chip, circuitry, read/write unit, etc.) capable of collecting information and transferring data with information device 1010 and/or storage 1012.

The system interface is preferably disposed within the thermal treatment system; however, the interface may be disposed external of the thermal treatment system and coupled to the system via any desired medium (e.g., cable, wireless, etc.). The system interface may further maintain the date, elapsed heating/cooling time and/or occurrence time of an event or condition (e.g., the time when medical items are inserted and/or removed from the system, etc.).

The system interface may measure the elapsed time or record an occurrence time based on signals received from the temperature controller, monitoring sensors and/or system interface input devices. For example, the system interface may initiate measurement of a time interval in response to the temperature controller indicating enablement of heating/cooling units 104, and may store the elapsed and/or occurrence time in response to any condition (e.g., when solution or other item is removed). The system interface may further measure elapsed time or record elapsed and/or occurrence time in response to medical personnel manually entering information on the system interface input devices (e.g., start and stop keys). Alternatively, timer 120 may maintain elapsed time and provide timing information to the system interface and/or display.

The system interface collects the appropriate information and arranges the information for storage in memory 1012. The collected information may be arranged in any fashion and include any desired information. The system interface may collect and store a wide variety of information in storage 1012 related to the use of the thermal treatment system and the warming/cooling of individual medical items. For example, information pertaining to each medical item may be individually recorded and include: the date/time that a medical item was placed into/removed from the medical item warming/cooling system, the temperature of the medical item upon being placed into/removed from the medical item warming/cooling system, the temperature of the medical item at specific points in time while stored in the medical item warming/cooling system, start date and time that the medical item began to be heated/cooled, the length of time that the medical item was heated/cooled, the temperature that the medical item was heated/cooled to during the heating/cooling cycle and/or the amount of solution or other item residing, placed in or removed from the system.

The system interface may also store related information in memory 1012, such as patient information (e.g., name, identification number and/or the other patient information described above), thermal treatment system information (e.g., type, identification or serial number, etc.), user information (e.g., access or account identification or code, passwords, etc.), facility information (e.g., name, location and/or the other patient information described above), doctor information, the type of procedure, the solution information described above, the type of solution or other item being heated/cooled, the amount or quantity of fluid or other item being heated/cooled (e.g., fluid (or other item) level, volume or weight), the flow rate of fluid that is being heated/cooled, the pressure of fluid flow as the fluid is heated/cooled and any other desired information. The thermal treatment system may employ any type of sensors or sensing devices (e.g., temperature sensors, presence sensors, weight sensors, volume sensors, pressure sensors, flow sensors, fluid sensors, fluid level sensors, etc.) to measure and provide any desired information to the system interface for inclusion on information device 1010. The related information (e.g., user, system, facility, patient and/or doctor information, etc.) may be pre-stored on the information device and/or entered by a user via system or interface input devices (e.g., keypad, etc.). The recordation or collection of information by the system interface may occur automatically or via user entered information (e.g., start, stop and/or record keys) as described above. In this manner, storage 1012 is used to document use of the medical item thermal treatment system with recorded log entries. Logged event data may be user defined and/or pre-configured and may be generated in accordance with a periodic schedule and/or in response to a wide variety of events.

Generally, the information stored by the system interface in storage 1012 depends upon the particular type of thermal treatment system and corresponding sensors employed. For example, information collected and stored for IV solution warming (e.g., FIGS. 18, 21, 22, 27A and 30) or open basin (e.g., FIG. 20) type systems may include the temperature of solution or solution containers measured at any desired time interval (e.g., fifteen minutes, two minutes, one minute, etc.). Alternatively, the information stored for an open basin type system (e.g., FIG. 20) may include the time and temperature of solution when the solution is removed or scooped from the basin. The stored information may further indicate the amount of solution residing, placed in and/or removed or scooped from the basin.

The stored information may be retrieved or downloaded from information device 1010 and printed to generate a hardcopy report of thermal treatment system activity as described below. The report preferably becomes the permanent record of the thermal treatment system for later review. Further, the information from storage 1012 may be uploaded to one or more other storage devices as part of a permanent archive.

System interface 1008 may further retrieve usage and control parameters from memory 1012 and coordinate with temperature controller 102 to control operation of medical item thermal treatment system 100 in accordance with the retrieved parameters. The usage and control parameters are typically stored on information device 1010 by the service provider and may include: a calendar/time period during which the medical item thermal treatment system is authorized for use; a number of warming/cooling cycles for which the medical item thermal treatment system is authorized for use; a number of medical items for which the medical item thermal treatment system is authorized for use; type of use (e.g., heating, cooling, heating and cooling, etc.); a user access code; type of medical item accepted; a desired temperature for medical items; a maximum duration that a medical item (e.g., IV solution , blood, etc.) is allowed to remain in the thermal treatment system; time and/or temperature thresholds to be used in controlling alarms; log event definitions; timeouts; timer periods; various threshold values; log messages; storage destinations; etc.

The usage parameters enable a user to lease or rent use of the thermal treatment system based on various metrics (e.g., quantity of heating/cooling cycles, quantity of blocks or intervals of time, quantity of medical items, etc.). For example, usage parameters retrieved from storage 1012 may enable use of a medical item thermal treatment system for a specific number of warming/cooling thermal treatment cycles or for a particular time duration. Prior to initiating an activity (e.g., a heating/cooling cycle for a medical item), temperature controller 102 communicates with system interface 1008 to request authorization to initiate the activity. The authorization request typically includes a description of the type of activity (e.g., a heating/cooling cycle) and other relevant information (e.g., the heating/cooling unit to be used) for which verification of authorized use is requested. Upon receipt of the authorization request, system interface 1008 checks usage parameters stored in storage 1012 to determine whether the requested activity can be performed. If the usage parameters indicate the requested activity may be performed (e.g., sufficient quantity of cycles or time intervals exist), system interface 1008 enables temperature controller 102 to perform the activity (e.g., provides control signals to enable the temperature controller). Otherwise, if the usage parameters indicate the requested activity may not be performed, system interface 1008 disables temperature controller 102 (e.g., provides control signals to disable the temperature controller).

The usage parameters are updated in accordance with system use to control usage of the system. For example, the quantity of cycles or time interval stored on the information device may be updated (e.g., incremented or decremented) to indicate remaining system usage enabled by the information device. The system typically includes a display 114 coupled to the system interface that displays the remaining amount of system usage indicated by the usage parameters stored on the information device (e.g., remaining time or quantity of cycles). Upon exhausting the amount of use authorized by the usage parameters, the display notifies an operator that a new information device (e.g., chip) is needed. This may be accomplished by audio and/or visual indicators (not shown). The user orders a new information device from the service provider and removes the current information device for forwarding to the service provider. The data stored on the information device is retrieved and processed by the service provider to generate reports of system activity for the user (e.g., in various forms, such as hardcopy, e-mail, storage media (e.g., CD-ROM, floppy, etc.), fax, etc.). The retrieved information may also be stored for later retrieval. The information device may be re-programmed by the service provider to enable use of a thermal treatment system in accordance with the revised usage and control parameters on the information device as described above In operation, a service provider provides a user with information device 1010, preferably in the form of a chip. The information device (e.g., chip) is pre-programmed with usage and/or control parameters to control operation and usage of the thermal treatment system as described above. The user installs the information device on or in the thermal treatment system, where the information device is coupled to system interface 1008. Medical items are inserted into the thermal treatment system, where the user operates the system to thermally treat the items. The system interface retrieves the appropriate parameters from the information device and controls the temperature controller accordingly as described above. The remaining usage authorized by the information device is typically displayed on display 114 as described above.

During thermal treatment of the items, the usage parameters and display are updated. Further, system interface 1008 collects various information from temperature controller 102 and/or sensors 106 and stores this information on information device 1010. When sufficient information has been stored on information device 1010 or other condition occurs (e.g., expiration of usage, completion of system activity, etc.), the information device is removed from the system and forwarded to the service provider. The service provider retrieves and processes the collected information to generate reports for the user and re-programs the information device (e.g., revises the usage parameters) for additional use as described above. Alternatively, collected information may be formed into reports (e.g., FIGS. 12A-12I) by report unit 101 as described above, where the reports or information can be transmitted to internal printer 110, display 114 or to a local or remote external device (e.g., printer, display, database, medical item, etc.) as described above.

Figure 14:
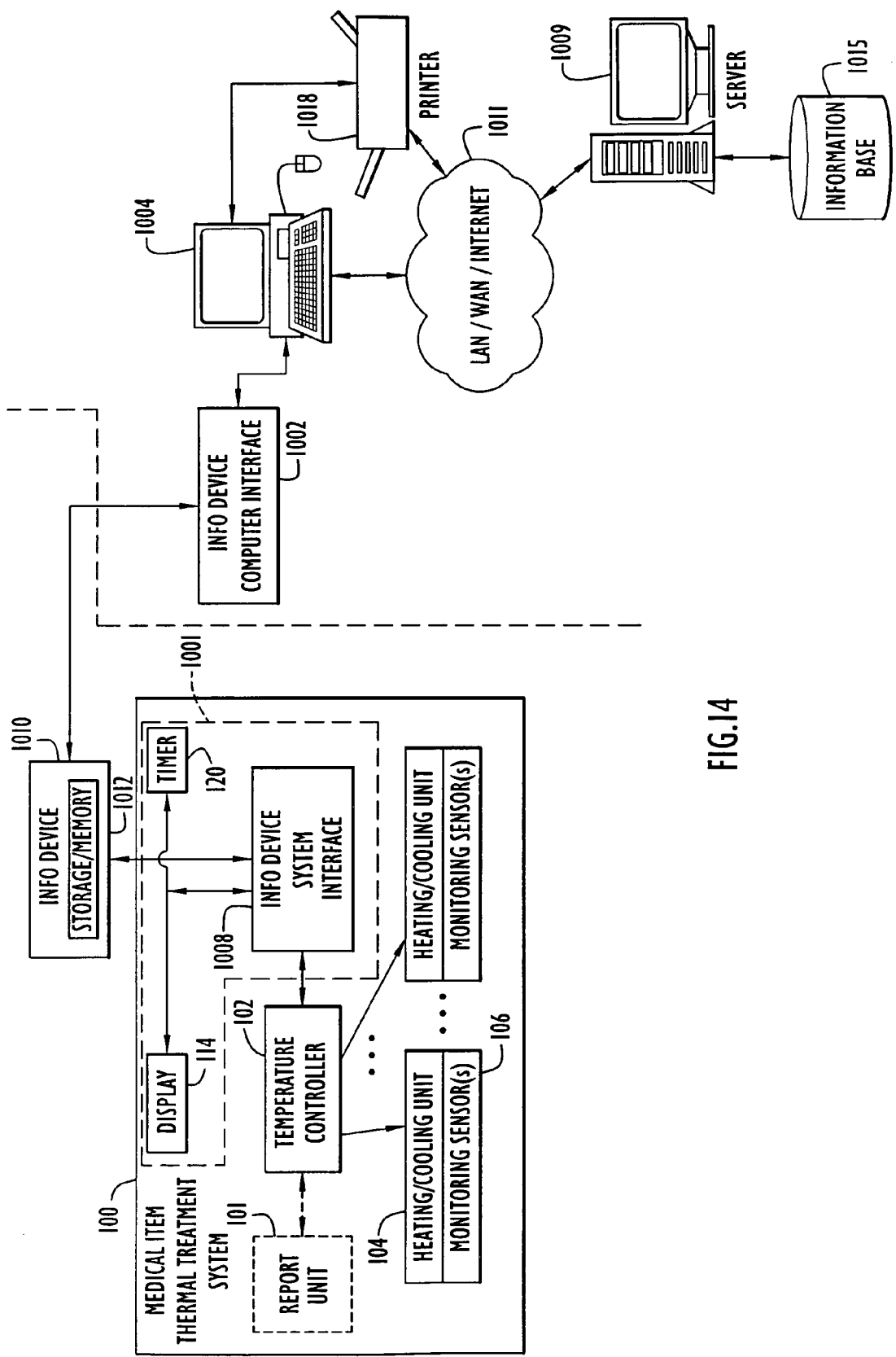
FIG. 14 is a diagrammatic illustration of an alternative embodiment of the usage control unit of FIG. 13 with a computer system to access monitored thermal treatment system information according to the present invention.

An alternative embodiment of usage control unit 1001 employing a computer system to access collected information on the information device is illustrated in FIG. 14.

Specifically, usage control unit 1001 is substantially similar to the unit described above and includes information device system interface 1008, display 114 and/or timer 120. Information device 1010 is in the form of a "smart" card and includes storage 1012. The card typically includes a plastic or paper substrate that houses storage 1012 and accompanying components (e.g., processor, circuitry, etc.). System interface 1008 is substantially similar to the system interface described above and transfers information with information device 1010. The information device (e.g., card) is sent to a user, preferably once, by a service provider with usage and control parameters stored thereon. The information device is received by the thermal treatment system and coupled to the system interface as described above, where the system functions as described above to collect information and store the information on information device 1010. Further, the system interface controls operation and use of the system in accordance with the usage and control parameters as described above.

When sufficient information has been stored on information device 1010 during system use or other condition occurs (e.g., expiration of usage, completion of system activity, etc.), information device 1010 is removed from system 100 to retrieve and process the collected information stored thereon. The stored information may be retrieved by a workstation or computer system 1004. A computer interface 1002 is coupled to computer system 1004 and receives or interfaces information device 1010. The computer interface may be disposed within or be external of the computer system. Interface 1002 is substantially similar to system interface 1008 and transfers information with information device 1010. The computer system retrieves the collected information from the information device (e.g., card) via interface 1002 and processes the information to generate reports. A user typically communicates by telephone (or other manner) with the service provider to ascertain a password to enable retrieval of the stored information by the computer system. Basically, the computer system may provide a user interface to enable a user to enter a password and then retrieve the information. A printer 1018 may be connected directly to computer system 1004 or be accessible via a network 1011 (e.g., LAN/WAN/Internet, etc.) to print the generated reports. Further, the password may enable the computer system to replenish the card (e.g., revise the usage parameters) to facilitate further use of a thermal treatment system. In other words, the computer system and computer interface may reprogram information device 1010 with the next password and other information for subsequent use.

Computer system 1004 may further be in communication with a remote server computer system 1009 via network 1011 (e.g., LAN/WAN/Internet, etc.). The server system is coupled to an information base 1015. In this case, information device 1010 is removed from system 100 and inserted into or coupled to computer interface 1002 as described above. Information stored on the information device (e.g., card) may be retrieved by computer system 1004 as described above and transferred to remote server system 1009 via network 1011 for storage in information base 1015. A user may visit a specific or service provider web site via computer system 1004 to download information from the information device to the server system for generation of reports and/or storage at the service provider or a user secure web site for later processing. The reports may be generated via the server system or web site and printed by printer 1018 that may be coupled to computer system 1004 and/or the network. Information device 1010 may be reprogrammed by computer interface 1002 and computer system 1004 in accordance with the server system or web site to facilitate additional use of a thermal treatment system (e.g., usage and/or control parameters may be updated) as described above. The user may receive a bill for the additional usage from the service provider.

Once the user completes the desired actions via computer system 1004, information device 1010 is removed from interface 1002 and received by system 100. System interface 1008 reads the usage and/or control parameters to control use and operation of the thermal treatment system as described above.

Figure 15:
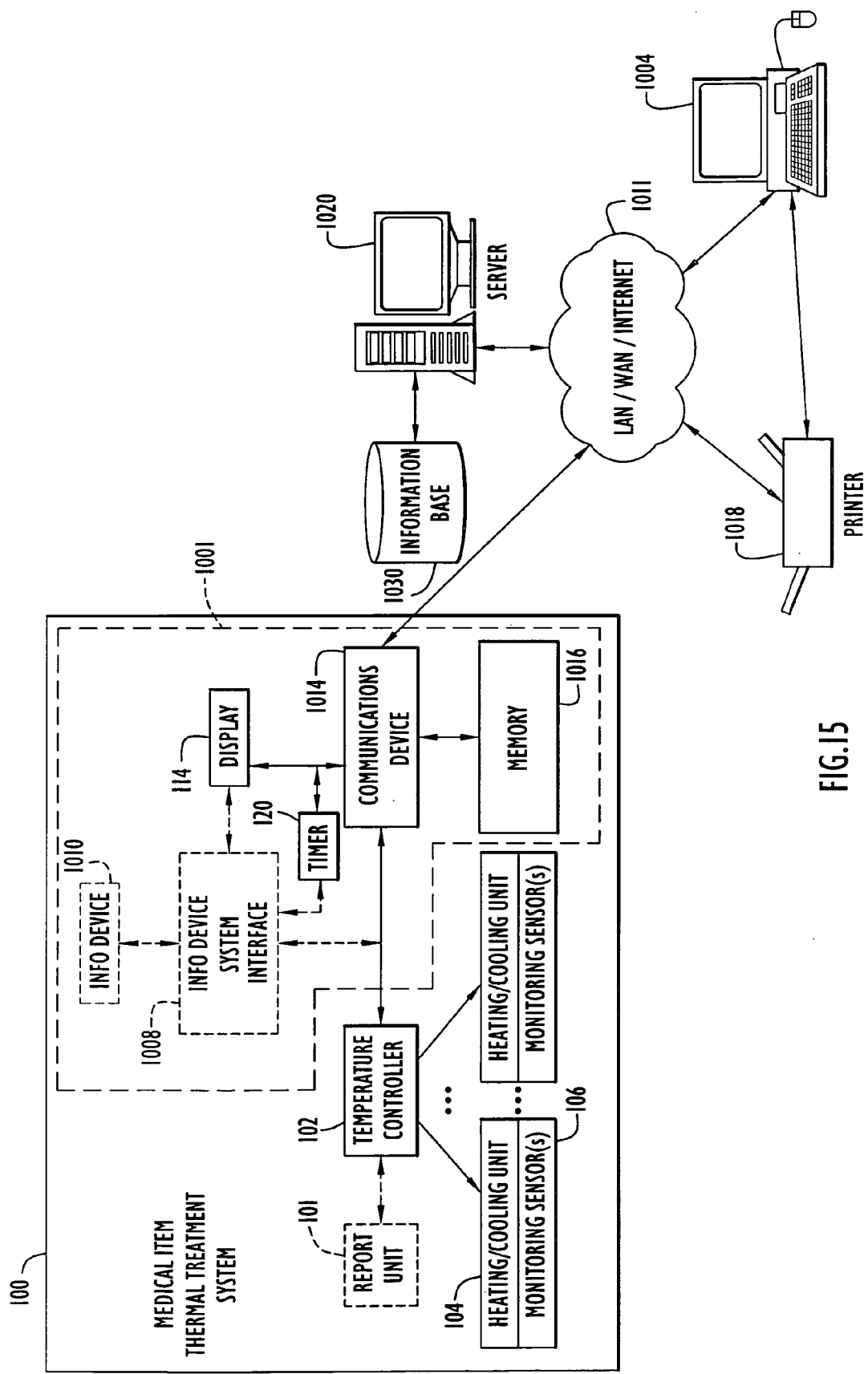
FIG. 15 is a diagrammatic illustration of yet another embodiment of the usage control unit of FIG. 13 in communication with storage and monitoring devices via a network according to the present invention.

Yet another embodiment of usage control unit 1001 in communication with a network is illustrated in FIG. 15. Specifically, usage control unit 1001 includes display 114, a communications device 1014 and/or timer 120. The communications device is in communication with a network 1011 (e.g., LAN/WAN/Internet, etc.) and coupled to temperature controller 102, display 114 and/or timer 120. The communications device may be implemented by any conventional or other processing and/or communications devices (e.g., router, modem, processing system, microprocessor, controller, etc.) and basically performs the functions substantially similar to those performed by system interface 1008 described above of collecting information pertaining to system activity from the temperature controller and/or sensors and monitoring and controlling system use based on control and usage parameters. The communications device further transfers that information over the network. The thermal treatment system operates as described above to thermally treat medical items and collect information pertaining to system activity and usage. Communications device 1014 may store collected information and/or parameters in a memory 1016, where the collected information is transmitted over network 1011 to a server computer system 1020 for storage in an associated information base 1030. The server system is coupled to network 1011 and basically serves as a host system to collect information from the thermal treatment system and store that information in information base 1030.

The server system further provides the thermal treatment system with usage and control parameters to enable the communications device to monitor and control system use as described above. A user may access the server system via a workstation or computer system 1004 coupled to network 1011 in order to retrieve and process the collected information to generate reports. The server system typically provides a user interface, preferably in the form of a service provider web site, to facilitate these user functions. The reports may be printed via a printer 1018 coupled to network 1011 or computer system 1004. A service provider may control access to the web site and/or system data based on various techniques (e.g., passwords, subscriptions, accounts, etc.). Thus, the thermal treatment system may monitor and control use via server system 1020 and information base 1030 without use of an information device. Alternatively, the usage control unit may further include system interface 1008 and information device 1010, each as described above, where the communications device is further coupled to the system interface and serves to transfer information between that interface and the network. The information device may contain various information (e.g., user or system identification, usage information, etc.) and receive collected information as described above. The information stored on the information device may be transferred to the server system to enable a user to retrieve information via the web site. In addition, the control and usage parameters stored on the information device may be revised (e.g., replenish usage, etc.) by the system interface in accordance with actions by a user on the web site. The information store and information device may contain or receive any information in any desired combination.

The medical item thermal treatment system may transfer information to server system 1020 for storage within information base 1030 in real-time, as events occur. This allows a user at workstation 1004 to monitor the status of one or more medical item thermal treatment systems and the status of medical items undergoing a warming/cooling cycle via displays or reports generated from real-time and/or historic data contained within the information base. For example, a user within an operating room, or remote to an operating room, can monitor one or more medical item thermal treatment systems. Information within the information base can be queried using information base query techniques or displayed via a dynamically updated user interface viewed at workstation 1004 that presents the user with a selected view of one or more medical item thermal treatment systems. Visible and/or audible alarms may alert the user to conditions that exceed established control parameters or prescribed requirements. By way of example, if a medical item solution exceeds a predetermined temperature, or has maintained a temperature for a period of time that exceeds a user configurable maximum value, the user can be alerted in real-time as the conditions occur and take corrective action, as necessary.

Further, usage and control parameters may be updated within the information base by a user, via the web site, and immediately downloaded to the affected medical item thermal treatment system in real-time, or upon occurrence of a scheduled or event based trigger. For example, a user can review the use remaining on one or more medical item thermal treatment systems 100, and authorize additional blocks of use, as necessary. Use can be authorized using a service provider dynamic user interface or web site displayed at workstation 1004. Payment for additional use can be coordinated directly with the service provider, by phone, or via a conventional debit/credit based electronic transaction.

Figure 16:
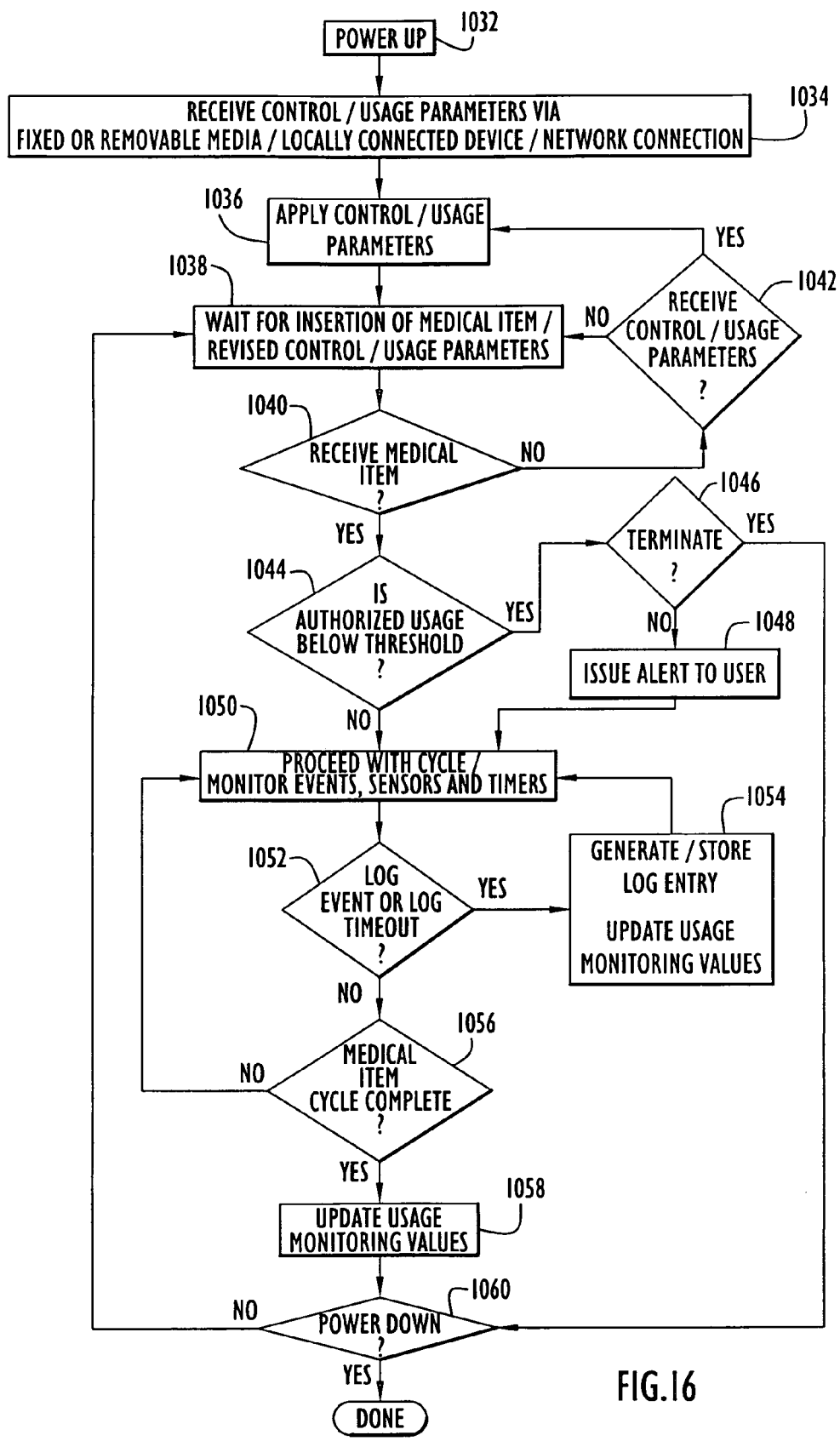
FIG. 16 is a procedural flow chart illustrating the manner in which a medical item thermal treatment system thermally treats a medical item and monitors and controls system use according to the present invention.

The manner in which a medical item thermal treatment system monitors and controls system use or activities according to the present invention is illustrated in FIG. 16. Specifically, thermal treatment system 100 (FIGS. 13-15) is enabled at step 1032 and receives, at step 1034, usage and control parameters (e.g., log event definitions, timeouts, timer periods, initial usage values, threshold values, log messages, storage destinations, etc.) from a source (e.g., information device 1010, a server system, etc.) as described above. The thermal treatment system applies the received parameters, at step 1036, to monitor and control system use. Next, the medical item thermal treatment system waits, at step 1038, for insertion of a medical item or receipt of revised parameters. If a medical item is received, at step 1040, and the system, at step 1044, determines that usage remains available, the thermal treatment system proceeds, at step 1050, to initiate a warming/cooling cycle based upon the operational control and/or usage parameters received in step 1034.

If, at step 1040, a medical item is not received and the system determines, at step 1042, that revised control and/or usage parameters are received, operation returns to step 1036, where the revised parameters are applied.

If, at step 1044, the usage parameter values have fallen below a predetermined threshold, operations can be terminated, at step 1046, or an alert can be generated for the user and logged, at step 1048, prior to proceeding with a warming/cooling cycle, at step 1050.

Once the thermal treatment system proceeds with a warming/cooling cycle for a medical item, at step 1050, the thermal treatment system monitors heating/cooling events, sensor values and/or system timers. Upon occurrence of a defined event or a predetermined timeout period, at step 1052, the thermal treatment system, at step 1054, generates and stores a log entry and/or updates stored values used to monitor and track usage and other system status values. Upon handling the log event, the thermal treatment system proceeds with the warming/cooling cycle, at step 1050, and continues to monitor/log events, at steps 1052, 1054 until the medical item warming/cooling cycle is complete, at step 1056. At step 1058, the medical item thermal treatment system updates usage parameter values (e.g., remaining usage time, warming/cooling cycle counters, etc.). If a power down of the system is initiated, at step 1060, operations cease; otherwise, operations proceed to step 1038, and the system waits for insertion of a new medical item or revised parameters as described above.

Figure 17:
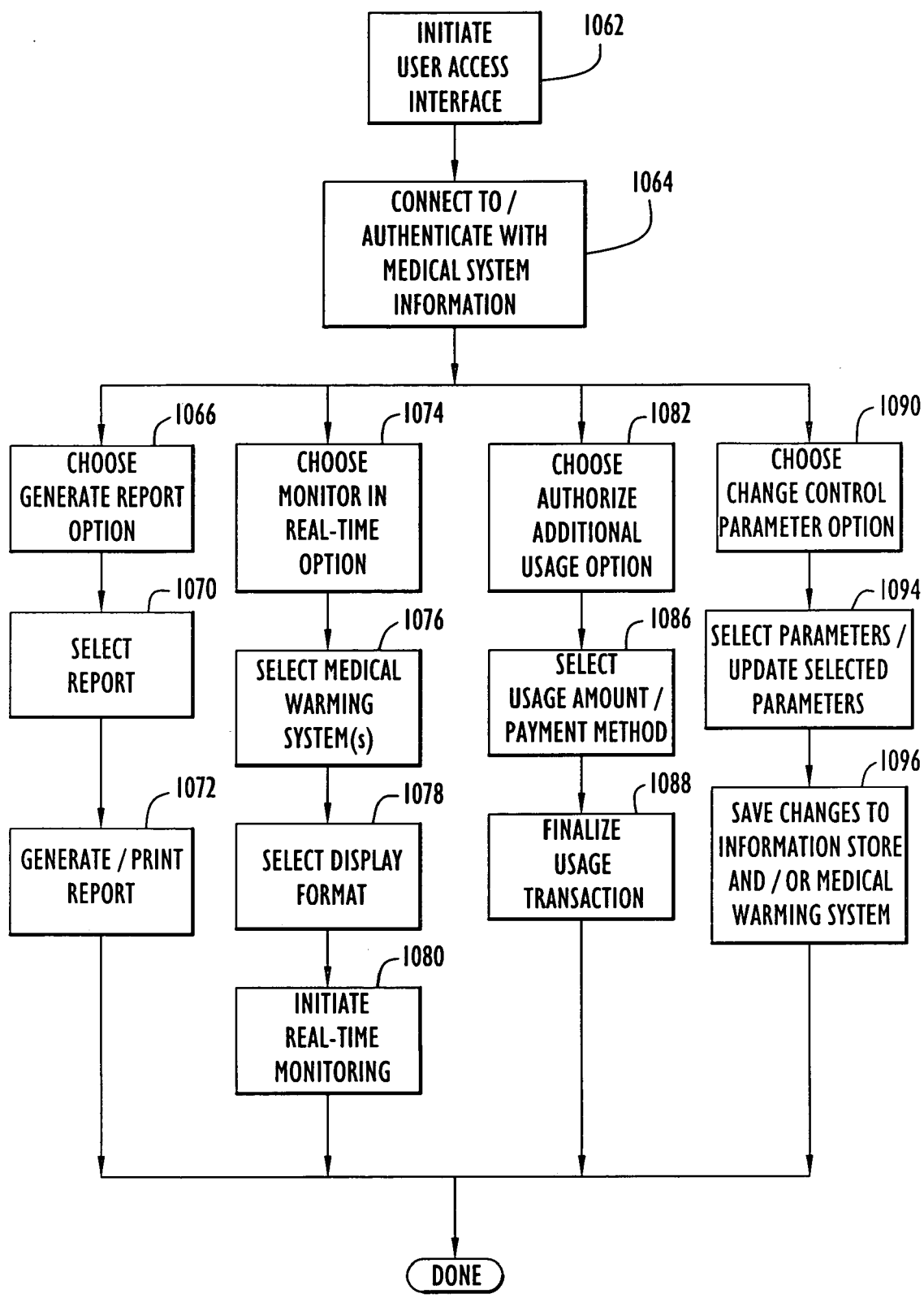
FIG. 17 is a procedural flow chart illustrating the manner in which the present invention enables a user to monitor and control thermal treatment system use.

The manner in which monitoring and control of system use is accomplished via a local or remote computer system according to the present invention is illustrated, by way of example only, in FIG. 17. Specifically, workstation or computer system 1004 (FIGS. 14-15) or any other network or locally connected device initiates, at step 1062, a user interface and, at step 1064, establishes a connection with medical item thermal treatment system information base 1004, 1030 or information device 1010 provided by the user as described above.

Once a connection is established, a user can choose, at step 1066, to generate a display or report that contains information about system use. A user may select one or more medical item thermal treatment systems for which information is to be included in the display or report when accessing the information store. At step 1070, the user selects the display or report to be generated. The display or report generated can be displayed and/or printed, at step 1072, to one or more local or network connected display devices and/or printers.

If one or more medical item thermal treatment systems support a real-time network interface with the medical item thermal treatment system information base, a user can request real-time monitoring of events and/or monitored parameters. In particular, the user chooses, at step 1074, to monitor operations in real time, and selects, at step 1076, one or more medical item thermal treatment systems for which information is to be included in the real-time display. Next, the user selects, at step 1078, a display format that supports the information the user is interested in monitoring and initiates, at step 1080, the real-time monitoring process. As a result, the selected display is presented and updated in real-time as relevant information changes within the medical item thermal treatment system information base. The display may be printed to provide reports of conditions at various times.

A user can select, at step 1082, to authorize additional medical item thermal treatment system usage. The user may select one or more medical item thermal treatment system(s) to which usage is to be added when accessing the information base. At step 1086, the user selects the usage-policy/usage-amount to be added to the medical item thermal treatment system based upon the information displayed, and a payment method, such as a debit or credit account. The user finalizes the usage transaction, at step 1088, upon which authorized use parameters in the information base or stored on information device 1010 are updated.

A user can select, at step 1090, to change one or more control parameters. The user may select one or more medical item thermal treatment systems to which control parameters are to be updated when accessing information store 1030. At step 1094, the user selects and updates the associated user controlled parameters. The user finalizes, at step 1096, the change control parameters transaction, thereby updating control parameters in the information base and/or information device. The control parameters can be used to define log events, log event messages, log event heartbeat timers, control point decisions, etc., depending upon the monitoring and control capabilities supported by the respective medical item thermal treatment systems as described above.

Figure 18:
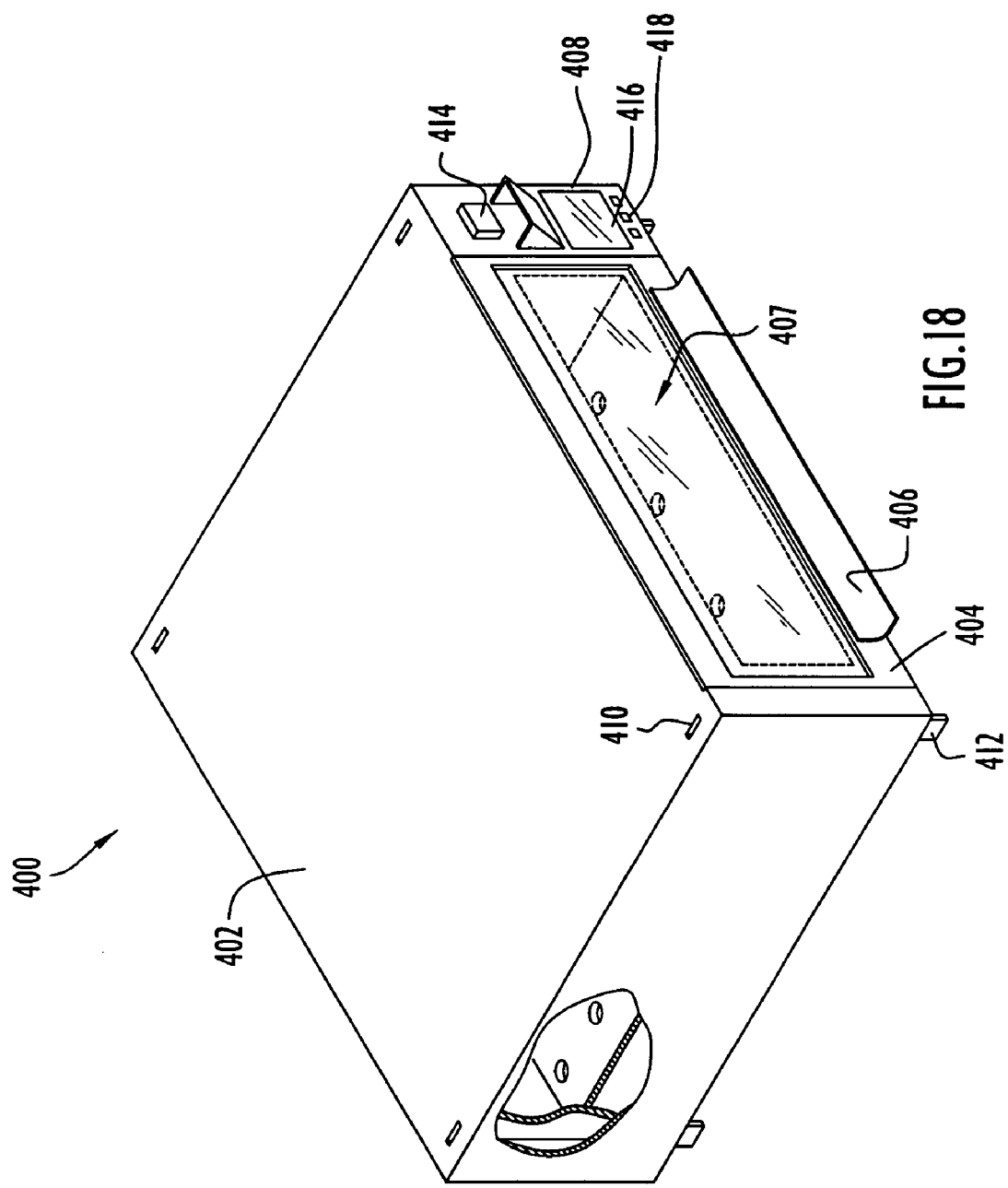
FIG. 18 is a view in perspective of an exemplary modular warmer unit according to the present invention.
Figure 19:
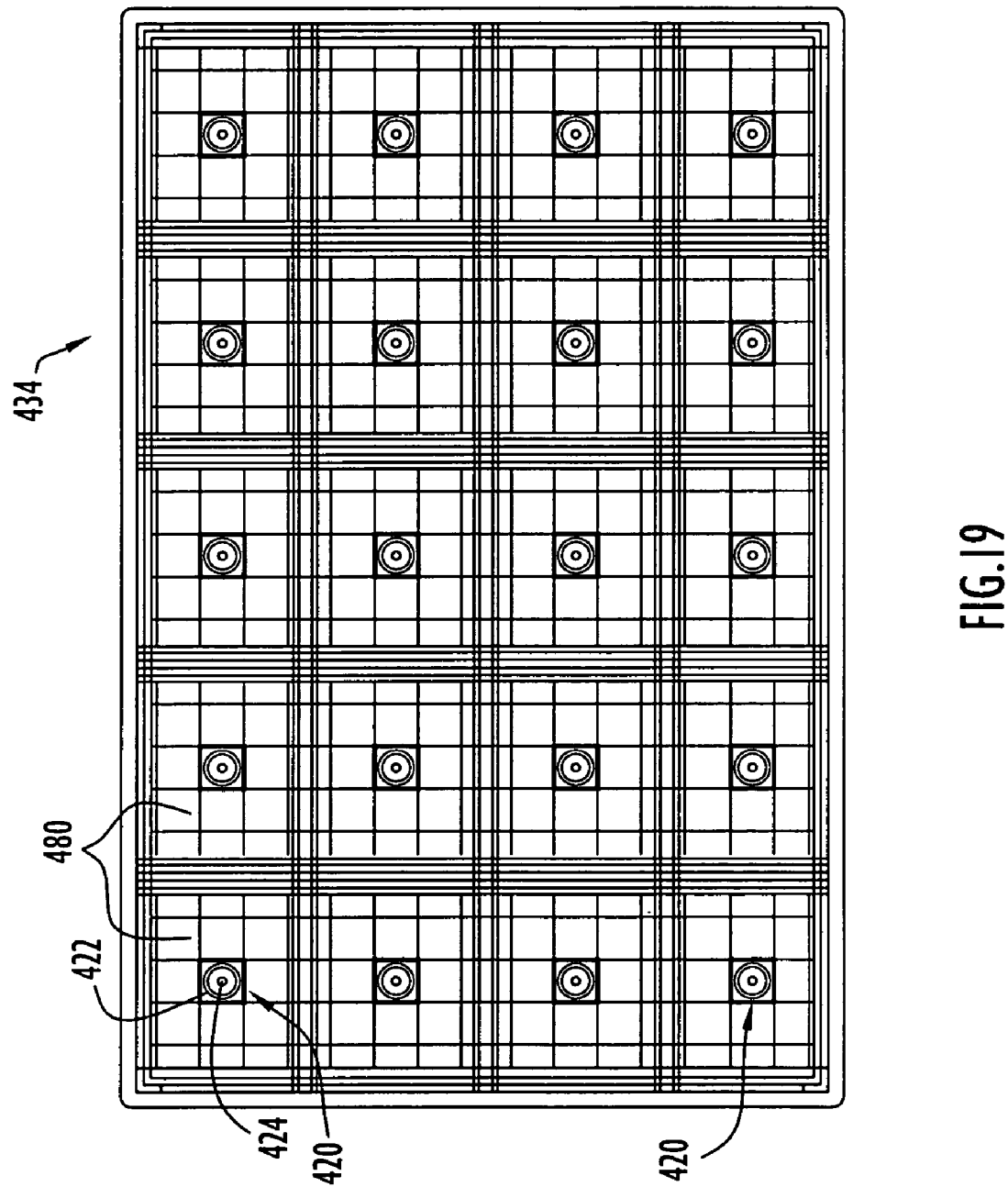
FIG. 19 is a top view in plan of a tray or drawer for the unit of FIG. 18 including individual monitoring assemblies and a configuration to enable storage of numerous medical solution containers in a generally upright position.

Thermal treatment system 100 (e.g., monitoring conditions, transmitting and/or printing information, etc.) may be in the form various thermal treatment systems for heating/cooling and/or delivering fluids (e.g., open basin warmer/cooler, IV bag or bottle warmer/cooler, irrigation bag or bottle warmer/cooler, IV fluid line warmer/cooler, irrigation fluid line warmer/cooler, a hand piece delivery warmer/cooler, an instrument and/or disposable fluid heating/cooling system (e.g., Hotline, Ranger or Cincinnati Sub Zero systems, etc.), etc.). By way of example only, a medical item warming/cooling system 400 with monitoring, transmission, printout and/or usage control capabilities is illustrated in FIGS. 18-19. The system is of the type disclosed in U.S. Pat. No. 6,660,974 (Faries, Jr. et al.). Specifically, medical item warming/cooling system 400 includes a housing 402, an access door 404 with a handle 406, a compartment 407 and a control panel area 408. The system may stack vertically upon other medical item systems using detents 410 in the top of housing 402 and protrusions 412, protruding from the bottom of housing 402 to align vertically stacked system units.

Control panel area 408 typically includes a power switch 414 and a display 416 with control buttons 418 used by a user to enter selections into the system. System operation is typically controlled by a temperature controller in accordance with a set point temperature entered by a user and temperatures measured by a temperature sensor as described above. The system typically employs heated air to heat medical items placed within compartment 407.

Solution bags (e.g., conventional solution bags or the solution bags described above) or other medical items are disposed within a drawer 434 (FIG. 19) for insertion into compartment 407. Drawer 434 includes a series of receptacles 480 each for receiving a corresponding medical item. The receptacles may include a series of monitoring assemblies 420 to monitor the temperature and residence time (e.g., amount of time an item resides within the warmer unit) of individual medical items heated within the warmer unit. Specifically, monitoring assemblies 420 are each mounted below the approximate center of a receptacle floor portion of a corresponding receptacle 480, where the monitoring assemblies may be mounted to the drawer via any suitable mounting devices (e.g., clamps, brackets, adhesives, etc.). The monitoring assemblies each include an item sensor or switch 422 to detect when a medical item is placed within a corresponding receptacle 480 and a temperature or other sensor 424 to directly measure the temperature or other conditions of the medical item within that receptacle.

The system includes a configuration similar to that described above for system 100 and may further include report unit 101 and/or usage control unit 1001 to generate, transmit and/or print reports and/or control system usage as described above for system 100. An interface 20 may be disposed in a receptacle in the form of a wireless transmitter/receiver (e.g., RF, infrared, etc.), bar code scanner or connector or port to communicate with the medical item and/or identify the medical item to the system for storage of monitored information as described above.

Figure 20:
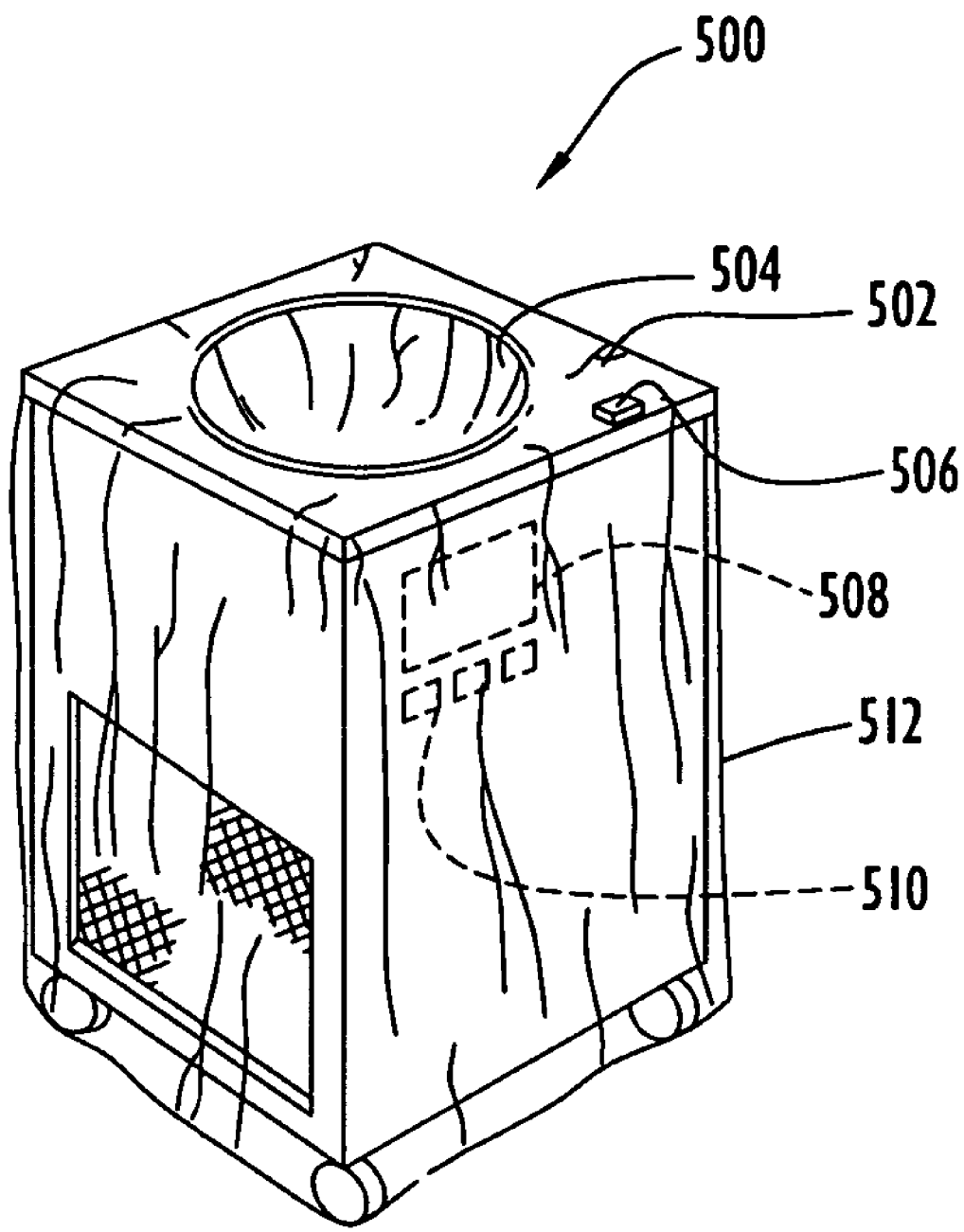
FIG. 20 is a view in perspective of an exemplary type of thermal treatment system for thermally treating and monitoring a medical solution within a basin according to the present invention.

Another exemplary thermal treatment system 500 with monitoring, transmission printout and/or usage control capabilities is illustrated in FIG. 20. The system is of the type disclosed in U.S. Pat. No. 6,371,121 (Faries, Jr. et al.). Specifically, system 500 includes a cabinet or system housing with a top surface 502 supporting a basin 504. System 500 is designed to be covered with a sterile drape 512 that envelopes the cabinet and basin surfaces, thereby creating a sterile field for warming and/or cooling sterile fluids. System 500 is further equipped with a power on/off button 506, an optional display 508 with input/output control buttons 510 and a temperature controller to control system operation in accordance with a set point temperature entered by a user and a temperature measured by a temperature sensor as described above. The system includes a configuration similar to that described above for system 100 and may further include report unit 101 and/or usage control unit 1001 to generate, transmit and/or print reports and/or control system usage as described above for system 100.

Figure 21:
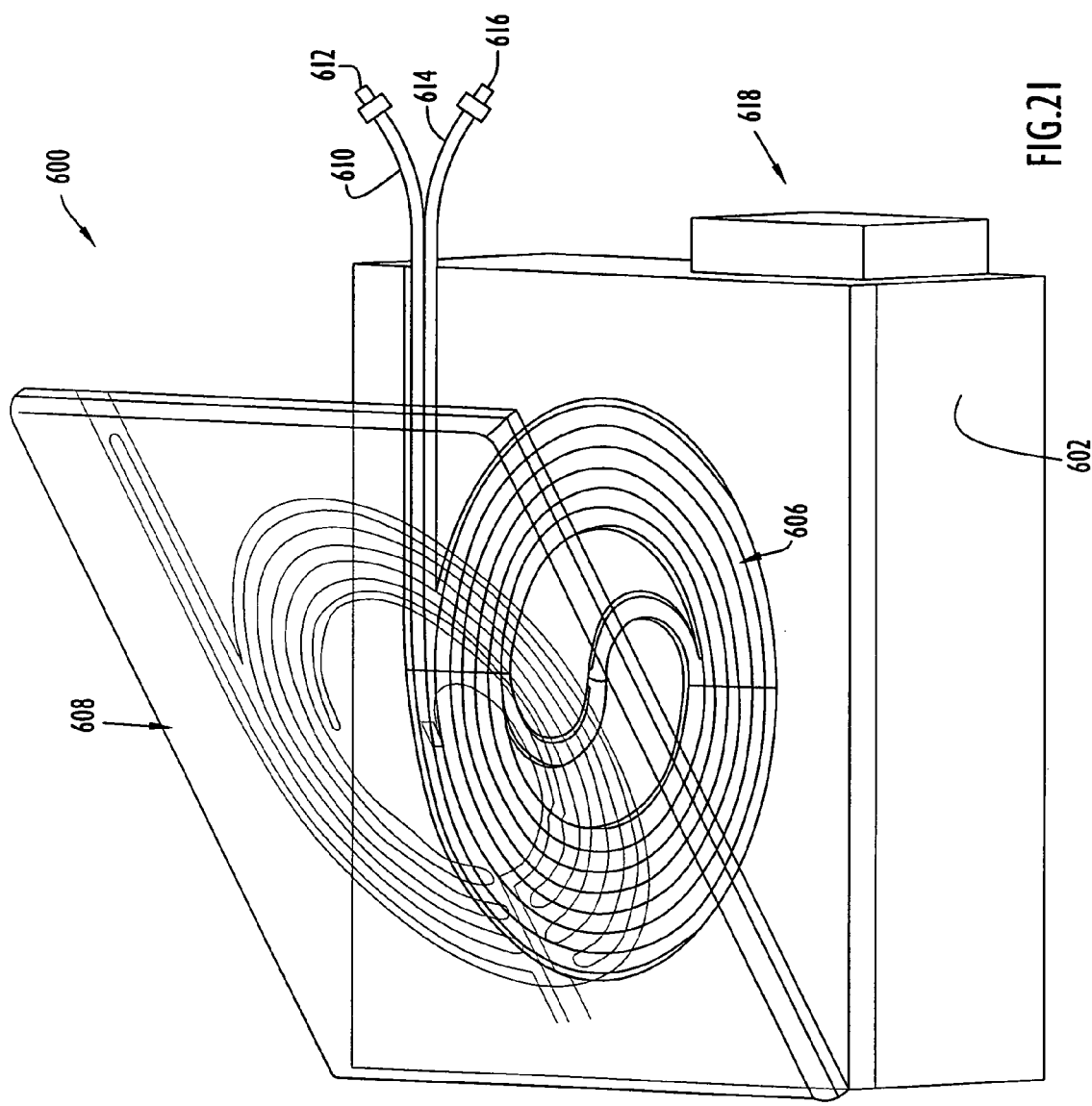
FIG. 21 is a view in perspective of an exemplary type of thermal treatment system for thermally treating and monitoring solution within an IV line according to the present invention.

Yet another exemplary warming/cooling system 600 for IV lines with monitoring, transmission, printout and/or usage control capabilities is illustrated in FIG. 21. The system is of the type disclosed in U.S. Patent Application Publication No. 2003/0114795 (Faries, Jr. et al.). Specifically, medical item warming/cooling system 600 includes a system base 602 that houses a heating element and corresponding temperature sensor (not shown). The base top surface receives a cassette of IV tubing 606. The cassette may include any of the devices or indicia (e.g., monitoring device, memory device, bar code, transponder, ink cells, etc.) described above for solution bag 2 to monitor compliance with prescribed requirements for the IV solution. Lid or cover 608 includes an additional heating element and closes upon the cassette loaded within system base 602, thereby substantially encasing sterile tubing 606. A first end 610 of sterile tubing 606 with connector 612 and a second end 614 of sterile tubing 606 with connector 616 protrude from medical item warming/cooling system 600 to connect to an IV line. A controller 618 includes a display and control input/output buttons to control operation of medical item warming/cooling system 600 in accordance with a set point temperature entered by a user and a temperature measured by the temperature sensor as described above. The system includes a configuration similar to that described above for system 100 and may further include report unit 101 and/or usage control unit 1001 to generate, transmit and/or print reports and/or control system usage as described above for system 100.

Figure 22:
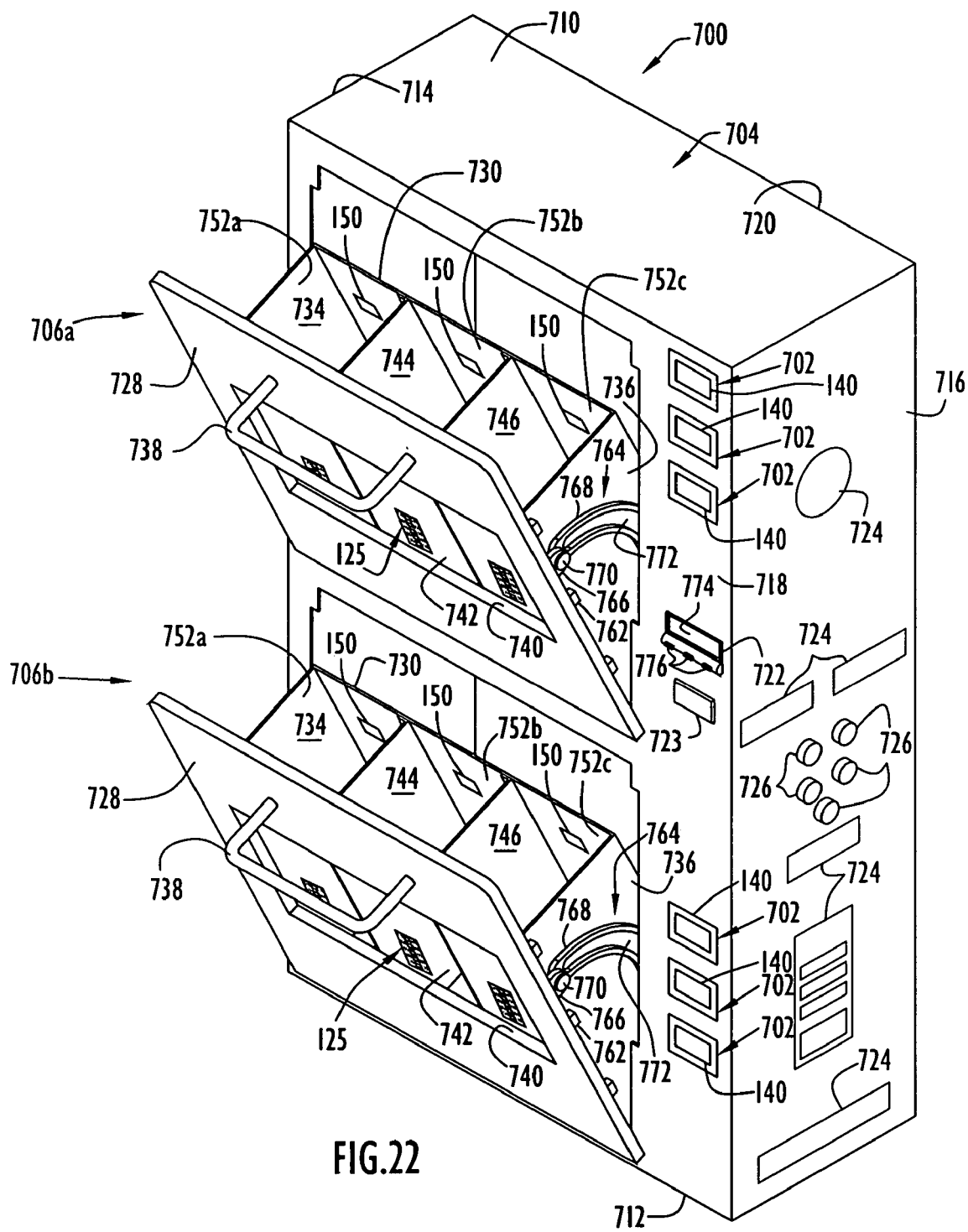
FIG. 22 is a view in perspective of a temperature control system for heating medical items and measuring and displaying residence time of those items within the system in accordance with the present invention.
Figure 23:
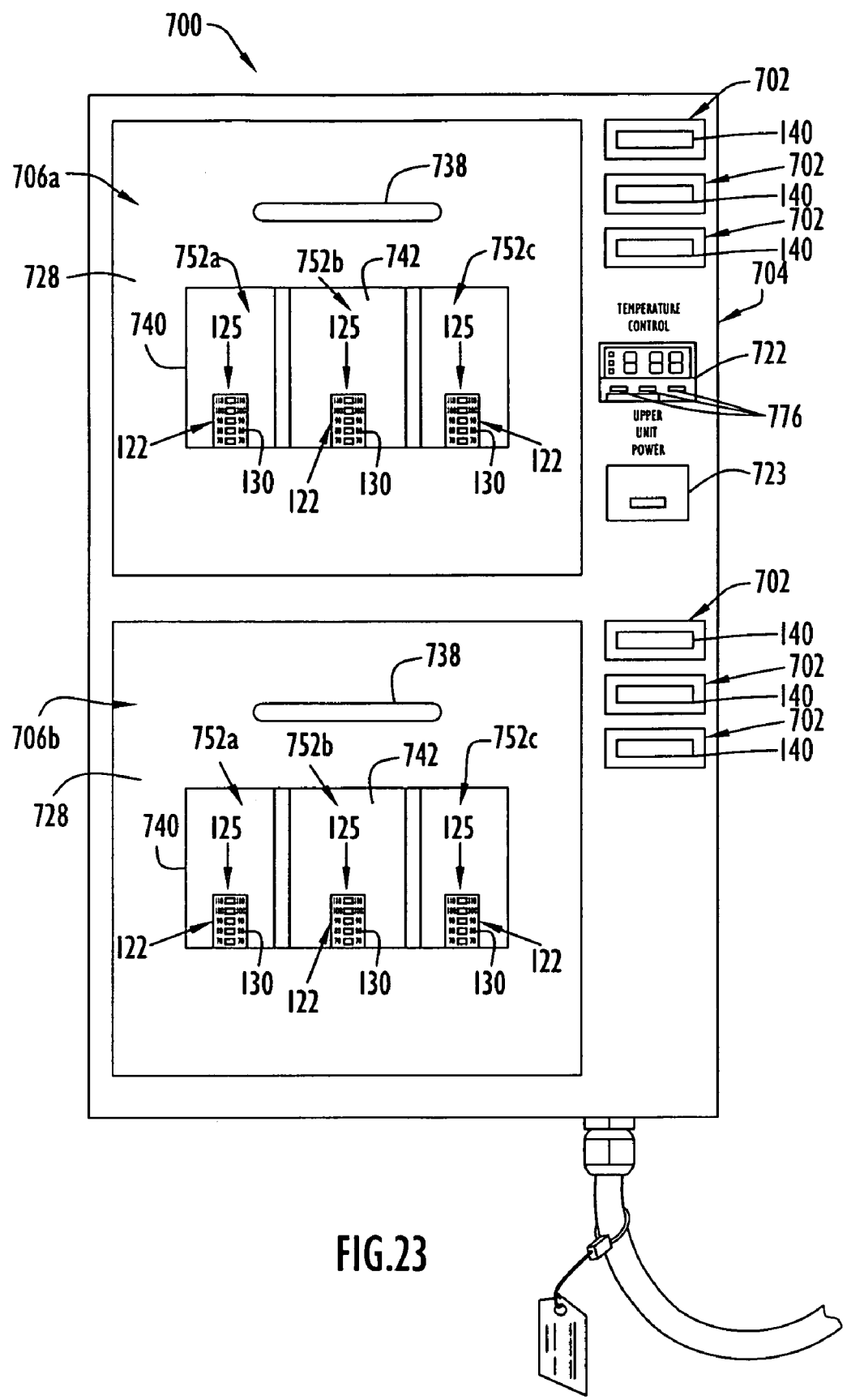
FIG. 23 is a front view in elevation of the system of FIG. 22.
Figure 24:
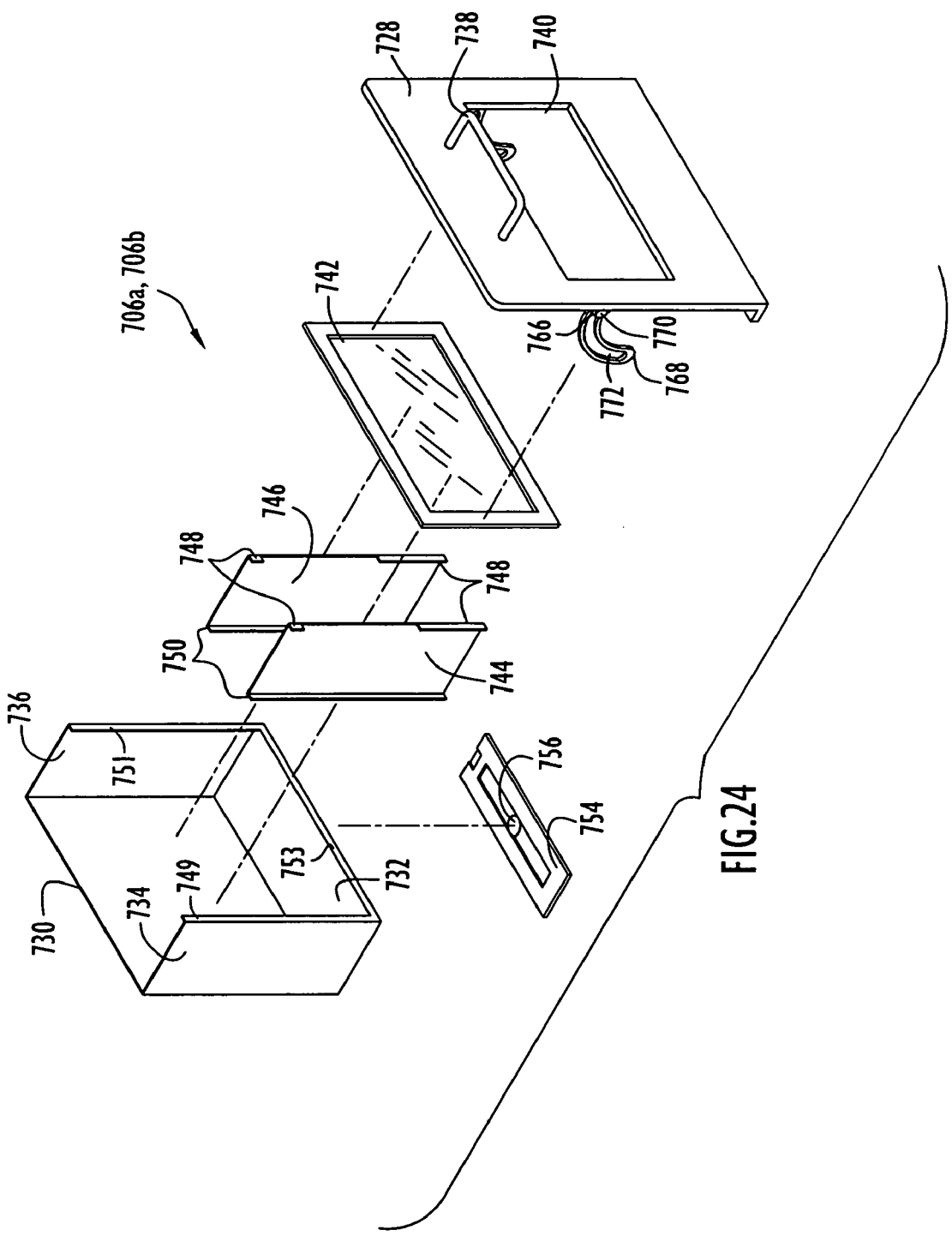
FIG. 24 is an exploded perspective view of a drawer of the system of FIG. 22.

A further temperature control system of the present invention for thermally treating and/or monitoring medical solution containers (e.g., bags or bottles containing saline or intravenous (IV) solutions, antibiotics or other drugs, blood, etc.) or other medical items (e.g., instruments, blankets, etc.) with direct measurement of medical item temperature and display of medical item residence time within the system is illustrated in FIGS. 22-24. Specifically, temperature control system 700 includes a cabinet or system housing 704 with substantially similar drawers 706a, 706b for enabling placement and removal of medical items, such as intravenous solution bags, within the system and a controller 722 for controlling heating of the drawers to maintain the bags at the same or different desired temperatures. Cabinet 704 is generally in the form of a rectangular box and includes top and bottom walls 710, 712, side walls 714, 716 and front and rear walls 718, 720. The cabinet walls are each substantially rectangular and collectively define a cabinet interior. Further, side wall 716 typically includes a series of labels 724, such as fuse warning labels and labels providing other information, and a plurality of fuse holders 726 for receiving fuses of the system control circuitry described below. The cabinet is typically constructed of electro-galvanized steel (e.g., eighteen gauge) or other suitably sturdy material, and may be of any size or shape.

Drawers 706*a*, 706*b* are generally disposed in vertical alignment in front wall 718 toward side wall 714, while controller 722 is disposed in front wall 718 adjacent drawer 706*a* and power switch 723 toward side wall 716. Controller 722 enables entry of a desired or set point temperature associated with each drawer and controls heating of intravenous solution bags residing within the drawers based on the associated desired temperatures as described below. Power switch 723 is generally disposed below controller 722 and enables power to the controller for heating intravenous solution bags disposed within the drawers. By way of example only, cabinet 704 includes two drawers, however, any quantity (e.g., at least one) of drawers, power switches, controllers and control circuitry may be utilized, while the cabinet components may be arranged in any fashion.

Drawers 706*a*, 706*b* each include a front wall or door 728, a rear wall 730, a bottom wall 732 and side walls 734, 736. The drawer walls are each substantially rectangular and collectively define a compartment or drawer interior having an open top portion for enabling placement and removal of intravenous solution bags within the drawers. The drawers may be of any size or shape, and the system may include any combination of drawers of different or substantially similar types.

Door 728 includes a handle 738 typically disposed toward the door upper portion, whereby the handle may be implemented by any conventional or other type of handle. Alternatively, the handle may be disposed on the door at any suitable location. Door 728 generally enables a corresponding drawer to pivot into and out of the cabinet as described below, and is typically constructed of electro-galvanized steel (e.g., sixteen gauge) or other suitably sturdy material. The door further includes a substantially rectangular opening 740 covered by a substantially transparent material 742, such as glass or plexiglass, to serve as a window to enable viewing of the intravenous solution bags and maintain heat within the cabinet. The door, opening and transparent material may be of any size or shape. Divider walls 744, 746 are disposed within each drawer interior to partition that interior into sub-compartments or bins 752*a*, 752*b*, 752*c*. In particular, divider walls 744, 746 (FIG. 24) extend from rear wall 730 substantially in parallel to, and include dimensions substantially the same as, side walls 734, 736. The front and rear edges of dividers 744, 746 are bent at an angle of approximately ninety degrees relative to the respective divider wall body portions, and extend transversely toward side wall 734 to form ledges 748, 750, respectively. Similarly, the front edges of side walls 734, 736 are bent at an angle of approximately ninety degrees relative to the respective side wall body portions, and extend transversely toward each other to form ledges 749, 751, respectively. Further, the front edge of bottom wall 732 is bent at an angle of approximately ninety degrees relative to the bottom wall body portion, and extends upward toward a drawer upper portion to form ledge 753. Ledges 750 enable the divider walls to interface rear wall 730, while ledges 748 include a recess or gap to permit the divider walls to engage and secure transparent material 742 within opening 740 of door 728. Moreover, ledges 748, 749, 751 and 753 enable the door to interface the drawer side, bottom and divider walls. Each drawer sub-compartment is typically configured to accommodate a single intravenous solution bag, and is defined by the drawer rear, bottom, side and divider walls. Specifically, sub-compartment 752*a* is defined between side wall 734 and divider wall 744, sub-compartment 752*b* is defined between divider walls 744, 746 and sub-compartment 752*c* is defined between divider wall 746 and side wall 736. The drawer side, rear, bottom and divider walls are typically constructed of copper or other suitable heat conducting material to conduct and evenly distribute heat to the intravenous solution bags disposed within the drawer as described below.

A heating element or pad 754 is typically disposed on the underside of each drawer bottom wall 732, whereby the heat applied by the heating pad is conducted by the drawer bottom, side, rear and divider walls to provide an even heat distribution to the intravenous solution bags residing in the sub-compartments of that drawer. In other words, each individual drawer sub-compartment includes bottom, side and rear walls that conduct and directly transmit heat from the heating pad to the intravenous solution bag contained in that sub-compartment, thereby preventing other intravenous solution bags residing in the cabinet from being affected by the applied heat. The application of heat from the sub-compartment walls provides a relatively uniform heat distribution and prevents the occurrence of certain intravenous solution bags (e.g., bags disposed near the heat source) attaining higher temperatures than the remaining bags (e.g., bags disposed at other locations within the cabinet) as is typically present in common single heat source systems. Alternatively, the heating pad may be disposed on the side or rear walls of each drawer. The heating pad is preferably configured to cover only a portion of a drawer bottom wall, but may include any type of configuration (e.g., strips, bars, segments, include various openings, etc.). A temperature sensor 756 is typically disposed on the underside of each drawer bottom wall 732 generally within the confines of the corresponding heating pad (e.g., the portion of the heating pad not covering the drawer bottom wall). The temperature sensor is preferably implemented by a conventional RTD temperature sensor and measures the temperature of the bottom wall of the corresponding drawer. However, the temperature sensor may be implemented by any conventional or other type of temperature sensor, and may be disposed at any suitable location on or within a drawer. The drawer may further include any type of sensors or sensing devices (e.g., temperature sensors, presence sensors, weight sensors, volume sensors, pressure sensors, flow sensors, fluid sensors, fluid level sensors, etc.) to measure and provide any desired information. The temperature measurement of sensor 756 is provided to the controller for control of the corresponding heating pad as described below.

Figure 25:
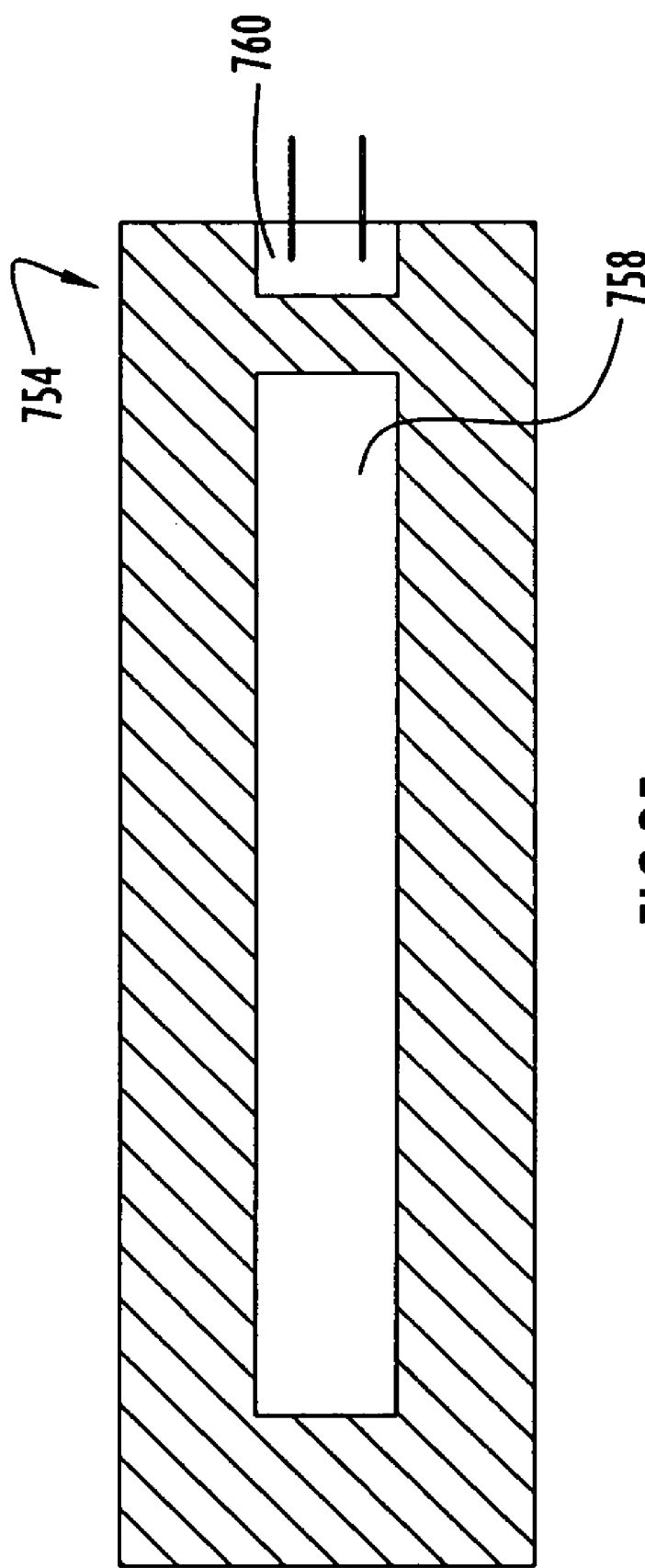
FIG. 25 is a view in elevation of an exemplary heating element of the system of FIG. 22.

An exemplary heating pad of the type employed by temperature control system 700 is illustrated in FIG. 25. Specifically, heating pad 754 is substantially rectangular and includes a substantially rectangular opening 758. A connector 760 is disposed along a heating pad shorter dimension edge to facilitate connections for the heating pad. The heating pad is preferably implemented by a conventional etched foil silicon rubber heater (e.g., forty-four watts, one-hundred twenty VAC) having an extra layer of silicon rubber on the adhesive side. The heating pad further includes a pressure sensitive adhesive for attachment to a drawer bottom wall. Temperature sensor 756 is typically disposed within opening 758 to measure the temperature of a corresponding drawer bottom wall as described above. The heating pad may be of any quantity (e.g., at least one), shape, or size, and may include any configuration that covers the entirety or a portion of a corresponding drawer bottom wall. In addition, the heating element or pad may be implemented by any conventional or other type of heater or heating element (e.g., heating coils) to heat the drawers.

Referring back to FIGS. 22-24, side walls 734, 736 of drawers 706*a*, 706*b* interface respective doors 728 via posts 762 to secure the drawers to the doors. Each door 728 further includes a pivoting mechanism having a pivot hinge (not shown) and a locking hinge 764 to enable a corresponding drawer to angle forward and pivot outward from the cabinet interior into an open position. In particular, locking hinge 764 includes a receptacle 766 disposed on a corresponding door 728, a curved track or slide 768 and a pin or bolt disposed within the cabinet interior (not shown). Receptacle 766 is disposed toward an intermediate portion of the corresponding door and extends from that door interior surface toward the cabinet interior. The receptacle includes an opening through which a pin or bolt 770 is inserted to connect a proximal end of slide 768 to the corresponding door.

Curved slide 768 typically extends from receptacle 766 of the corresponding door into the cabinet interior and curves toward cabinet bottom wall 712. The slide includes an opening 772 extending along the slide from the receptacle into the cabinet interior, whereby an associated cabinet interior bolt is disposed within and through the opening to enable the corresponding drawer to pivot out of and into the cabinet interior to open and closed positions, respectively. The distal end of the slide, in combination with the associated cabinet interior bolt, serves as a stop to limit pivoting or the forward angle of the corresponding drawer. Locking hinge 764 may be disposed adjacent either side wall 734, 736 of the corresponding drawer, or a door may include dual pivoting mechanisms, whereby a mechanism is disposed adjacent each corresponding drawer side wall. An operator typically grasps handle 738 of a corresponding door and applies force to draw that handle forward, thereby forcing slide 768 of that door forward, while the associated cabinet interior bolt traverses corresponding slide opening 772. When sufficient force is applied to the handle, the distal end of the corresponding slide opening is caused to engage the associated cabinet interior bolt to prevent further pivoting of a corresponding drawer. Conversely, force may be applied to the handle to facilitate pivoting of the corresponding drawer toward the cabinet to a closed position, whereby the corresponding slide is forced into the cabinet interior, while the associated cabinet interior bolt traverses corresponding slide opening 772.

The system may further include temperature sensing devices 125 (FIG. 23), preferably in the form of temperature sensing strips, and timing devices or timers 702 to measure and display the residence time of a medical item within an associated sub-compartment. Temperature sensing devices 125 are disposed within respective sub-compartments 752*a*, 752*b* and 752*c* of each drawer proximate window or material 742. The medical items within the sub-compartments are in thermal relation with the corresponding temperature sensing devices to enable the devices to measure and display the item temperatures as described below. Material 742 is substantially transparent to enable viewing of the temperature indications through the window.

Temperature sensing devices 125 are each preferably in the form of a substantially rectangular strip and include a temperature scale 122 arranged in a vertical fashion to measure and display a solution temperature in a particular temperature range. The temperature scale typically includes numerical indicators 130 arranged in sequential order, whereby each indicator represents a ten degree temperature interval (e.g., 70° F., 80° F., 90° F., 100° F., 110° F. as viewed in FIG. 23).

The temperature sensing strip preferably includes a series of temperature sensitive substances that provides visual color changes to or illuminates the temperature scale indicators to display a solution temperature. In particular, each temperature scale indicator 130 is typically associated with a temperature sensitive substance having a particular temperature threshold range corresponding to that indicator. When the solution temperature is within the threshold temperature range of a substance, that substance changes color or illuminates the associated temperature scale indicator to display the solution temperature. For example, if the solution has a temperature of 90° F., then only the temperature scale indicator representing a ninety degree temperature changes color or becomes illuminated to visually display the solution temperature. The temperature thresholds may be adjusted in any manner to enable a single or a plurality of temperature scale indicators to be illuminated in response to a solution temperature residing between successive temperature scale indicators. Further, the temperature thresholds may be set to illuminate a successive indicator (e.g., a 90° F. indicator may be set to illuminate at any temperature between 90° F.-100° F.).

The temperature sensing strip is preferably implemented by a conventional temperature strip having common temperature sensitive substances (e.g., a liquid crystal composition), such as the types of substances disclosed in U.S. Pat. No. 3,651,695 (Brown), U.S. Pat. No. 3,861,213 (Parker), U.S. Pat. No. 3,864,976 (Parker), U.S. Pat. No. 4,859,360 (Suzuki et al) and U.S. Pat. No. 5,806,528 (Magliochetti). The disclosures of the foregoing patents are incorporated herein by reference in their entireties. By way of example only, each temperature sensing device 125 includes a configuration where temperature scale 122 has duplicate temperature scale indicators 130 for each temperature level with corresponding temperature sensitive substances disposed between the duplicate scale indicators and displays temperatures in the range of 70° F.-110° F., whereby the duplicate temperature scale indicators 130 for each level represent a successive ten degree temperature interval (e.g., 70° F., 80° F., 90° F., 100° F. and 110° F). However, the temperature sensing device may be of any size or shape, while the temperature scale may include any quantity or types of indicators for representing any sized intervals in any desired temperature range.

Timers 702 are each associated with a corresponding drawer sub-compartment and are disposed on front wall 718 adjacent the corresponding drawer. Timers 702 each include a display 140 to indicate the amount of time a medical item has resided within a corresponding sub-compartment. In other words, the timer measures and indicates the amount of time a medical item has been warmed by the system. The timer may be implemented by any conventional or other timing or time measuring devices and may include any conventional or other type of display (e.g., LED, LCD, etc.).

Timers 702 are each controlled by a corresponding timer switch 150 (FIG. 22) to measure and indicate residence time in accordance with placement of a medical item within that sub-compartment. Timer switch 150 is disposed within each sub-compartment on drawer back wall 730. Basically, when a medical item is placed into a sub-compartment and against a timer switch, the timer switch enters a closed state and enables a corresponding timer 702 to begin measuring elapsed time. The elapsed time is displayed on display 140 of that timer, preferably in the format of hours, minutes and seconds. However, the elapsed time may be measured and/or displayed in any desired format or fashion (e.g., days, hours, minutes, seconds, etc.). When the medical item is removed from the sub-compartment, the timer switch enters an open state, thereby causing the timer to reset as described below. The timer display notifies medical personnel of the residence time of a medical item within the sub-compartment. In other words, the timer informs medical personnel of the amount of time a medical item has been warmed. Since medical items typically have limits with respect to warming time, medical personnel may remove the warmed medical item prior to excessive heating of the medical item and reduction in effectiveness.

Controller 722 typically includes a display 774 (e.g., LED or LCD) and a plurality of input devices or buttons 776 for enabling entry of a desired or set point temperature for each drawer. Input devices 776 are manipulated to enable entry of the desired temperatures, while display 774 may alternatively indicate the actual temperature for each drawer measured by a corresponding temperature sensor 756 (FIG. 24) or the desired or set point temperature for each drawer entered by the operator. Display 774 typically displays the measured drawer temperatures, and may be directed, via the input devices, to display the set point temperatures.

The controller essentially implements a feedback control loop to control heating of the drawers. Specifically, controller 722 receives a temperature signal from each temperature sensor 756 indicating the temperature of the corresponding drawer bottom wall. In response to the measured temperature of a corresponding drawer bottom wall being equal to or exceeding the desired temperature associated with that drawer, the controller disables power to the associated heating element via a solid state relay described below. Conversely, when the measured temperature of the corresponding drawer bottom wall is below the desired temperature associated with that drawer, the controller enables power to the associated heating element via the solid state relay. The controller may be implemented by any conventional or other controller, processor or circuitry utilizing any control algorithm (e.g., fuzzy logic, PID, etc.) to control the heating elements.

Figure 26:
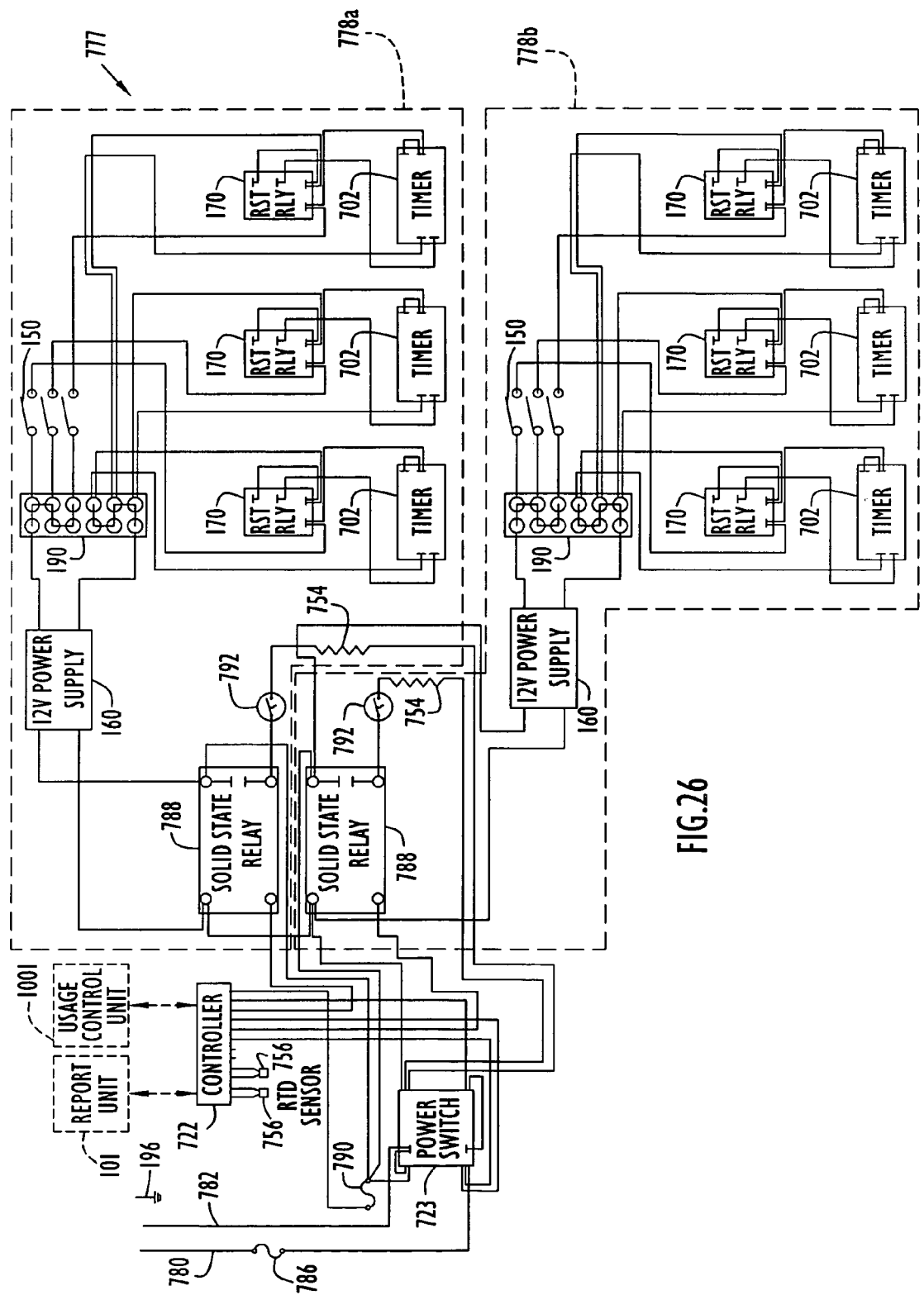
FIG. 26 is an electrical schematic diagram of an exemplary control circuit of the system of FIG. 22.

An exemplary control circuit of the temperature control system is illustrated in FIG. 26. Specifically, system control circuit 777 includes control circuits 778a, 778b to control heating of corresponding drawers 706a, 706b, respectively. The control circuits are coupled to controller 722 and power switch 723 to enable power to the circuits and control the heaters. A conductor 780 typically supplies a positive potential, while a conductor 782 provides a negative or reference potential. A conductor 196 is connected to ground. A fuse 786 is connected in series with conductor 780 and the power switch, while a fuse 790 is connected between the controller, power switch and solid state relays 788 of control circuits 778a, 778b to prevent surges from damaging the circuitry. Power switch 723 is connected to conductors 780, 782. The power switch is further connected to controller 722 and heaters 754 and solid state relays 788 of control circuits 778a, 778b to enable power to those components.

Control circuit 778a includes temperature sensor 756, conventional solid state relay 788, a conventional temperature cut out switch 792 and heating element or pad 754. Controller 722 receives power from power switch 723 and is further connected to temperature sensor 756 and solid state relay 788 of control circuit 778a. The temperature sensor measures a corresponding drawer bottom wall temperature and transmits a signal to controller 722 indicating that temperature. The controller controls the solid state relay to enable or disable power to the heating pad based on the measured temperature as described above. The solid state relay is connected to the heating pad, while temperature cut-out switch 792 is connected between the relay and heating pad to disable the heating pad in response to detecting a heating pad temperature in excess of a predetermined threshold.

Control circuit 778a further includes timers 702, reset relays 170, timer switches 150, a connection terminal 190 and a power source 160. The power source is connected to the solid state relay and connection terminal, while the timer switches 150 are each connected between the connection terminal and a corresponding reset relay 170 to facilitate control of the corresponding sub-compartment timer in accordance with the presence of a medical solution container within that sub-compartment. Each reset relay is connected to a corresponding timer and timer switch and may be implemented by any conventional or other relay type device. Basically, the timer switch enables a corresponding reset relay to control a corresponding timer. When a medical solution container is present in a sub-compartment, the timer switch is in a closed state as described above. Accordingly, the connection, via the connection terminal, between the power source and reset relay is enabled. The reset relay controls the reset of a corresponding timer 702. The timer basically resets when the reset line is low or grounded. Thus, when a medical item is removed from a sub-compartment and the corresponding timer switch enters an open state, the corresponding reset relay does not receive power from the power source and provides a low signal to the timer reset line, thereby facilitating a timer reset. When the timer switch enters a closed state due to the presence of a medical solution container in the sub-compartment, the corresponding reset relay receives power signals from the power source, thereby providing a high signal to the timer reset line enabling the timer to operate. Control circuit 778a may be implemented by any conventional circuitry components performing the above-described functions. Control circuit 778b is connected in parallel with and is substantially similar to control circuit 778a described above to control heating of drawer 706b.

System 700 includes a configuration similar to that described above for system 100 and may include report unit 101 and/or usage control unit 1001 coupled to controller 722 to generate, transmit and/or print reports and/or control system usage as described above for system 100. The drawer sub-compartments may each further include an interface 20 in the form of a wireless transmitter/receiver (e.g., RF, infrared, etc.), bar code scanner or connector or port to communicate with the medical item or identify the medical item to system 700 for storage of monitored information as described above.

Operation of the temperature control system is described with reference to FIGS. 22-26. Initially, an operator selects intravenous solution bags (e.g., containing intravenous solution) or other medical items for heating within the cabinet and determines appropriate temperatures for the items. The items may include the devices described above for solution bag 2. The operator subsequently selects a drawer 706a, 706b and enables power switch 723, whereby the operator grasps and applies force to handle 738 of the selected drawer to pivot that drawer outward from the cabinet interior to an open position. Intravenous solution bags are disposed within any quantity (e.g., at least one) or combination of corresponding drawer sub-compartments 752a, 752b, 752c such that any one sub-compartment contains a single intravenous solution bag. In response to placement of a container in the sub-compartment, the container engages and causes closure of a corresponding timer switch 150. The switch closure provides a connection between power source 160 and corresponding reset relay 170 that initiates the timer. The selected drawer is subsequently pivoted into the cabinet interior to a closed position, while the timer continuously displays the elapsed time to medical personnel on timer display 140 as described above. The desired temperature for each utilized drawer is entered into controller 722 via input devices or buttons 776. The controller receives signals from corresponding temperature sensors 756 (FIG. 24) and determines appropriate controls for solid state relays 788 (FIG. 26) to enable or disable power to heating pads 754 of the utilized drawers as described above. The heating pads apply heat to corresponding drawer bottom walls, whereby the drawer rear, side and divider walls conduct heat from the bottom wall to evenly distribute heat to the intravenous solution bags residing within the corresponding drawer sub-compartments as described above.

Controller 722 displays on display 774 each drawer bottom wall temperature measured by a corresponding temperature sensor 756, and may be directed to alternatively display the desired temperature entered for each drawer based on manipulation of input devices 776. Temperature sensing devices 125 measure and display the medical item temperature during heating as described above. Further, the intravenous solution bags may be viewed through transparent material 742 during heating. Moreover, system 700 may collect and provide information or reports (e.g., FIGS. 12A-12I) and/or control system usage as described above for system 100, where the reports or information can be transmitted to an internal printer 110, display 774 or to a local or remote external device (e.g., printer, display, database, medical item, etc.) as described above.

When the intravenous solution bags have attained the desired temperature, the selected drawer is pivoted to an open position as described above, whereby the heated bags are removed from sub-compartments of the selected drawer for use. The corresponding timer switches subsequently enter an open state, thereby resetting the corresponding timers and displays. Additional intravenous solution bags may replace the removed heated bags within those sub-compartments for heating by the system. It is to be understood that either or both of the drawers may be used and independently controlled in substantially the same manner described above to maintain items at the same or different desired temperatures. Further, any quantity of intravenous solution bags or items may be disposed within the sub-compartments and drawers for heating by the cabinet.

Figure 27A:
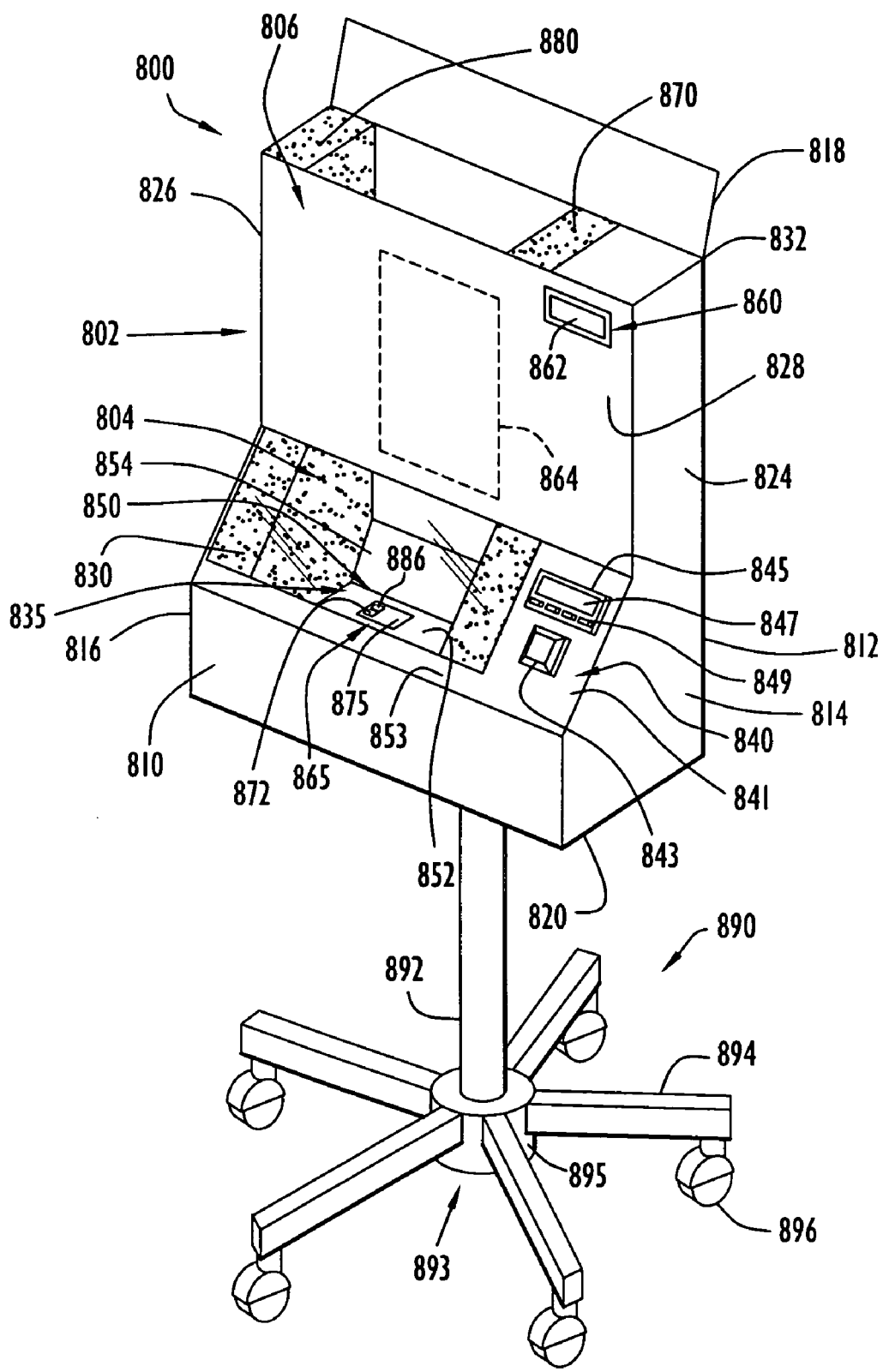
FIG. 27A is a view in perspective of a temperature control system including guides and a timer according to the present invention.
Figure 27B:
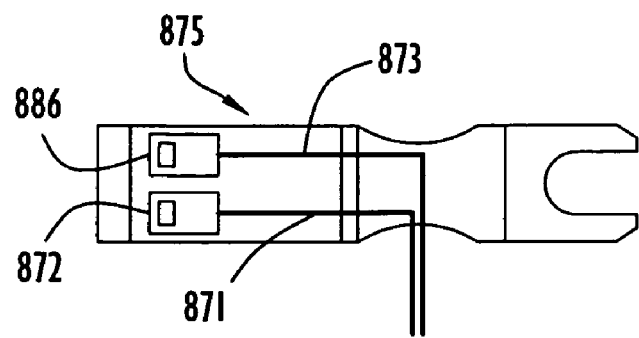
FIG. 27B is a top view in plan of a limit switch arm employed by the system of FIG. 27A.
Figure 27C:
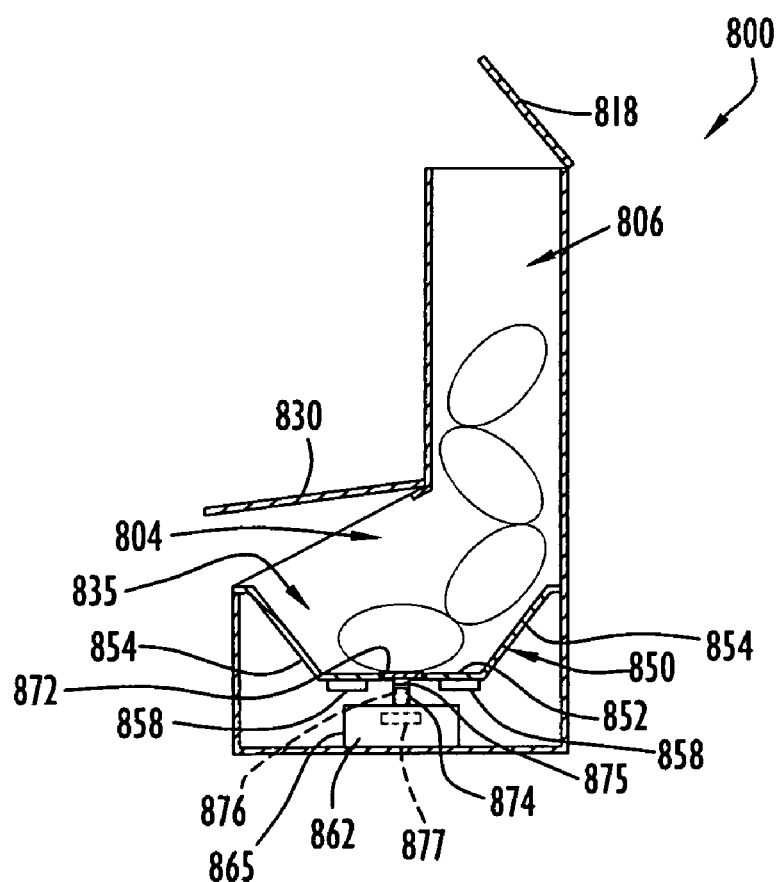
FIG. 27C is a side view in partial section of the system of FIG. 27A.

Yet another temperature control system of the present invention for thermally treating and/or monitoring medical solution containers (e.g., bags or bottles containing saline or intravenous (IV) solutions, antibiotics or other drugs, blood, etc.) or other medical items (e.g., instruments, blankets, etc.) with direct measurement of medical item temperature and display of medical item residence time within the system is illustrated in FIGS. 27A-27C. Initially, the system is of the type disclosed in aforementioned U.S. patent application Ser. No. 10/076,112. Specifically, system 800 includes a housing 802 including a heating compartment 804 and a storage compartment 806 disposed above the heating compartment. The heating compartment includes a front wall 810, a rear wall 812, side walls 814, 816, a bottom wall 820 and a front panel 840 that collectively define the heating compartment interior. A door 830 is disposed on the housing to cover a heating compartment open portion that facilitates placement and removal of items within the heating compartment as described below. Front and rear walls 810, 812 are substantially rectangular and are attached to and extend between side walls 814, 816. Front wall 810 has a height substantially less than that of rear wall 812. Bottom wall 820 is substantially rectangular and is attached to the bottom edges of the heating compartment front, rear and side walls. Side walls 814, 816 are generally rectangular with respective truncated upper front corner sections. The truncated section of side wall 814 includes an angled edge that extends from front wall 810 toward the storage compartment. The truncated section of side wall 816 includes a similarly angled edge.

Front panel 840 includes a control panel 841 and a projection 853. The control panel is substantially rectangular and is attached to front wall 810 and the angled edge of side wall 814. The control panel has a transverse dimension substantially less than the distance between side walls 814, 816 and is oriented at an angle toward rear wall 812 similar to that of the angled edge of side wall 814. Projection 853 is substantially rectangular and is attached to front wall 810, a control panel lower section and side wall 816. The projection extends from the front wall toward the storage compartment for a slight distance and is oriented at an angle similar to that of control panel 841. The open area between control panel 841, side wall 816 and projection 853 defines the heating compartment open portion.

Storage compartment 806 is disposed above heating compartment 804 and includes a top wall 818, side walls 824, 826 and front and rear walls 828, 832 that collectively define the storage compartment interior. Front and rear walls 828, 832 are substantially rectangular and are attached to and extend between side walls 824, 826. Front wall 828 extends from the upper edges of door 830 and control panel 841, while rear wall 832 extends from and is integral with heating compartment rear wall 812. Side walls 824, 826 are substantially rectangular and are attached to and extend between respective side edges of front and rear walls 828, 832. The side walls respectively extend from and are integral with respective heating compartment side walls 814, 816.

Top wall 818 is substantially rectangular and is attached to the upper edges of the storage compartment front, rear and side walls. Top wall 818 further provides access to the storage compartment and is typically pivotally connected to rear wall 832. The top wall opens upward from the storage compartment to enable placement and removal of medical solution containers within the system. Door 830 is typically pivotally connected to the lower portion of front wall 828 and opens upward from the heating compartment in order to provide access to the heating compartment for placement and removal of medical solution containers within that compartment. Top wall 818 and door 830 may both be partially or completely transparent to allow viewing of the storage and heating compartment interiors, respectively. In addition, top wall 818 and/or door 830 may include any type of handle or latching mechanism to facilitate access to the system interior. The storage compartment basically houses additional medical solution containers to enable the system to accommodate and heat plural containers as described below.

Control panel 841 includes a power switch 843 and a controller 845 to indicate solution temperature and control operation of the system as described below. Controller 845 includes a display 847 (e.g., LED or LCD) and a plurality of input devices or buttons 849. The input devices are manipulable by a user to enable entry of a desired or set point temperature for a medical solution container placed within the housing compartment. Display 847 typically displays the measured temperature of the solution and may further be directed, via input devices 849, to display the desired or set point temperature. The controller receives a desired temperature from a user and controls heating of a medical solution to attain that temperature as described below. The heating compartment houses a heating assembly 835 to uniformly apply heat to a medical solution. The heating assembly includes heating plate 850, heater 858 (FIG. 29), temperature sensor 872 and limit switch 865. The heating plate includes bottom wall 852 and side walls 854 extending at an angle from the bottom wall longer dimensioned side edges toward the interior surfaces of the heating compartment front and rear walls to form a generally 'U'-shaped heating plate configuration. Heater 858 is disposed on the bottom surface of the heating plate bottom wall. This arrangement facilitates rapid heating of a medical item which is especially advantageous during employment of the system in time critical situations, such as in an operating room. For example, the system may heat items to a desired temperature in the approximate range of 80° F. to 150° F. within a short time interval, generally within one hour (e.g., the particular time interval depends on various factors, such as initial item temperature, room temperature, selected desired temperature, etc.).

Limit switch 865 controls heater 858 in response to placement and removal of medical solution containers on the heating plate. Specifically, the limit switch is typically implemented in the form of a pressure type switch that enables or disables the heater in response to detection of pressure (e.g., the weight of a container) applied to a portion of the heating plate. However, the limit switch may alternatively be configured in any manner suitable for operation of the system. The limit switch includes a housing 862 (FIG. 27C) and an arm 875 (FIG. 27B). The limit switch housing is disposed beneath the heating plate bottom wall and includes a post or support member 874 extending from the housing top surface toward the heating plate. Arm 875 is attached in a cantilevered manner to the support member. Temperature sensors 872, 886 are mounted on arm 875 toward the arm distal end with wiring 871, 873 extending from the respective sensors to controller 845. Temperature sensor 886 basically measures excessive temperatures and serves as a cut-off switch as described below. The arm extends from the support member along the underside of the heating plate bottom wall to align sensor 872 with an opening (not shown) defined in the heating plate bottom wall. The bottom wall opening provides temperature sensor 872 with access to a medical solution container placed on the heating plate. The limit switch arm is constructed of a resilient material that biases the arm toward the heating plate and enables the arm to move between that plate and the limit switch housing. The arm bias further forces the temperature sensor against a medical solution container placed on the heating plate, thereby facilitating an accurate temperature measurement. A contact member 876 is disposed on the limit switch housing coincident a distal portion of the limit switch arm and extends into the limit switch housing via an opening (not shown) defined in that housing. The contact member is typically directly attached to or resiliently biased toward the limit switch arm to enable movement of the contact member into or out of the limit switch housing in response to flexing of the limit switch arm.

The contact member is configured to actuate switch circuitry 877 disposed within the limit switch housing. In particular, the limit switch arm flexes toward the limit switch housing in response to pressure applied to the arm from a medical solution container placed on the heating plate. The contact member is subsequently urged into the housing and interfaces the switch circuitry. This motion results in actuation of the switch circuitry and effectively closes switch 865, thereby enabling heater 858. When a container is removed from the heating plate, arm 875 is biased toward the heating plate bottom wall with the contact member being withdrawn from the switch circuitry. This motion effectively results in disablement of the switch circuitry and effectively opens switch 865, thereby disabling the heater. The limit switch arm may further include a cut-out switch and/or additional temperature sensor 886 to facilitate disablement of the heater in response to excessive temperatures.

System 800 further includes a timer 860 (FIG. 27A) to measure and display residence time of a medical item on heating plate 850. Timer 860 is disposed on front wall 828 toward an upper front wall corner adjacent side wall 824. Timer 860 includes a display 862 to indicate the amount of time a medical item has resided on the heating plate. In other words, the timer measures and indicates the amount of time a medical item has been warmed by the system. The timer may be implemented by any conventional or other timing or time measuring devices and may include any conventional or other type of display (e.g., LED, LCD, etc.). In addition, front wall 828 may further include a substantially rectangular window 864 disposed adjacent timer 860 to enable medical personnel to view and ascertain the quantity of medical items within storage compartment 806. The window may be of any shape or size, may be disposed at any suitable locations and may be constructed of any suitably transparent materials (e.g., glass, plastics, etc.).

System 800 may be mounted on a stand 890 to facilitate transport of the system to various sites (e.g., operating room, patient room, etc.). The stand includes a post 892 and a base 893. The base is basically configured in a star type configuration and includes a hub 895 and a plurality of legs 894. The hub is generally cylindrical with legs 894 extending transversely therefrom. The legs are in the form of generally rectangular rods and each leg includes a caster or roller 896 to enable transport of the system. Post 892 is substantially cylindrical and extends upward from hub 895. The post engages bottom wall 820 of system 800 to connect the system to the stand. The post and/or system bottom wall may include any conventional or other fasteners to couple the system to the stand. Alternatively, system 800 may be mounted to any support structures (e.g., wall, pole, door, stands, etc.) via any conventional fastening mechanisms (e.g., brackets, hooks, etc.). The stand may be utilized with any of the thermal treatment systems described herein.

Timer 860 is controlled by limit switch 865 to measure and indicate residence time in accordance with placement of a medical item on heating plate 850. Basically, when a medical item (FIG. 27C) is urged by gravitational forces or manually manipulated onto the heating plate and limit switch as described above, the limit switch enters a closed state and enables timer 865 to begin measuring elapsed time. The elapsed time is displayed on timer display 862, preferably in the format of hours, minutes and seconds. However, the elapsed time may be measured and/or displayed in any desired format or fashion (e.g., days, hours, minutes, seconds, etc.). The limit switch further actuates a time delay relay that delays operation of the heater for a predetermined time interval. This delay enables the temperature of temperature sensor 872 to approach the medical item temperature to provide enhanced temperature measurements as described below. When the medical item is removed from the heating plate, the limit switch enters an open state, thereby causing the timer to reset via a reset relay as described below. The timer display notifies medical personnel of the residence time of a medical item on the heating plate. In other words, the timer informs medical personnel of the amount of time a medical item has been warmed. Since medical items typically have limits with respect to warming time, medical personnel may remove the warmed medical item prior to excessive heating of the medical item and reduction in effectiveness. Upon removal of a medical item from the heating plate, the next medical item within the storage compartment is gravitationally urged or manually manipulated onto the heating plate and the limit switch enters a closed state to start the timer and time delay as described above.

The configuration of heating plate 850 enables uniformed heating of the medical item as described above. However, the uniform heating may be adversely affected when a medical item is disoriented or improperly positioned on the heating plate. Accordingly, system 800 may further include guides 870, 880 (FIG. 27A) to orient and ensure proper placement of a medical item on the heating plate. In particular, guide 870 is typically inserted within the system, via top wall 818, and disposed adjacent side walls 814 and 824. Similarly, guide 880 is disposed in the system via the top wall and disposed toward side walls 816 and 826. The guides distal ends each rest at respective opposing ends of heating plate 850 and extend from the heating plate through heating and storage compartments 804, 806 to top wall 818. The guides basically form a channel therebetween having dimensions slightly larger than the corresponding medical item. The medical item is inserted within the storage compartment in the channel, where the medical item orientation is maintained by the guides for proper placement on the heating plate.

Referring to FIGS. 28A-28D, each guide is generally 'L'-shaped and includes a leg 882 and a foot 884. The leg is generally rectangular and has a height substantially similar to the distance between the heating plate and top wall 818. The depth of the leg is slightly less than the distance between the storage compartment front and rear walls to enable insertion of the guide into the system. Foot 884 is generally rectangular and connected at an obtuse angle to a distal end of leg 882. The foot has a truncated corner on its bottom edge to provide a configuration to accommodate the contour of the heating plate. The guides are preferably constructed of foam material, but may be constructed of any suitable materials.

The dimensions of the guides may vary in accordance with the dimensions of the medical item and system housing employed. For example, the height of leg 882 may vary to accommodate different sized system housings, while the width of the guides may vary to accommodate varying sized medical items. By way of example only, the guides of FIGS. 28A-28B may accommodate liter solution bags and include thinner dimensions than those of the guides in FIGS. 28C-28D which may accommodate half liter solution bags. The thinner dimensions of the guides in FIGS. 28A-28B enable a greater distance or larger dimensioned channel to reside between the guides to accommodate larger solution bags. Conversely, the thicker dimensions of the guides in FIG. 28C-28D enable a lesser distance or smaller dimensioned channel to reside between the guides to accommodate smaller solution bags. Similarly, the guides of FIGS. 28A and 28C include greater heights than those of the guides of FIGS. 28B and 28D in order to accommodate a taller housing. The guides are inserted into system 800 each toward a respective side wall, where each foot 884 resides on and contours the heating plate with a corresponding leg 882 extending therefrom toward the housing top wall. The distance between the guides provides a channel to maintain proper orientation of medical items within the system as described above.

Figure 29:
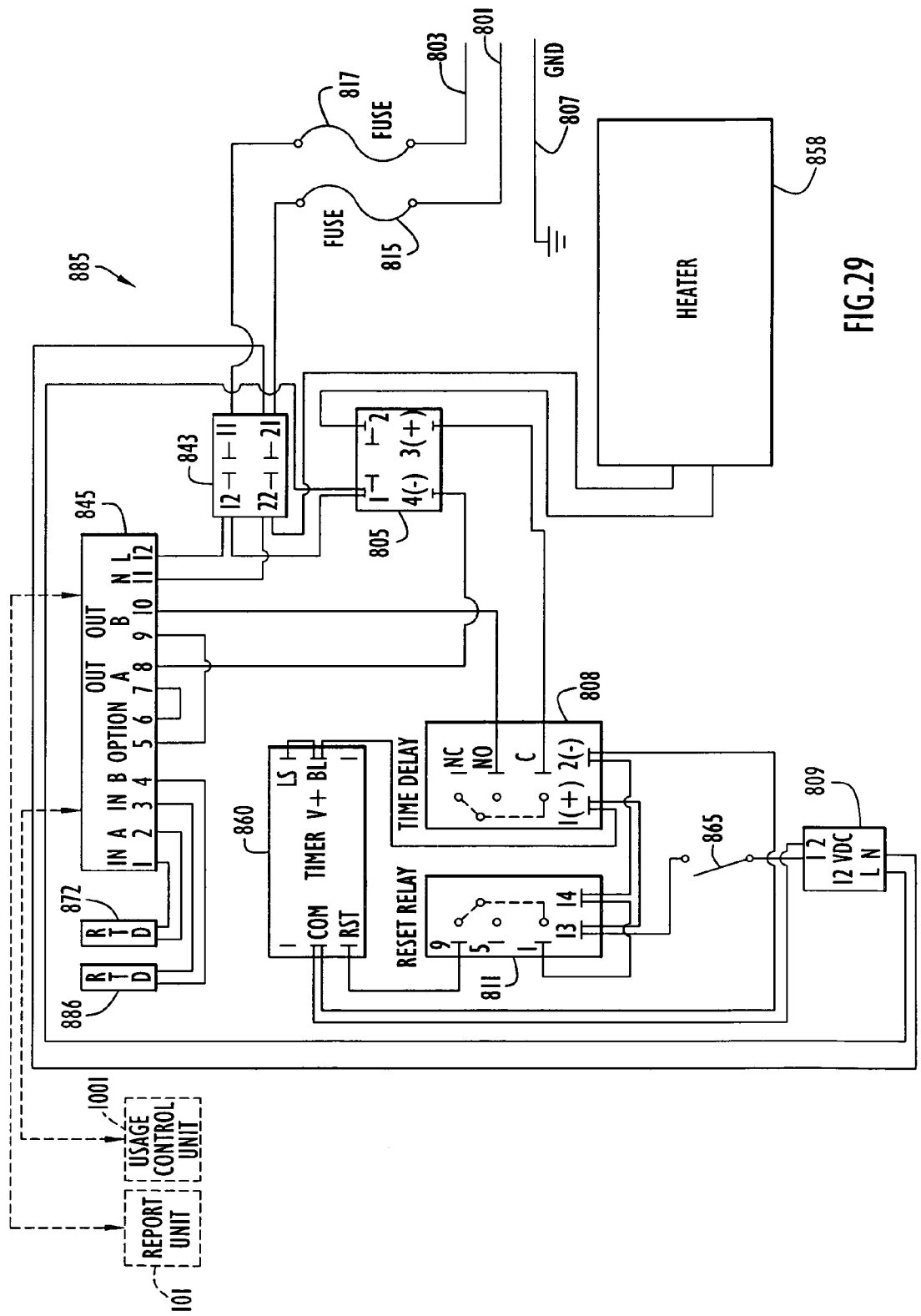
FIG. 29 is an electrical schematic diagram of an exemplary control circuit for the system of FIG. 27A.

An exemplary control circuit for system 800 is illustrated in FIG. 29. Specifically, control circuit 885 includes power conductors 801, 803, ground 807, power switch 843, controller 845, solid state relay 805, limit switch 865, heater 858 and temperature sensors 872, 886, each as described above. The circuitry further includes timer 860, a time delay relay 808, a reset relay 811 and a power source 809. Power conductors 801, 803 each include a respective fuse 815, 817 (e.g., a conventional 2 amp fuse) that is arranged in series with power switch 843 to prevent power surges from damaging the switch and circuitry. Power switch 843 controls power to the circuitry and is connected to the controller, solid state relay, power source and heater. The power switch may include a light to illuminate the switch. Controller 845 is further connected to solid state relay 805 and temperature sensors 872, 886. The controller controls power applied to the heater via relay 805 in accordance with a comparison of a temperature measured by temperature sensor 872 and a desired temperature entered into the controller by a user. In particular, controller 845 receives temperature signals from temperature sensor 872 indicating the temperature of a medical solution container in contact with the sensor (i.e., the container disposed on the heating plate surface). In response to the temperature measured by temperature sensor 872 being equal to or exceeding a desired temperature entered by a user, the controller disables power to the heater via solid state relay 805. Conversely, when the temperature measured by temperature sensor 872 is below the desired temperature, the controller enables power to the heater via the solid state relay.

Limit switch 865 is connected between power source 809 and reset relay 811 and facilitates control of the heater and timer in accordance with the presence of a medical solution container within the system. The power source is further connected to timer 860, while time delay relay 808 is connected to reset relay 811, controller 845 and solid state relay 805. The reset and time delay relays may be implemented by any conventional or other relay type devices. Basically, the limit switch enables the time delay and reset relays to control the timer and power to the heater. When a medical solution container is present on the heating plate, the limit switch is in a closed state as described above. Accordingly, the connection between the power source and reset relay is enabled. The reset relay controls the reset of timer 860. The timer basically resets when the reset line is low or grounded. Thus, when a medical item is removed from the heating plate and the limit switch enters an open state, the reset relay does not receive power from the power source and provides a low signal to the timer reset line, thereby facilitating a timer reset. When the limit switch enters a closed state due to the presence of a new medical solution container on the heating plate, the reset relay receives power signals from the power source, thereby providing a high signal to the timer reset line enabling the timer to operate. The reset relay further energizes the time delay relay which prevents solid state relay 805 from enabling the heater for a predetermined time interval. Preferably, the delay time interval is approximately 7.5 minutes, however, the time interval may be set to any desired interval. The time delay enables the temperature of temperature sensor 872 to approach the temperature of a new medical item received on the heating plate to enhance temperature measurement. Basically, the temperature of the temperature sensor is elevated due to contact with a warmed medical item. When the warmed medical item is removed from the system, the temperature sensor maintains the elevated temperature for a short interval. Thus, the temperature sensor in this state may provide elevated temperature readings relative to the actual temperature of a new unwarmed medical item placed on the heating plate. The time delay enables the temperature sensor to cool and provide accurate temperature measurements. Once the time delay interval has expired, time delay relay 808 enables the solid state relay to control the heater in accordance with control signals from the controller as described above.

When a medical solution container is removed or absent from the heating plate, the limit switch is in an open state and the connection between the reset relay and power source is disabled. The reset relay does not receive power and provides a low signal on the reset line of timer 860 to reset the timer. Similarly, the time delay relay is without power and cannot energize solid state relay 805 to enable the heater. Thus, when the switch is in an open state indicating no medical item on the heating plate, the timer is reset and the heater is disabled.

Temperature sensor 886 is connected to the controller to facilitate disablement of the heater in response to detecting a temperature in excess of a predetermined threshold as described above. Basically, temperature sensor 886 provides a temperature indication of the solution container, heater and/or heating plate to controller 845. The controller disables power to the heater via relay 805 in response to the measured temperature exceeding a predetermined threshold as described above. Control circuit 885 may alternatively be implemented by any conventional circuitry components performing the above described functions, and may utilize a cut-off switch in place of temperature sensor 886 to disable the heater in response to excessive temperatures as described above.

System 800 includes a configuration similar to that described above for system 100 and may include report unit 101 and/or usage control unit 1001 coupled to controller 845 to generate, transmit and/or print reports and/or control system usage as described above for system 100. Heating compartment 804 may further include an interface 20 in the form of a wireless transmitter/receiver (e.g., RF, infrared, etc.), bar code scanner or connector or port to communicate with the medical item or identify the medical item to system 800 for storage of monitored information as described above.

Operation of system 800 is described with reference to FIGS. 27A, 27C and 29. Specifically, a user selects one or more medical solutions (e.g., bags or bottles containing saline or IV solutions, antibiotics or other drugs, blood, etc.) for heating by the system and determines the appropriate temperature for the solution. The solution bags may include the devices described above for solution bag 2. The system may be mounted on stand 890 and transported to a desired site. The user subsequently activates power switch 843 and pivots top wall 818 to an open state. The user may insert appropriately dimensioned guides 870, 880 into the system in order to properly orient the medical items on the heating plate as described above. The selected solution containers are placed into the system in stack relation with an initial container disposed on plate 850 as described above.

Top wall 818 is subsequently pivoted to a closed state and a desired temperature for the selected solutions is entered into controller 843 via controller input devices or buttons 849. The medical solutions within the storage compartment may be viewed through window 864 as described above. In response to placement of a container on the heating plate bottom wall, the container engages temperature sensor 872 and causes closure of limit switch 865. The switch closure provides a connection between power source 809 and reset relay 811 that initiates the timer and energizes time delay relay 808. The time delay relay disables the heater for the predetermined time interval as described above. Once the time delay interval has expired, solid state relay 805 is enabled and controlled by the controller in accordance with signals from temperature sensor 872 to enable or disable power to heater 858 as described above. Timer 860 continuously displays the elapsed time to medical personnel on timer display 862 as described above. The heater applies heat to the heating plate bottom wall, while heating plate side walls 854 conduct heat from bottom wall 852 to evenly distribute heat to the initial container. A cut-out switch and/or temperature sensor 886 may be employed to facilitate disablement of the heater in response to excessive heater, heating plate and/or solution temperatures as described above.

Controller 845 displays the temperature of the container as measured by temperature sensor 872, and may alternatively display the desired or set point 11 temperature entered by the user. Moreover, system 800 may collect and provide information or reports (e.g., FIGS. 12A-12I) and/or control system usage as described above for system 100, where the reports or information can be transmitted to internal printer 110, controller display 847 and/or to a local or remote external device (e.g., printer, display, database, medical item, etc.) as described above.

In response to attaining the desired temperature, the initial container is removed from the heating plate via door 830. The limit switch subsequently enters an open state, thereby disabling the connection between the power source and the reset relay. The reset relay provides a low signal to the timer, thereby resetting the timer and display. A successive container is urged by gravitational forces and/or manually manipulated into position on the heating plate bottom wall. The limit switch enters a closed state and initiates operation of the timer and time delay to repeat the process for this container. The above process may be repeated for subsequent containers stored in the system. Once the last container is removed, the limit switch disables the heater until another container is placed on the heating plate as described above.

Figure 30:
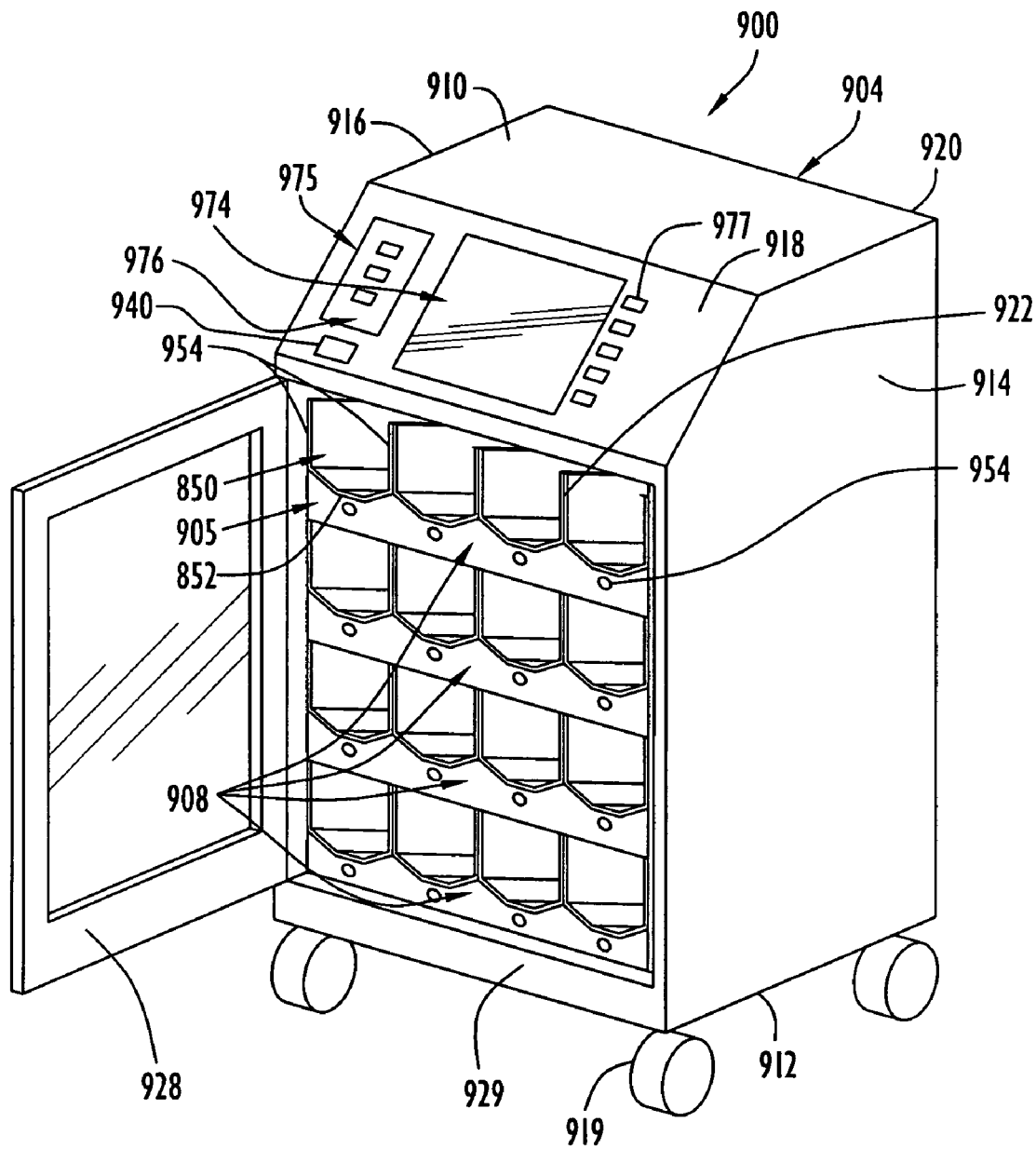
FIG. 30 is a view in perspective of a temperature control system for heating plural medical items and measuring and displaying residence time of those items within the system according to the present invention.

Still another temperature control system of the present invention for thermally treating and/or monitoring medical solution containers (e.g., bags or bottles containing saline or intravenous (IV) solutions, antibiotics or other drugs, blood, etc.) or other medical items (e.g., instruments, blankets, etc.) with direct measurement of medical item temperature and display of medical item residence time within the system is illustrated in FIG. 30. Specifically, temperature control system 900 includes a cabinet or system housing 904 with a series of heating trays 908. Cabinet 904 is generally in the form of a rectangular box and includes top and bottom walls 910, 912, side walls 914, 916, a front door 928, a front panel 918 disposed above the door, a front wall 929 and a rear wall

920. The cabinet door, front panel and top, bottom and front walls are each substantially rectangular, while the side walls are generally rectangular with a truncated upper front corner portion. Top wall 910 extends from rear wall 920 for a distance less than that between the rear wall and front door. Front panel 918 extends from the front door upper edge to the front edge of top wall 910 and is tilted at an angle. The side edges of the tilted front panel follow along the truncated upper front corners of side walls 914, 916. Front wall 929 is disposed beneath front door 928 and extends to bottom wall 912. The walls, panels and door collectively define a cabinet interior.

Trays 908 are disposed within the cabinet interior and may be mounted therein via any conventional or other mounting devices (e.g., rails, ledges, brackets, etc.). Each tray is preferably mounted in the system interior at a downward angle toward rear wall 920 and includes a plurality of heating assemblies 905, each with a heating plate 850 for receiving and heating a medical item to a desired temperature as described above. Heating assemblies 905 are substantially similar to heating assembly 835 described above for FIG. 27A, except that heating plate bottom wall 852 has a curved or arcuate configuration. The heating plate bottom wall side edges are attached to heating plate side walls 854 to form a curved or generally 'U'-shaped heating plate configuration as described above. By way of example only, system 900 includes four heating trays 908 with each tray including four heating assemblies 905, thereby enabling heating of a maximum of sixteen medical items at one time. However, the system may include any quantity of trays with each tray including any quantity of heating assemblies with any sized heating plates to accommodate various sized medical solution containers (e.g., one liter, three liter, etc.) or other medical items. A tray divider or partition 922 is typically disposed between adjacent assembly heating plates on each tray. However, adjacent heating plates may be placed proximate each other without a divider, or the heating plates may be constructed of or molded within a continuous sheet of conductive material and utilized with the heating assemblies in substantially the same manner described above.

Door 928 includes a handle (not shown) typically disposed toward an intermediate section side edge. The handle may be implemented by any conventional or other type of handle. Alternatively, the handle may be disposed on the door at any suitable location. Door 928 generally pivots toward and away from the cabinet, and is preferably constructed of electro-galvanized steel or other suitably sturdy material with an opening covered by a substantially transparent material, such as glass or plexiglass, to serve as a window to enable viewing of the medical items and maintain heat within the cabinet. Alternatively, the door may be constructed of a transparent material (e.g., glass, plastic, etc.). The door, opening and transparent material may be of any size or shape.

Rollers or casters 919 are attached to the cabinet bottom wall with each caster disposed toward a corresponding cabinet bottom wall corner to enable the system to be transportable. The casters or rollers may be of any quantity, may be implemented by any conventional or other types of rollers or wheel-type structures, and may be disposed at any locations on the cabinet. Further, the cabinet may be constructed of electro-galvanized steel or other suitably sturdy material, and may be of any size or shape.

Trays 908 are generally disposed in vertical alignment within the cabinet interior. The trays may be of any shape or size and may be constructed of any suitable materials. The system and trays may be configured to accommodate various sized medical items. By way of example only, the system is configured to accommodate liter medical solution bags. The heating plates each include a limit switch 865 (FIGS. 27A-27C) as described above to control heating and residence time measurement for a medical item. The limit switch includes temperature sensors 872, 886 disposed on limit switch arm 875 as described above (FIG. 27A-27C) to measure medical item and excessive temperatures, respectively.

A common system controller 930 (FIG. 32) enables entry of a desired or set point temperature for each heating assembly and includes a display 974 to display for each heating assembly the set point temperature, medical item temperature and current residence time of the medical item placed on that heating assembly. Thus, the system enables each heating assembly to be individually controlled to the same or different temperature. The display further provides a visual indication for a heating assembly when excessive temperatures have been detected for that heating assembly (e.g., an over temperature (e.g., an "overtemp") indication) or when a medical item is not present on that heating assembly (e.g., an "empty" or "reload" indication). Exemplary display screens are illustrated in FIGS. 31A-31B.

Display 974 is disposed toward an intermediate section of front panel 918, while a control panel 975 is generally disposed in the front panel adjacent the display. The control panel includes input devices 976 (e.g., keys, buttons, switches, etc.) to facilitate entry of information (e.g., enter or adjust set point temperature, switch between Fahrenheit and Celsius, etc.) and a power switch 940 to enable power to the system. Alternatively, display 974 may be implemented by a touch screen device to facilitate entry of information. Various indicators 977 are further disposed adjacent display 974 to notify an operator of system conditions (e.g., power enabled, etc.).

The system controller is in communication with heat controllers 952 (FIG. 33) each associated with a corresponding tray to individually control each of the tray heating assemblies and measure residence time. The system controller receives information entered by a user and transfers that information to the heat controllers to facilitate control of the heating assemblies. The heat controllers individually control each heating assembly of a corresponding tray in accordance with actuation of a corresponding limit switch, measured temperatures from corresponding temperature sensors 872, 886 and the set point temperature for that assembly received from the system controller. The heat controllers further maintain the residence time of medical items on the heating assemblies of the corresponding tray and may store residence time in memory in order to recover and maintain residence time measurements in the event of a power failure. The system controller receives the medical item temperature and residence time for the heating assemblies from the heat controllers for display on display 974. Further, the heat controllers each report excessive temperature detections and the presence of medical items for heating assemblies of the corresponding tray to the system controller to facilitate display of the excessive temperature and reload indications for the heating assemblies. In addition, the heat controllers illuminate heating assembly indicators 954 (e.g., LED), each disposed on a tray 908 proximate a corresponding heating assembly to indicate when a medical item on that heating assembly has attained or is near (e.g., within a predetermined or user-specified range from) the corresponding set point temperature.

Basically, when a medical item is placed on a heating plate and limit switch as described above, the limit switch enters a closed state and enables a corresponding heat controller to begin measuring elapsed time. The elapsed time is sent to the system controller for display on display 974, preferably in the format of hours, minutes and seconds. However, the elapsed time may be measured and/or displayed in any desired format or fashion (e.g., days, hours, minutes, seconds, etc.). The limit switch further facilitates a time delay, where the corresponding heat controller delays operation of the corresponding assembly heater for a predetermined time interval. This delay enables the temperature of a corresponding temperature sensor 872 to approach the medical item temperature to provide enhanced temperature measurements as described below. The medical item temperature, excessive temperature detections and presence of the medical item for the heating assembly are further sent to the system controller for display. When the medical item is removed from the assembly heating plate, the limit switch enters an open state, thereby causing the corresponding heat controller to reset the time and disable heating. Thus, the display notifies medical personnel of the residence time, temperature and presence of medical items on corresponding heating assemblies, where the residence time information informs medical personnel of the amount of time a medical item has been warmed. Since medical items typically have limits with respect to warming time, medical personnel may remove the warmed medical item prior to excessive heating of the medical item and reduction in effectiveness. Cabinet 904 may include any quantity of rollers, trays, heating assemblies, power switches, displays, indicators, controllers and accompanying control circuitry, while the cabinet components (e.g., walls, door, panel, etc.) may be arranged in any fashion.

Figure 32:
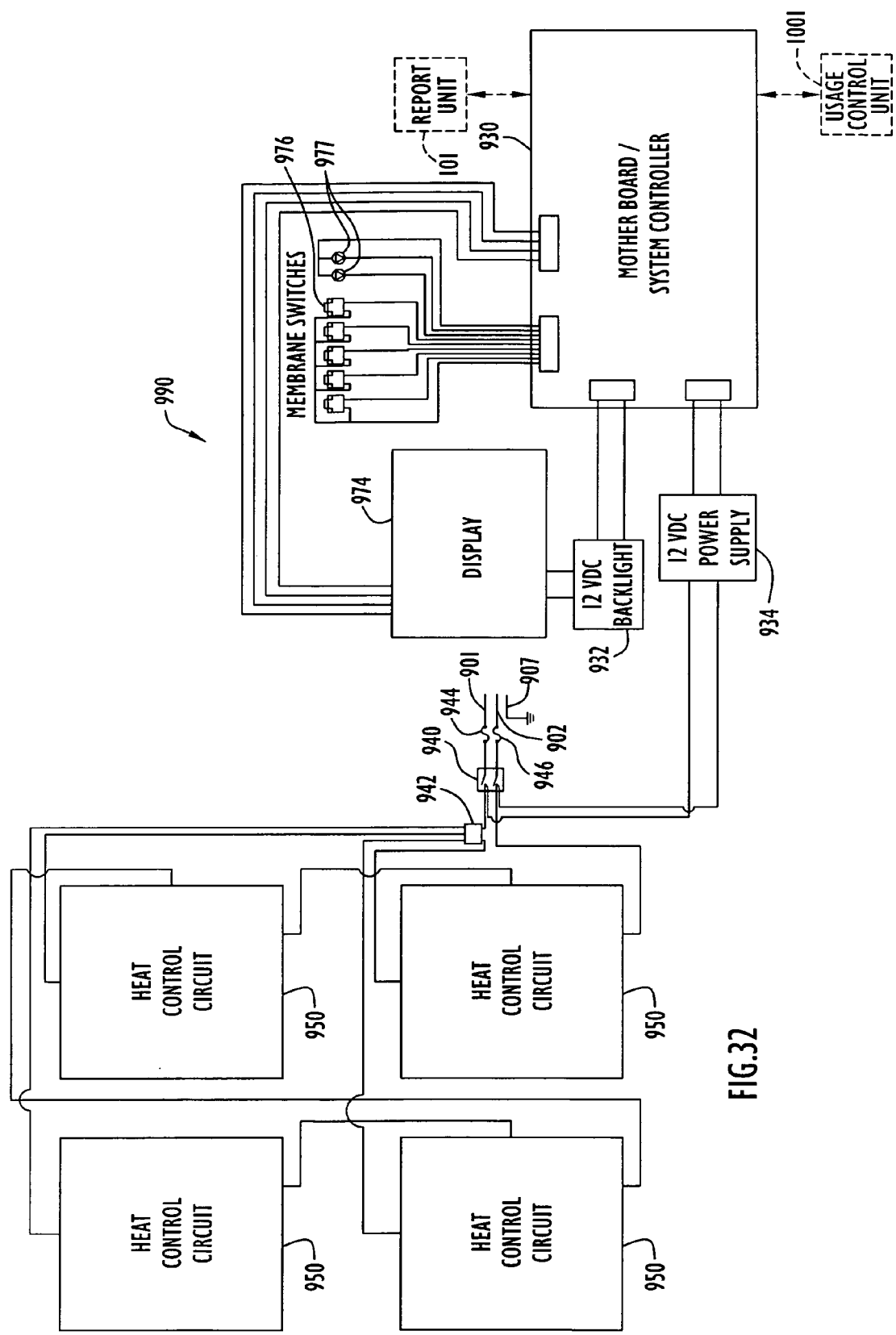
FIG. 32 is an electrical schematic diagram of an exemplary control circuit for the system of FIG. 30.

An exemplary control circuit for system 900 is illustrated in FIG. 32. Specifically, control circuit 990 includes power conductors 901, 902, ground 907, power switch 940, system controller 930, display 974, a back light 932, a power source 934, input devices 976, indicators 977 and heat control circuits 950. The heat control circuits are each associated with a corresponding tray 908 (FIG. 30) to individually control the heating assemblies of that tray as described below. Controller 930 is typically in the form of a motherboard including a controller and accompanying circuitry. However, the system controller may be implemented by any conventional or other controller, processor and/or circuitry. Power conductors 901, 902 each include a respective fuse 944, 946 that is arranged in series with power switch 940 to prevent power surges from damaging the switch and circuitry. Power switch 940 controls power to the circuitry and is connected to the power source. The power switch is further connected to the heat control circuits via a connection terminal 942.

Controller 930 is connected to power source 934, back light 932, display 974, input devices 976 and indicators 977. Further, the system controller is connected to (not shown) or in communication with heat controllers 952 of heat control circuits 950, where the communication or connection may be implemented in any desired fashion (e.g., wires, busses, etc.). The power source provides appropriate power signals (e.g., 12V DC) to the system controller, while the back light is controlled by controller 930 to provide suitable lighting conditions for the display. The system controller receives user information from input devices 976 and illuminates appropriate indicators 977 based on the user information and system conditions (e.g., power enabled, etc.). Set point temperature and other information received by the system controller are distributed to heat control circuits 950 to facilitate heating of medical items as described below. The system controller receives residence time, medical item temperature and other information (e.g., excessive temperature detection, presence of a medical item, etc.) from the heat control circuits and controls display 974 to display information (e.g., residence time, medical item temperature, excessive temperature detections, reload or empty indications, etc.) for the heating assemblies. The display is generally partitioned into sections with each section associated with a corresponding heating assembly (e.g., the location of a section on the display corresponds to the position of the associated heating assembly within the cabinet) to provide information pertaining to that assembly (FIGS. 31A-31B). The heating assemblies may each be associated with an identifier that appears on the display to associate displayed information with a corresponding heating assembly. However, the display may be arranged in any fashion to provide information to an operator.

Figure 33:
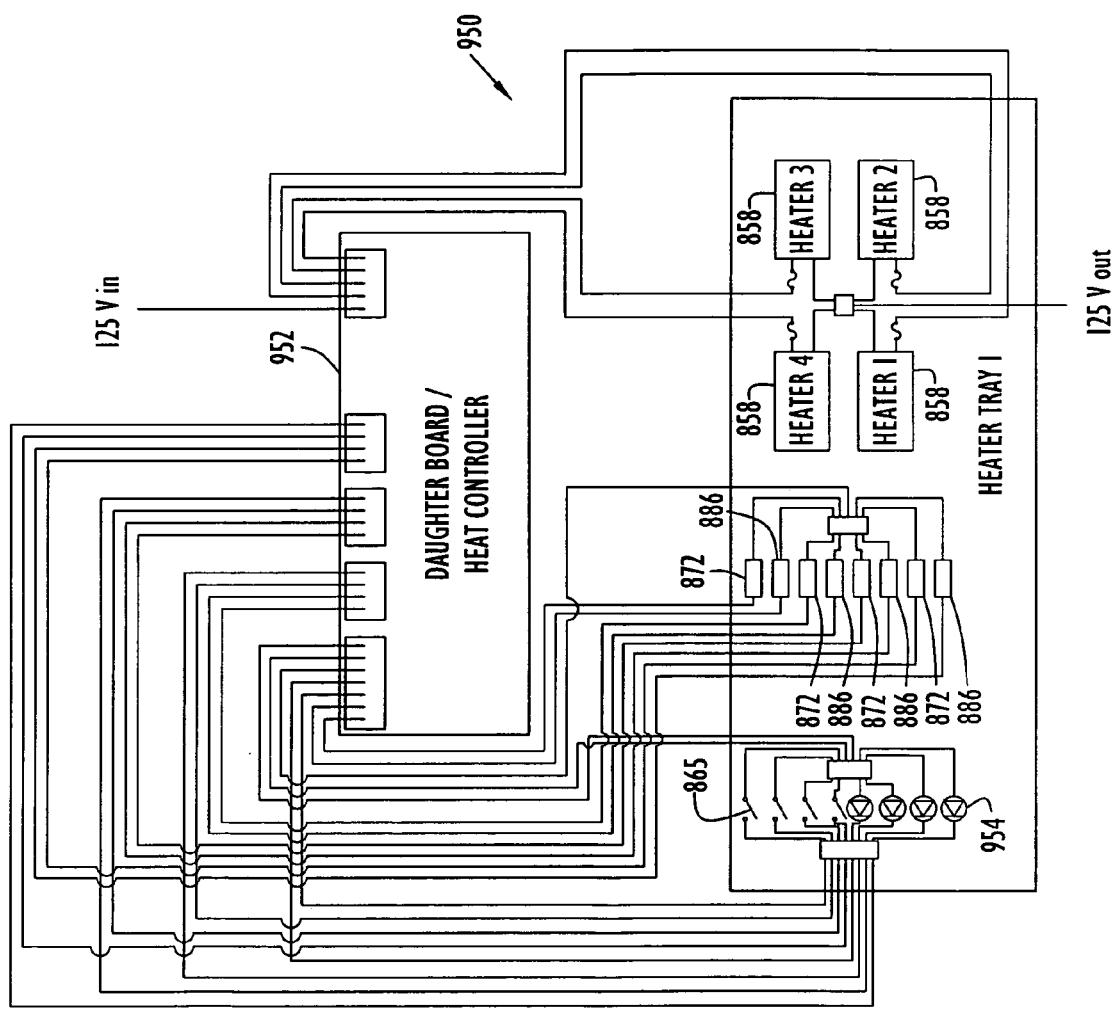
FIG. 33 is an electrical schematic diagram of a heat control circuit of the control circuit of FIG. 32.

An exemplary heat control circuit 950 is illustrated in FIG. 33. Specifically, heat control circuit 950 receives information from system controller 930 to control the heating assemblies of a corresponding tray 908 (FIG. 30). The heat control circuit includes a heat controller 952 and further includes limit switch 865, heater 858 and temperature sensors 872, 886 of each heating assembly of the corresponding tray. The heat controller is preferably in the form of a daughterboard with a controller and accompanying circuitry. However, the heat controller may be implemented by any conventional or other controller, processor and/or circuitry. The limit switch, heater and temperature sensors are substantially similar to the ones described above. The heat control circuit further includes indicators 954 each associated with a heating assembly of the corresponding tray to indicate when a medical item temperature of that heating assembly has attained or is near the corresponding set point temperature.

Controller 952 is connected to temperature sensors 872, 886, heaters 858, limit switches 865 and indicators 954 of the tray heating assemblies. The controller controls power applied to a heating assembly heater in accordance with a comparison of a temperature measured by a corresponding temperature sensor 872 and a desired temperature entered for that heating assembly and received from system controller 930. In particular, controller 952 receives temperature signals from a heating assembly temperature sensor 872 indicating the temperature of a medical solution container in contact with the sensor (i.e., the container disposed on the heating plate surface). In response to the temperature measured by the temperature sensor being equal to or exceeding a desired temperature entered by a user for that heating assembly, the controller disables power to the corresponding heater. Conversely, when the temperature measured by the temperature sensor is below the desired temperature, the controller enables power to the corresponding heater.

Limit switches 865 of the corresponding tray heating assemblies are each connected to controller 952 and facilitate control of a corresponding heater and residence time measurement in accordance with the presence of a medical solution container on a corresponding heating assembly. Controller 952 monitors the state of the limit switches. For example, this may be accomplished by sending a signal to each switch via a respective circuit and determining the presence of a return signal from that switch. If a limit switch is in a closed state, the respective circuit is completed and the return signal may be detected. When a medical solution container is initially placed on a heating plate, the corresponding limit switch enters a closed state as described above. Accordingly, the heat controller senses this condition and commences measuring elapsed time for the medical item of that heating assembly. The heat controller may store the elapsed time in memory in order to recover and maintain the residence time measurement in the event of a power failure.

The heat controller further prevents enablement of the corresponding heater for a predetermined time interval in response to the limit switch closure. Preferably, the delay time interval is approximately five minutes, however, the time interval may be set to any desired interval. The time delay enables the temperature of a corresponding temperature sensor 872 to approach the temperature of a new medical item received on the heating plate to enhance temperature measurement. Basically, the temperature of the temperature sensor is elevated due to contact with a warmed medical item. When the warmed medical item is removed from the system, the temperature sensor maintains the elevated temperature for a short interval. Thus, the temperature sensor in this state may provide elevated temperature readings relative to the actual temperature of a new unwarmed medical item placed on the heating plate. The time delay enables the temperature sensor to cool and provide accurate temperature measurements. Once the time delay interval has expired, controller 952 controls the corresponding heater as described above.

When the medical item is removed from the heating plate and the limit switch enters an open state, the heat controller detects this condition and resets the time. Further, the heat controller disables the corresponding heater. Thus, when the switch is in an open state indicating no medical item on a heating plate, the timer is reset and the corresponding heater is disabled.

Temperature sensors 886 of the heating assemblies of the corresponding tray are each connected to the heat controller to facilitate disablement of a corresponding heater in response to detecting a temperature in excess of a predetermined threshold as described above. Basically, temperature sensor 886 of a heating assembly provides a temperature indication of the corresponding solution container, heater and/or heating plate to controller 952. The heat controller disables power to the corresponding heater in response to the measured temperature exceeding a predetermined threshold as described above. The heat controller transfers the residence time, medical item temperature, excessive temperature detections and medical item presence information for each heating assembly of the corresponding tray to the system controller for display on display 974 as described above. This information may be transmitted at any desired intervals for display by the system controller. Control circuits 990 and 950 may alternatively be implemented by any conventional circuitry components performing the above described functions.

System 900 includes a configuration similar to that described above for system 100 and may include report unit 101 and/or usage control unit 1001 coupled to system controller 930 to generate, transmit and/or print reports and/or control system usage as described above for system 100. Heating assemblies 805 may each further include an interface 20 in the form of a wireless transmitter/receiver (e.g., RF, infrared, etc.), bar code scanner or connector or port to communicate with a medical item or identify the medical item to system 900 for storage of monitored information as described above.

Operation of system 900 is described with reference to FIGS. 30-33. Specifically, a user selects one or more medical solutions (e.g., bags or bottles containing saline or IV solutions, antibiotics or other drugs, blood, etc.) for heating by the system and determines the appropriate temperature for the solution. The solution container may include the devices described above for solution bag 2. The system may be transported to a desired site. The user subsequently activates power switch 940 and opens door 928. The selected solution containers are placed into the system on any desired heating plates.

Door 928 is subsequently pivoted to a closed state and desired temperatures for the selected solutions are entered into the system via input devices 976 as described above, where the solutions may individually be heated by the heating assemblies to the same or different temperatures. The system controller transmits the set point temperature and other information to heat controllers 952 to control heating and measurement of residence time. The medical solutions within the system may be viewed through the door. In response to placement of a container on a heating plate bottom wall, the container engages corresponding temperature sensor 872 and causes closure of a corresponding limit switch 865. The switch closure is detected by a corresponding heat controller 952 and initiates measurement of elapsed time and the time delay. The heat controller disables the corresponding assembly heater for the predetermined time interval as described above. Once the time delay interval has expired, the heat controller controls the corresponding heater (e.g., enables or disables power to the heater) in accordance with signals from corresponding temperature sensor 872 as described above. The heater applies heat to the corresponding heating plate bottom wall, while the heating plate side walls conduct heat from the bottom wall to evenly distribute heat to the container. A corresponding temperature sensor 886 may be employed to facilitate disablement of the heater in response to excessive heater, heating plate and/or solution temperatures as described above.

Heat controllers 952 transfer the residence time, medical item temperature, excessive temperature detection, medical item presence and other information for the heating assemblies to system controller 930 for display on display 974 (FIGS. 31A-31B). When a medical item on a heating assembly attains or is near a desired temperature, the heat controller illuminates a corresponding indicator 954 as described above. Moreover, system 900 may collect and provide information or reports (e.g., FIGS. 12A-12I) and/or control system usage as described above for system 100, where the reports or information can be transmitted to internal printer 110, display 974 and/or to a local or remote external device (e.g., printer, display, database, medical item, etc.) as described above.

In response to attaining the desired temperature, the container is removed from a heating plate via door 928. The corresponding limit switch subsequently enters an open state, thereby resetting the timer, disabling the corresponding heater and enabling display of a reload or empty indicator for that heating assembly. A new container may be placed on that heating plate, where the limit switch enters a closed state and initiates residence time measurement, delayed heating and display of information to repeat the process for this container. The above process may be repeated for additional containers or medical items. A user may utilize any quantity or combination of heating assemblies in any fashion (e.g., within the same or different trays) to heat medical items within the system.

Figure 34:
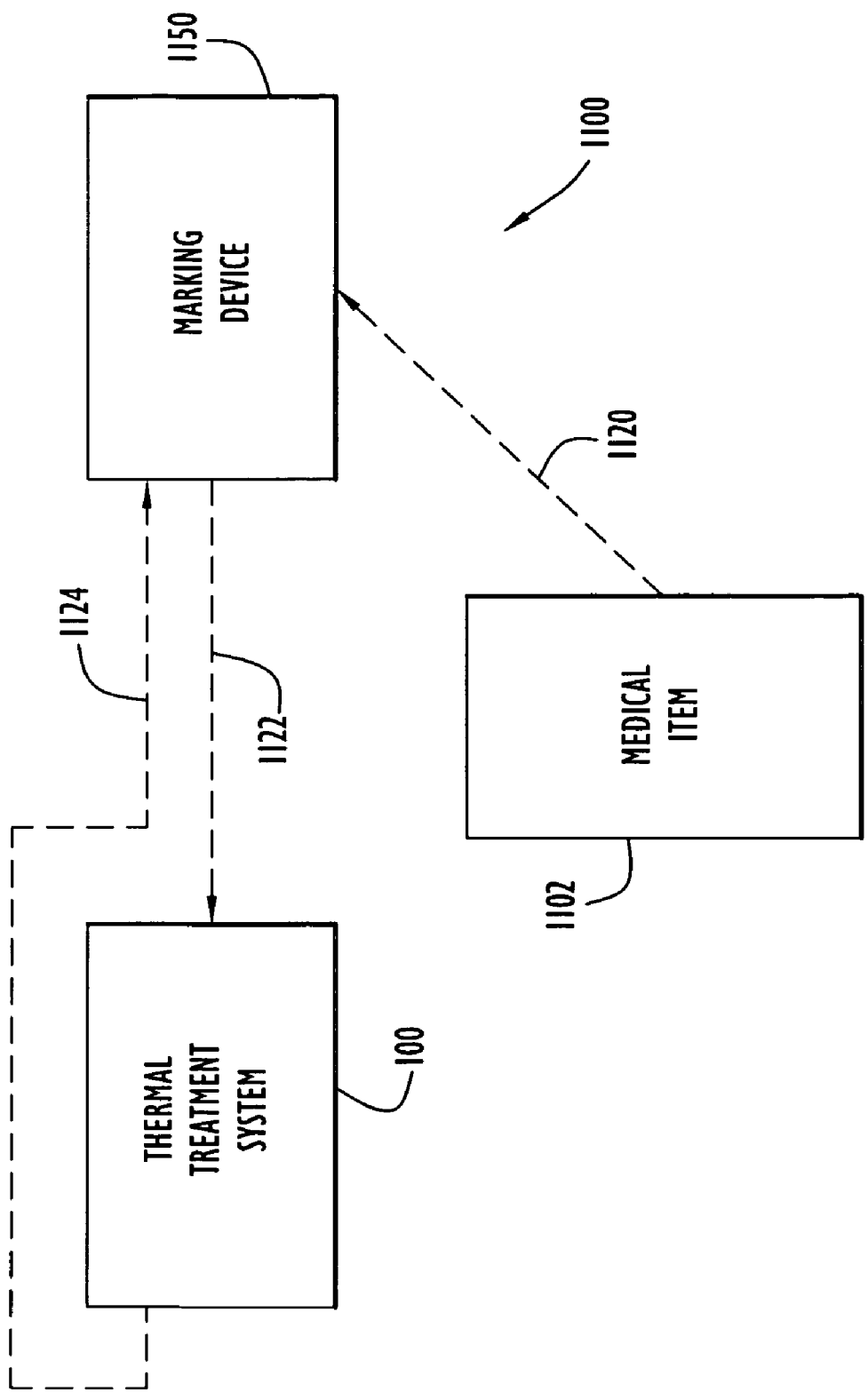
FIG. 34 is a system flow diagram of an exemplary system for placing time stamp information on medical items and thermally treating those items according to the present invention.

In order to further assist medical personnel or users in complying with the prescribed requirements for solution bag 2 or other medical item, the present invention enables marking of the solution bag with condition information as illustrated in FIG. 34. In particular, the present invention includes placing time stamp information (e.g., time and/or date, the patient, solution and/or facility information described above, etc.) on a medical item 1102 (e.g., medical solution containers or bags, etc.) including insertion and/or removal times of the item within a thermal treatment system (e.g., a heating and/or cooling system). The time stamp information may be directly placed on the medical item or be imprinted on a label for attachment to the item as described below. The present invention enables users to readily determine medical item compliance with regulatory and medical item manufacturer requirements relating to medical item heating time, temperature and/or other conditions in order to ensure patient safety.

Specifically, system 1100 includes a marking device 1150 and thermal treatment system 100. The thermal treatment system may be of any of the types of systems described above, especially those accommodating solution bags (e.g., FIGS. 10-11, 13-15, 18, 22, 27A and 30). The marking device produces and places time stamp information on medical item 1102 as described below. The medical item may include any of the devices described above for solution bag 2. The placement of information on the medical item occurs prior to insertion of the medical item within the thermal treatment system. The time stamp information basically pertains to the time the medical item is inserted within the thermal treatment system. Thermal treatment system 100 thermally treats the medical item as described above, where the time stamp information includes the medical item insertion time, thereby enabling users to determine the time interval that the medical item has been thermally treated. This ensures that the medical item is treated for an appropriate time interval to maintain the medical item efficacy as described above. The medical item may further receive time stamp information from the marking device upon removal from the thermal treatment system, thereby providing a record of the thermal treatment time interval (e.g., the time stamp information includes the insertion and removal times) and enabling medical personnel to readily determine the time by which the medical item must be utilized. The marking device may be implemented as a stand-alone device or may be attached to or integral with the thermal treatment system.

System 1100 may be used at any location where medical items are used (e.g., the operating room, emergency room, Pre OP, Post OP, patient's room, home, nursing home, etc.). It is to be understood that the present invention marking system may be utilized with or employ any type of thermal treatment system, such as the ones described above and disclosed in the aforementioned patents, patent publications and patent applications. The present invention marking system is especially suitable for those thermal treatment systems measuring medical item residence time, thereby providing time stamp and residence time information to users or medical personnel to further ensure appropriate thermal treatment intervals for medical items.

Medical item 1102 (FIG. 34) is preferably an intravenous solution bag, but may be a wide variety of medical items (e.g., medical solution containers, saline solutions, IV solutions and/or lines, instruments, blankets, antibiotics or other drugs, blood, irrigation fluid and/or lines, etc.). An exemplary medical item in the form of an intravenous solution bag for use with the present invention and having time stamp information placed thereon is illustrated in FIG. 35A. Specifically, intravenous solution bag 1102 is similar to the bags described above and is preferably implemented by a conventional intravenous solution bag constructed of plastic or other materials commonly utilized for forming those types of bags. The solution bag may contain various types of solutions, such as saline solution, blood, antibiotic or other drugs, or any other intravenously administered solution. Intravenous solution bag 1102 further includes generally triangular projection 4 attached to and extending from the bag upper portion. Projection 4 preferably includes a truncated upper portion having opening or hole 6 defined therein for interfacing an intravenous pole or other support structure (not shown) as described above. The bag lower portion includes outlet 7 and associated fluid conduits 15 to interface an intravenous tube (not shown) and enable the solution to flow through the tube from the outlet to a patient as described above.

Generally, intravenous solutions are required to be within a specific temperature range during infusion to avoid injury to a patient as described above. The solutions typically have a prescribed heating time and utilization life in order to maintain their efficacy as described above. The present invention marking system provides time stamp information for placement on the bag in order to ensure compliance with prescribed requirements (e.g., appropriate heating intervals, etc.). Specifically, time stamp information 1110 may be placed directly on the bag. This may be accomplished by any conventional or other techniques (e.g., a physical impression on the solution bag (with or without ink), a printed indicator by dot matrix, laser printing or thermal techniques, etc.).

Alternatively, time stamp information 1110 can be printed onto a self-adhesive label to be adhered to the solution bag. This label receives time stamp information and is adhered to the bag prior to the bag being placed in the thermal treatment system. The label adhesive may be sufficiently strong to prevent removal of the label from the bag and/or label tampering. The strength of the label adhesive may alternatively enable a user to remove the label from the bag for attachment to a chart. The label may be of any size or shape and may be of any type of printing material (e.g., paper, thermal paper, fabric, etc.). Further, the label may include areas or fields to receive specific time stamp information from the marking device (e.g., entry time into the thermal treatment system, removal time, date, the facility information described above, solution and/or patient, etc.). By way of example only, the time stamp information is placed on the bag adjacent projection 4, however, the time stamp information may be disposed at any location on the bag and be arranged in any fashion to cover areas of any size or shape.

Figure 35B:
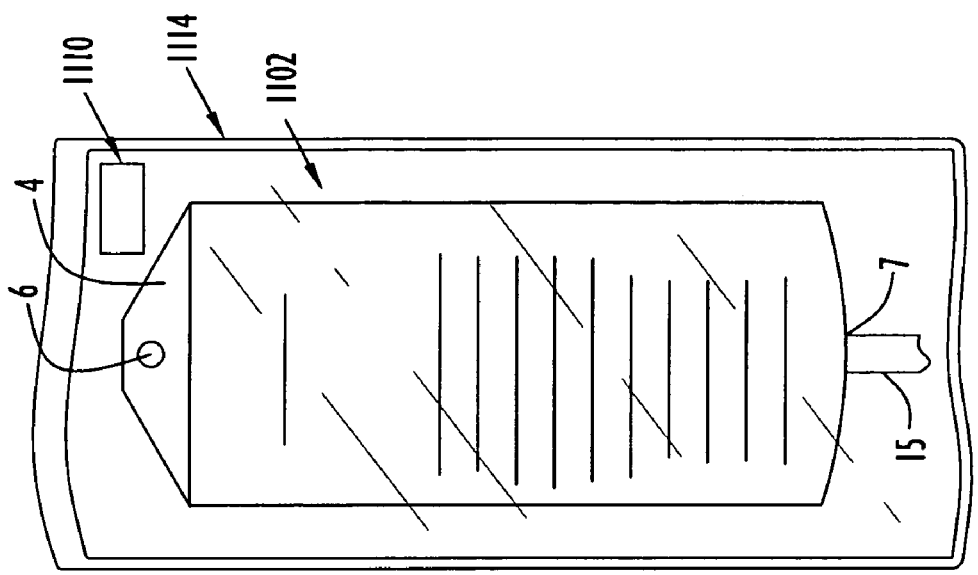
FIG. 35B is a view in elevation of an exemplary medical item in the form of an intravenous solution bag disposed within a liner or overwrap, whereby time stamp information is placed on the liner according to the present invention.
Figure 35A:
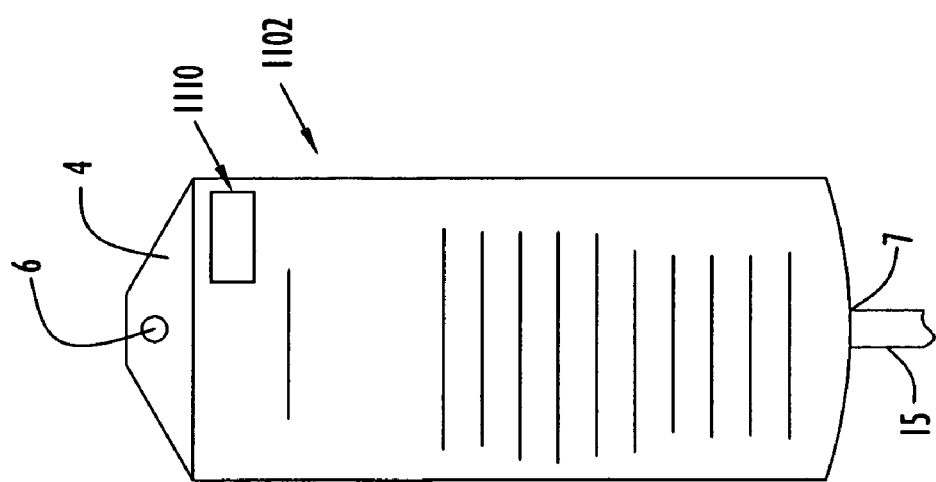
FIG. 35A is a view in elevation of an exemplary medical item in the form of an intravenous solution bag including time stamp information placed on the bag exterior surface according to the present invention.

Intravenous solution bag 1102 may alternatively be encased in a liner or overwrap as illustrated in FIG. 35B. Specifically, intravenous solution bag 1102 is substantially similar to the solution bag described above for FIG. 35A, except that the solution bag is disposed within a liner or overwrap 1114. Liner 1114 may be constructed of any type of plastic or other suitable materials (e.g., materials of the type utilized to form the solution bag), and preferably has dimensions slightly greater than the dimensions of solution bag 2 to receive and house the solution bag. Liner 1114 is preferably sealed along its edges via any conventional or other fastening techniques. The time stamp information may be placed directly on the liner via any conventional or other techniques (e.g., a physical impression on the liner, a printed indicator by dot matrix, laser printing or thermal techniques, etc.) as described above. Alternatively, time stamp information 1110 can be printed onto a self-adhesive label to be adhered to the liner as described above. By way of example only, the time stamp information is placed on the liner toward projection 4, however, the time stamp information may be disposed at any location on the liner.

Figure 36:
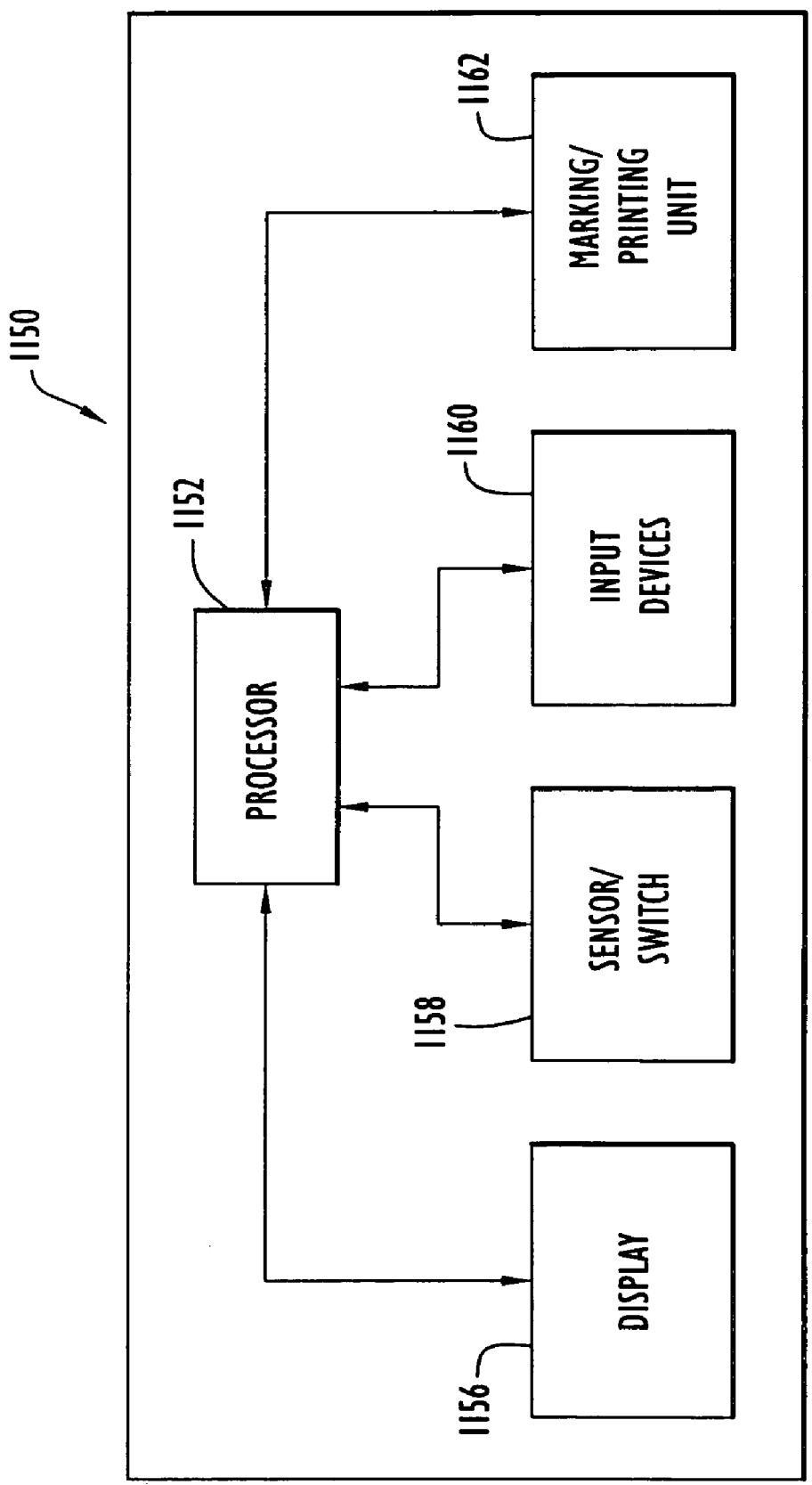
FIG. 36 is a schematic block diagram of a marking device of the system of FIG. 34.

An exemplary marking device employed by the present invention is illustrated in FIG. 36. Specifically, marking device 1150 includes a housing (not shown) including a processor 1152, a display 1156, an article sensor or switch 1158, input devices 1160 and a marking or printing unit 1162. Processor 1152 may be implemented by any conventional or other microprocessor and controls device operation. The processor further maintains time stamp information (e.g., time, date, etc.) for placement on a medical item. The processor is coupled to input devices 1160 typically disposed on the housing exterior to receive information entered by a user. This information may include time and/or date settings, various device parameters and any desired information for the time stamp information (e.g., the facility, patient and/or solution information described above, type of item, etc.). Input devices 1160 may be implemented by any conventional or other input devices (e.g., buttons, keys, switches, keypad, etc.). Display 1156 is coupled to processor 1152 and may be implemented by any conventional or other display (e.g., LED, LCD, etc.). The display is typically disposed on the housing exterior and may provide any desired information to a user (e.g., time stamp information, current date and/or time, etc.).

The marking device housing includes a marking area enabling switch 1158 and printing unit 1162 to engage an article (e.g., medical item or label) for receiving time stamp information. In particular, switch 1158 is coupled to processor 1152 and may be implemented by any conventional or other sensor or switch. The switch provides a signal to the processor to indicate the presence of an article within the marking area to receive time stamp information. Basically, an article is positioned in the marking area to receive time stamp information from the printing unit. The switch is disposed in the marking area in a manner that enables the article to actuate the switch in response to the article positioning. The switch provides a signal to the processor to initiate marking of the article as described below.

Processor 1152 is further coupled to printing unit 1162. The printing unit may be implemented by any conventional or other devices capable of placing the time stamp information on the article. For example, the printing unit may be implemented by a conventional printer to print the time stamp information on the article (e.g., via conventional dot matrix, ink jet, laser printing, and/or thermal printing techniques). Alternatively, the printing unit may be implemented by devices imprinting or impressing (with or without ink) the time stamp information onto the article surface. This may be accomplished via conventional laser or thermal techniques or plate type impressions onto the article. Processor 1152 receives the signal from switch 1158 and initiates the printing unit to place the time stamp information on the article. The time stamp information (or any portion thereof) may further be printed or marked in the form of a bar code or other indicator to enable this information to be scanned for entry into a computer or other system for processing.

Marking device 1150 may alternatively be implemented by any conventional or other marking devices providing time stamp information, such as a Pix-15 available from Amano Electronics, Inc. and the types of devices disclosed in U.S. Pat. Nos. 6,061,303 (Gauthier et al) and U.S. Pat. No. 6,527,462 (Arledge et al), the disclosures of which are incorporated herein by reference in their entireties.

The time stamp information may include any desired information and may be arranged in any desired format. Typically, the time stamp information includes at least the year, day of the year (e.g., month and day) and time of day. The time stamp information may be in the form of text and read by an operator and/or in the form of a bar code or other indicator for scanning by a reader as described above. Labels with time stamp information are illustrated, by way of example only, in FIGS. 37A-37B. Specifically, the labels include an area or field for the time stamp information and are typically pre-printed with descriptive information (e.g., Time/Date In, Time/Date Out, etc.) adjacent the field to indicate to a user the relevancy of the time stamp information. For example, the label in FIG. 37A includes descriptive information (e.g., Time/Date In) indicating that time stamp information 1110 pertains to the insertion time of a medical item into a thermal treatment system. The label of FIG. 37B includes descriptive information (e.g., Time/Date Out) indicating that time stamp information 1110 pertains to the removal time of the medical item from the thermal treatment system. The time stamp information produced by the marking device includes the year (e.g., in a 'YY format (an apostrophe followed by the last two digits of the year)), month (e.g., in a MMM format (the first three letters of the month)), day of the month (e.g., in a DD format (one or two digits)) and time (e.g., with an AM/PM indication followed by an HH:MM format (one or two digits for the hour and two digits for the minutes)). However, the time stamp information may be presented in any desired formats. The time stamp information is placed on each article (e.g., medical item or label) presented to the marking device for marking.

The labels may include any desired quantity of fields with any type of descriptive information. Alternatively, the labels may be blank, where the marking device provides the time stamp and descriptive information. The descriptive information may be provided pre-printed on the label or by the marking device in any combination. Further, the labels may be presented to the marking device for receiving time stamp information, where the stamped labels may subsequently be adhered to the medical item by the user via various techniques (e.g., adhesive, fastener, self-adhesive label, etc.). Alternatively, the medical item may include the label already attached and be presented to the marking device to receive the time stamp information. In addition, the medical item may include any descriptive information and/or fields and may directly receive the time stamp information from the marking device (e.g., via printing or impression techniques) at any desired locations as described above.

Operation of the system is described with reference to FIG. 34. Specifically, medical item 1102, preferably a solution bag, is initially retrieved for a medical procedure. The bag may include any of the devices or indicia described above for solution bag 2. The bag is typically required to have the desired utilization temperature prior to use as described above. When the bag requires thermal treatment to attain the desired utilization temperature, the bag is received by marking device 1150 at flow 1120. The marking device maintains time stamp information (e.g., time, date, the facility, patient and/or solution information described above, etc.) and may place any desired information (e.g., typically time and date information) directly on the bag as described above. Alternatively, the marking device may place this information on a label for attachment to the bag as described above.

Once the time stamp information has been placed on the bag, the bag is disposed within thermal treatment system 100 at flow 1122. The time stamp information placed on the bag basically pertains to the time the bag is placed in the thermal treatment system. The thermal treatment system is operated to thermally treat the bag to a desired temperature suitable for use in the medical procedure as described above. The medical item and/or thermal treatment system may measure, collect, transmit and/or print medical solution information locally or externally as described above. The time stamp information enables users to determine the heating or residence time of the bag within the system in order to ensure the bag is heated for an appropriate time interval to comply with prescribed procedures and maintain its efficacy.

When the bag has attained a desired temperature, the bag is removed from thermal treatment system 100 for utilization in the medical procedure. Alternatively, the bag may be removed from the thermal treatment system and be received by marking device 1150 at flow 1124 in order to provide further time stamp information on the bag (or label) pertaining to removal of the bag from the thermal treatment system. This additional time stamp information provides a record of the bag heating time.

The present invention thus provides monitoring conditions of medical solution or other medical items at each and/or any stage during the life of that item from manufacture to disposal (e.g., from manufacturing, through storage prior to and/or during transport, through storage at an intended facility, through thermal treatment at a facility, etc.). Accordingly, the precise status of the medical solution with respect to prescribed requirements (e.g., medical regulations or standards, manufacturer requirements, etc.) may be indicated to users and/or medical personnel to prevent non-compliant items from being utilized or administered to patients.

It will be appreciated that the embodiments described above and illustrated in the drawings represent only a few of the many ways of implementing medical item thermal treatment systems and method of monitoring medical items for compliance with prescribed requirements.

The present invention medical items and thermal treatment systems may be utilized individually or in any combination to monitor any types of medical items for compliance with any types of requirements (e.g., manufacturer, medical personnel, medical standard or regulation, etc.). The present invention may monitor the items and/or indicate the status (e.g., compliance or non-compliance with prescribed requirements) to any users or medical personnel through each or any of the stages of the medical item life (e.g., from manufacture through use and/or disposal).

The monitoring device may be of any quantity, shape or size and may be disposed at any location on or within the medical item via any conventional or other techniques (e.g., adhesive, welding, lamination, floatation devices for placement in solution, etc.). The monitoring device may include any quantity of any types of conventional or other sensors (e.g., proximity sensors, pressure sensors, temperature sensors (e.g., RTD, infrared, etc.), presence sensors, weight sensors, volume sensors, flow sensors, fluid sensors, fluid level sensors, etc.) to measure and provide any information. The processor may be implemented by any conventional or other microprocessor. Software for the processor may be implemented in any desired computer language and could be developed by one of ordinary skill in the computer arts based on the functional descriptions contained herein. The processor may alternatively be implemented by any type of hardware, software and/or other processing circuitry, and may be available pre-programmed for immediate use. The various functions of the processor may be distributed in any manner among any quantity of software modules, processors and/or circuitry. The algorithms and/or processes described above may be modified in any manner that accomplishes the functions described herein.

The monitoring device may compare measured values or other information to any desired requirements to indicate compliance with those requirements. For example, the monitoring device may examine the record of medical item conditions and determine and/or indicate that the medical item has been previously warmed (e.g., based on recorded temperatures) to prevent re-warming of the medical item. Further, the monitoring device may determine and/or indicate when the medical item has been inserted into and/or removed from a thermal treatment system (e.g., based on temperature variations in the record) and/or the subsequent time within which the item must be used (e.g., medical items may have a use time after thermal treatment). Moreover, the monitoring device monitors medical item conditions during storage (or non-use) to ensure that higher temperature exposure does not accelerate changes in the item (e.g., efficacy) and/or that the medical item remains pharmaceutically acceptable. In addition, the monitoring device may examine fluid level information (e.g., in the record or as the information is being measured) to indicate the amount of fluid or when a particular dosage has been administered. The monitoring device may indicate any conditions on the display and/or indicators.

The display may be of any quantity, size or shape, may be implemented by any conventional or other display (e.g., LCD, LED, etc.) and may display any desired information. The display may be disposed at any desired location on the medical item and utilize any symbols or characters (e.g., alphanumeric, punctuation, icons, etc.) to indicate compliance with conditions. The indicators may be of any quantity or type (e.g., LEDs or other illuminating devices of any colors, etc.) and may be disposed at any desired locations on the medical item. Any quantity of indicators may be associated with a particular condition and may be illuminated or actuated in any fashion (e.g., brightness, flashing, colors, etc.) to indicate that condition. Further, the monitoring device may include any quantity of any type of visual and/or audio indicators (e.g., speech synthesis, beep, buzzer, etc.) to indicate conditions.

The interface may be implemented by any conventional or other interface (e.g., wireless, RF, infrared, cable, connector, etc.) and utilize any desired protocol to communicate with an external device. The external device may be in the form of any processing device (e.g., computer system, hand-held receiver, PDA, etc.) to communicate with and retrieve information from the monitoring device. The external device may provide any desired information to the monitoring device (e.g., entered by a user, etc.). The external device may store retrieved information in any type of storage unit (e.g., file, local or remote database or other memory or storage unit, etc.) for access by users for any desired purposes (e.g., tracking, inventory, reviewing item history, etc.). The monitoring device may include any type of location devices (e.g., GPS, homing device, transmitter, etc.) to provide location information for the medical item. The monitoring device may utilize any quantity of any type of power source (e.g., batteries, etc.) and may include a unique identifier of any desired length of any types of characters or symbols (e.g., alphanumeric, etc.). The monitoring device may be disposable with the medical item or re-programmed for use with subsequent medical items.

The memory device may be of any quantity, shape or size and may be disposed at any location on or within the medical item via any conventional or other techniques (e.g., adhesive, welding, lamination, floatation devices for placement in solution, etc.). The memory device processor may be implemented by any conventional or other microprocessor. Software for the processor may be implemented in any desired computer language and could be developed by one of ordinary skill in the computer arts based on the functional descriptions contained herein. The processor may alternatively be implemented by any type of hardware, software and/or other processing circuitry, and may be available pre-programmed for immediate use. The various functions of the processor may be distributed in any manner among any quantity of software modules, processors and/or circuitry. The algorithms and/or processes described above may be modified in any manner that accomplishes the functions described herein.

The processor may compare measured values or other information to any desired requirements to indicate compliance with those requirements. For example, the memory device may examine the record of medical item conditions and determine and/or indicate that the medical item has been previously warmed (e.g., based on recorded temperatures) to prevent re-warming of the medical item. Further, the memory device may determine and/or indicate when the medical item has been inserted into and/or removed from a thermal treatment system (e.g., based on received information or temperature variations in the record) and/or the subsequent time within which the item must be used (e.g., medical items may have a use time after thermal treatment). Moreover, the memory device enables monitoring of medical item conditions to ensure that higher temperature exposure does not accelerate changes in the item (e.g., efficacy) and/or that the medical item remains pharmaceutically acceptable. The memory device may indicate any conditions on the display and/or indicators.

The memory device display may be of any quantity, size or shape, may be implemented by any conventional or other display (e.g., LCD, LED, etc.) and may display any desired information. The display may be disposed at any desired location on the medical item and utilize any symbols or characters (e.g., alphanumeric, punctuation, icons, etc.) to indicate compliance with conditions. The memory device indicators may be of any quantity or type (e.g., LEDs or other illuminating devices of any colors, etc.) and may be disposed at any desired locations on the medical item. Any quantity of indicators may be associated with a particular condition and may be illuminated or actuated in any fashion (e.g., brightness, flashing, colors, etc.) to indicate that condition. Further, the memory device may include any quantity of any type of visual and/or audio indicators (e.g., speech synthesis, beep, buzzer, etc.) to indicate conditions.

The memory device interface may be implemented by any conventional or other interface (e.g., wireless, RF, infrared, cable, connector, etc.) and utilize any desired protocol to communicate with an external device. The external device may be in the form of any processing device (e.g., thermal treatment system, computer system, hand-held receiver, PDA, etc.) to communicate with and retrieve and/or provide information. The external device may provide any desired information to the memory device (e.g., entered by a user, etc.). The external device may further store information in any type of storage unit (e.g., file, local or remote database or other memory or storage unit, etc.) for access by users for any desired purposes (e.g., tracking, inventory, reviewing item history, etc.). The memory device may utilize any quantity of any type of power source (e.g., batteries, etc.) and may include a unique identifier of any desired length of any types of characters or symbols (e.g., alphanumeric, etc.). The memory device may be disposable with the medical item or re-programmed for use with subsequent medical items.

The bar code and/or transponder unit may be of any quantity, shape or size and may be disposed at any location on or within the medical item via any conventional or other techniques (e.g., adhesive, welding, lamination, floatation devices for placement in solution, etc.). The transponder unit processor may be implemented by any conventional or other microprocessor. Software for the processor may be implemented in any desired computer language and could be developed by one of ordinary skill in the computer arts based on the functional descriptions contained herein. The processor may alternatively be implemented by any type of hardware, software and/or other processing circuitry, and may be available pre-programmed for immediate use. The various functions of the processor may be distributed in any manner among any quantity of software modules, processors and/or circuitry. The algorithms and/or processes described above may be modified in any manner that accomplishes the functions described herein.

The transceiver may be implemented by any conventional or other transceiver (e.g., wireless, RF, infrared, cable, connector, etc.) to communicate with the thermal treatment system or other external device (e.g., processing device or system, computer system, hand-held receiver, PDA, etc.). The thermal treatment system or other external device may provide any desired information to the transponder unit (e.g., entered by a user, etc.). The thermal treatment system or other external device may store information in any type of storage unit (e.g., file, local or remote database or other memory or storage unit, etc.) for access by users for any desired purposes (e.g., tracking, inventory, reviewing item history, etc.). The thermal treatment system or other external device may compare measured values or other information to any desired requirements to indicate compliance with those requirements. For example, the thermal treatment system or other external device may examine the record of medical item conditions and determine and/or indicate that the medical item has been previously warmed (e.g., based on recorded temperatures) to prevent re-warming of the medical item. Further, the thermal treatment system or other external device may determine and/or indicate when the medical item has been inserted into and/or removed from a thermal treatment system (e.g., based on information from the thermal treatment system or temperature variations in the record) and/or the subsequent time within which the item must be used (e.g., medical items may have a use time after thermal treatment). Moreover, the thermal treatment system or other external device monitors medical item conditions to ensure that higher temperature exposure does not accelerate changes in the item (e.g., efficacy) and/or that the medical item remains pharmaceutically acceptable. The thermal treatment system or external device may indicate any conditions via a display and/or indicators. The thermal treatment system or external device may include any quantity of any type of visual and/or audio indicators (e.g., speech synthesis, beep, buzzer, etc.) to indicate conditions.

The transponder unit may utilize any quantity of any type of power source (e.g., batteries, etc.). The bar code and transponder unit may provide a unique identifier of any desired length of any types of characters or symbols (e.g., alphanumeric, etc.). The transponder unit may be disposable with the medical item or re-programmed for use with subsequent medical items.

The ink cells may be of any quantity of any type of conventional or other ink cells. The ink cells may be disposed at any desired locations on the medical item in any desired arrangement. The cells may alternatively be disposed in any fashion on any quantity of labels of any shapes or sizes and adhered or disposed on the medical item at any desired locations. Any quantity of cells may be associated with a particular condition and may be activated in any fashion (e.g., change colors, dark to light, light to dark, etc.) to indicate that condition. The ink cells may be utilized to indicate any desired conditions.

The control circuit may be disposed on or remote from the medical item. The control circuit or external device (e.g., thermal treatment system, processing system or device, transport container or housing, etc.) may include any quantity of any types of conventional or other sensors (e.g., proximity sensors, pressure sensors, temperature sensors (e.g., RTD, infrared, etc.), presence sensors, weight sensors, volume sensors, flow sensors, fluid sensors, fluid level sensors, etc.) to measure and provide any information. The control circuit processor may be implemented by any conventional or other microprocessor. Software for the processor may be implemented in any desired computer language and could be developed by one of ordinary skill in the computer arts based on the functional descriptions contained herein. The processor may alternatively be implemented by any type of hardware, software and/or other processing circuitry, and may be available pre-programmed for immediate use. The various functions of the processor may be distributed in any manner among any quantity of software modules, processors and/or circuitry. The algorithms and/or processes described above may be modified in any manner that accomplishes the functions described herein.

The processor may compare measured values or other information to any desired requirements to indicate compliance with those requirements. For example, the control circuit (or external device) may examine the record of medical item conditions and determine and/or indicate (e.g., via the ink cells) that the medical item has been previously warmed (e.g., based on recorded temperatures) to prevent re-warming of the medical item. Further, the control circuit (or external device) may determine and/or indicate (e.g., via the ink cells) when the medical item has been inserted into and/or removed from a thermal treatment system (e.g., based on information from a thermal treatment system or temperature variations in the record) and/or the subsequent time within which the item must be used (e.g., medical items may have a use time after thermal treatment). Moreover, the control circuit (or external device) may monitor medical item conditions during storage (or non-use) to ensure that higher temperature exposure does not accelerate changes in the item (e.g., efficacy) and/or that the medical item remains pharmaceutically acceptable. The control circuit (or external device) may indicate any conditions on the display and/or indicators.

The clip may be implemented by any quantity of any type of connector to connect the cells to the external device or control circuit. The clip may be disposed at any location on the medical item. The cells may be manually activated by any quantity of any type of actuator (e.g., button, switch, etc.) disposed at any locations on or remote from the medical item. The ink cells and/or control circuit may utilize any quantity of any type of power source (e.g., batteries, etc.).

Thermal treatment system 100 may include any conventional or other heating and/or refrigeration units to thermally treat the medical items to any desired temperature. The monitoring sensors may be implemented by any quantity of any conventional or other sensors (e.g., proximity sensors, pressure sensors, temperature sensors (e.g., RTD, infrared, etc.), presence sensors, weight sensors, volume sensors, flow sensors, fluid sensors, fluid level sensors, etc.) to measure and provide any desired information to the report controller and/or usage control unit and may be disposed at any location. The system may be powered by any conventional or other power source (e.g., AC, DC, wall outlet jack, batteries, etc.).

The temperature controller may be implemented by any quantity of any conventional or other temperature controller or processor (e.g., chip, card, processor, circuitry, etc.) and include any quantity of any desired input devices (e.g., buttons, keypad, etc.). The temperature controller may control the heater/cooler units to any desired temperature range, and may utilize any quantity of set points (e.g., maximum and/or minimum, etc.). The system may record any type of information (e.g., date and time of thermal treatment disablement and enablement, fluid level or loss, etc.) relating to system operation for subsequent retrieval, analysis, display, display/report (e.g., date and time of thermal treatment disablement and enablement, fluid level or loss, etc.) and control functions supported by the system.

The report controller may be implemented by any conventional or other microprocessor or controller (e.g., chip, card, processor, circuitry, etc.) and include any quantity of any desired input devices (e.g., buttons, keypad, etc.). The report controller may maintain the date, elapsed heating/cooling time and/or occurrence time of any event or condition (e.g., time medical items are inserted and/or removed within the system, etc.). The report controller may measure the elapsed time or record an occurrence time for any desired condition. The report controller may maintain the time information internally or utilize any desired external circuitry (e.g., a timer, etc.).

The report controller may collect any desired information (e.g., start date and time of solution or other item heating/cooling, the time interval the solution or other item was heated/cooled, the temperature the solution or other item attained during heating/cooling, temperature of the solution or other item when the solution was removed from the system, amount or quantity of solution or other item residing, placed in or removed from the system, partial or complete history of time and solution or other item temperature measured at any desired time intervals, facility information, patient information, doctor information, type of procedure, solution information, type of instruments or other item being heated/cooled, amount or quantity of solution or other item being heated/cooled, etc.) from any desired sources (e.g., temperature controller, user, memory, another computer or device, etc.). The report controller may implement or be implemented by the temperature controller. The monitoring sensors may be coupled to the temperature controller, system interface and/or report controller either individually or in any combination or fashion.

The reports may be arranged in any fashion and include any desired information. The date, time and other information may be in any desired format (e.g., month, day and year, hours and minutes, text, numeric, icons, etc.). The report information may be arranged and/or presented (e.g., printed, displayed, etc.) in any desired formats (e.g., text, charts, graphs, columns, rows, tables, etc.) and in any order or arrangement. The graph may include any quantity of axes each associated with any desired information (e.g., time, temperature, etc.) in any desired scales or units (e.g., Celsius, Fahrenheit, etc.). The graphs may utilize any types of symbols or characters (e.g., dots, diamonds, dashes, alphanumeric characters, punctuation symbols, etc.) to indicate points on the graph. The graphs may indicate time, temperature or events (e.g., removal of solution, etc.) in any fashion. The reports may provide information (e.g., temperature, etc.) measured or collected at any desired preset or user specified time intervals (e.g., hours, minutes, seconds, etc.). The time intervals may be specified by a user via any input devices (e.g., temperature or report controller input devices (e.g., keys, buttons, etc.), remote or local computer, etc.). The report and/or information may alternatively be stored in a local or remote database or memory device (e.g., local memory, removable memory, etc.) for later retrieval. The reports may include a pre-arranged format or may be programmable or selected by a user via report controller input devices. The system, controller and other displays may be of any quantity, shape or size, may be disposed at any location on or remote from the system, may be implemented by any conventional or other displays (e.g., LED, LCD, etc.) and may display any desired information. The information displayed may be selected via temperature controller or report controller input devices, or the display may include display controls (e.g., buttons, keys, etc.).

The internal printer may be implemented by any conventional or other printing device, may be local or remote, may serve any quantity of systems or other devices, and may produce reports on any desired medium (e.g., paper, labels, etc.). The reports may be printed and/or displayed concurrently with system operation as report data is collected or at any specific time or in response to user entered information (e.g., a print command or key). The report may be printed at any desired time before, during or after system use, and may be retrieved from the system at any desired time or in any desired manner that preserves a sterile field (e.g., after completion of the medical procedure, times when a sterile field is not needed or being employed by the system, etc.). The system or report controller may include any conventional or other communications device or module (e.g., modem, etc.) and may download or transfer an electronic form of the report to any desired device (e.g., PDA, computer, another system, etc.) at any specific time or in response to user entered information (e.g., transmit command or key). The system may further be networked to enable retrieval of reports and/or information from a station coupled to the network. The printer and displays may be disposed at any suitable locations on or remote from the system. Alternatively, the system may be implemented to generate reports without the printer and/or display. Any desired information may be transmitted between the system components (e.g., temperature controller, report controller, printer, displays, etc.) via any conventional or other communications medium or protocols (e.g., hardwire, wireless, network, etc.).

Software for the temperature controller and report controller may be implemented in any desired computer language and could be developed by one of ordinary skill in the computer arts based on the functional descriptions contained herein. The temperature controller and/or report controller may alternatively be implemented by any type of hardware and/or other processing circuitry, and may be available pre-programmed for immediate use. The various functions of the temperature controller and/or report controller may be distributed in any manner among any quantity of software modules, processors and/or circuitry.

The system interface, computer interface and communications device of the usage control unit may be implemented by any quantity of any conventional or other microprocessor or controller (e.g., chip, card, processor, circuitry, etc.) and include any quantity of any desired input devices (e.g., buttons, keypad, etc.). The computer interface may be in the form of a read/write unit to transfer information to the computer system. The system and computer interfaces may be of any quantity and accommodate any quantity of information devices. The communications device may include any quantity of any conventional or other devices (e.g., modem, router, etc.) for communications with the network or other devices. The system interface and communications device may maintain the date, elapsed heating/cooling time and/or occurrence time of any event or condition (e.g., time medical items are inserted and/or removed within the system, etc.) and may measure the elapsed time or record an occurrence time for any desired condition. The system interface and communications device may maintain the time information internally or utilize any desired external circuitry (e.g., a timer, etc.).

The system interface and communications device may collect any desired information (e.g., the date/time that a medical item was placed into/removed from the medical item warming/cooling system, the temperature of the medical item upon being placed into/removed from the medical item warming/cooling system, the temperature of the medical item at specific points in time while stored in the medical item warming/cooling system, start date and time that the medical item began to be heated/cooled, the length of time that the medical item was heated/cooled, the temperature that the medical item was heated/cooled to during the heating/cooling cycle and/or the amount of solution or other item residing, placed in or removed from the system, patient information, thermal treatment system information (e.g., type, identification or serial number, etc.), user information (e.g., access or account identification or code, passwords, etc.), facility information, doctor information, the type of procedure, solution information, the type of item being heated/cooled, the amount or quantity of fluid or other item being heated/cooled (e.g., fluid (or other item) level, volume or weight), the flow rate of fluid that is being heated/cooled, the pressure of fluid flow as the fluid is heated/cooled and any other desired information) from any desired sources (e.g., temperature controller, user, memory, another computer or device, etc.). Information (e.g., user, system, facility, patient and/or doctor information, etc.) may be pre-stored on the information device and/or entered by a user via system, interface or communication device input devices (e.g., keypad, etc.). The recordation or collection of information may occur automatically or via user entered information (e.g., start, stop and/or record keys). The system interface and/or communications device may implement or be implemented by the temperature controller. The monitoring sensors may be coupled to the temperature controller, report unit, system interface and/or communications device either individually or in any combination or fashion.

The information device may be of any shape or size, may be implemented by any type of device including any type of memory or storage (e.g., a microprocessor with memory, a chip, a floppy, magnetic or optical disk, CD-ROM, USB disk, smart card, etc.) and may contain any desired information. The information device may include any pre-stored information and may be coupled to the thermal treatment system, computer system, system interface or computer interface via any conventional or other techniques (e.g., direct connection, infrared, RF transmission, cellular, Bluetooth, etc.). The system interface, communications device and/or computer interface may be disposed internal or external of the respective thermal treatment and computer systems. The system interface may further be in communication with a local or remote computer system (e.g., via network, cables, wireless transmission, etc.) to transfer and receive information (without use or in addition to the computer interface).

The system and computer interfaces may engage or receive the information device in any fashion. The information device may include any storage and/or processing capabilities. For example, the information device may perform the functions of the system interface, where the system interface in this case basically couples the information device to the thermal treatment system (e.g., temperature controller and/or sensors). The information device may include any degree of intelligence, where the functions of the system interface may be distributed in any fashion among the system interface and information device. Further, the information device may include processing to generate desired reports and displays for transfer to other devices (e.g., computer systems, monitors, etc.). The information device may be removable with respect to the thermal treatment system, system interface and computer interface and may be transported between the devices in any fashion (e.g., the user, mechanical devices, etc.).

Use of a medical item thermal treatment system can be authorized based upon any single or combination of quantifiable authorized use parameters or metrics (e.g., a calendar/time period during which the medical item thermal treatment system is authorized for use, a number of warming/cooling cycles for which the medical item thermal treatment system is authorized for use, a number of medical items for which the medical item thermal treatment system is authorized for use, type of use (e.g., heating, cooling, heating and cooling, etc.), maximum number of medical items, power usage, etc.). Authorized use can be associated with a user authorization code or password that can include any number, character string, array, or combination thereof that is interpreted by a medical item thermal treatment system to authorize or limit use of any capability or function supported by the medical item thermal treatment system.

Operational or control parameters used to control operation of the medical item thermal treatment system can include any parameter that can be used to specify an operational instruction or performance characteristic (e.g., a user access code, type of medical item accepted, a desired temperature for medical items, a maximum duration that a medical item (e.g., IV solution, blood, etc.) is allowed to remain in the thermal treatment system, time and/or temperature thresholds to be used in controlling alarms, log event definitions, timeouts, timer periods, various threshold values, log messages, storage destinations, etc.). Temperature profiles can be used as control parameters to control the rate of temperature increase/decrease and manner of maintaining the temperature of any medical item. Alert thresholds can be used as control parameters to control the issuance of alarms and/or to initiate a response (e.g., storing critical information, disabling a warming/cooling unit, etc.). The alert thresholds may be within any desired range of an alert condition (e.g., temperature, exhaustion of use, etc.). The systems may include any type of visual and/or audio alarms (e.g., lights, beeps, flashes, synthesized voice, etc.) disposed at any suitable locations. Data collection instructions can be used as control parameters to control what sensor information is stored, the format in which it is stored, how often the information is polled and/or stored, and/or where information is to be stored. Display parameters can be used as control parameters to control the content and arrangement of generated displays and reports. Alternatively, the thermal treatment systems may receive the usage and control parameters in any desired fashion (e.g., from a remote or local computer or other device, from user entry via input devices, etc.).

Displays and reports can be generated by any number of local and/or remote devices with access to the collected or stored thermal treatment system information. Displays and reports can be generated by any number of special purpose or generic display and report generators. A generated display or report can be presented to a user via the same device that generates the display or report and/or at one or more locally or remotely located display or printing devices. The displays and reports may be arranged in any fashion and include any desired information. Date, time and other display or report information may be in any desired format (e.g., month, day and year, hours and minutes, text, numeric, icons, etc.). The display or report information may be arranged and/or presented (e.g., printed, displayed, etc.) in any desired formats (e.g., text, charts, graphs, columns, rows, tables, etc.) and in any order or arrangement. The graph may include any quantity of axes each associated with any desired information (e.g., time, temperature, etc.) in any desired scales or units (e.g., Celsius, Fahrenheit, etc.). The graphs may utilize any types of symbols or characters (e.g., dots, diamonds, dashes, alphanumeric characters, punctuation symbols, etc.) to indicate points on the graph. The graphs may indicate time, temperature or events (e.g., removal of solution, etc.) in any fashion. The displays and reports may provide information (e.g., temperature, etc.) measured or collected at any desired preset or user specified time intervals (e.g., hours, minutes, seconds, etc.). The time intervals may be specified by a user via any input devices (e.g., temperature controller, system interface and/or communications device input devices (e.g., buttons, keys, etc.), remote or local computer, etc.). The display, report and/or information may alternatively be stored in a local or remote database or memory device (e.g., local memory, removable memory, etc.) for later retrieval. The displays and reports may include a pre-arranged format or may be programmable or selected by a user via temperature controller, system interface and/or communications device input devices. The information displayed may be selected via temperature controller, system interface and/or communications device input devices, or the display may include display controls (e.g., buttons, keys, etc.).

The external printer may be implemented by any conventional or other printing device, may be local or remote, may serve any quantity of systems or other devices, and may produce displays and/or reports on any desired medium (e.g., paper, labels, etc.). The displays and reports may be printed and/or displayed concurrently with system operation as display and report data is collected or at any specific time or in response to user entered information (e.g., a print command or key). The display and/or report may be printed at any desired time before, during or after system use. The system and/or information device may download or transfer information to any desired device (e.g., PDA, computer, another system, etc.) at any specific time or in response to user entered information (e.g., transmit command or key). The system may further be networked to enable retrieval of information from a station coupled to the network. The printer and displays may be disposed at any suitable locations on or remote from the system. Alternatively, the system may be implemented to generate displays and/or reports without the printer and/or display. Any desired information may be transmitted between the system components (e.g., temperature controller, system and computer interfaces, communications device, information device, computer and server systems, printer, displays, etc.) via any conventional or other medium or protocols (e.g., hardwire, wireless, network, etc.).

The computer systems and server systems may be implemented by any type of personal or other computer or processing system having any suitable platform or operating system. The computer system may include any commercially available operating system (e.g., Windows, OS/2, Unix, Linux, DOS, etc.), any commercially available and/or custom software (e.g., communications software, display and/or report generation software, etc.) and any types of input devices (e.g., keyboard, mouse, microphone, voice recognition, etc.). The information stores may be implemented by any conventional database or other storage structures (e.g., files, data structures, tables, etc.) or devices and may include information stored in any number of files using any file format.

Software for the system devices (e.g., temperature controller, system interface, communications device, etc.) may be implemented in any desired computer language and could be developed by one of ordinary skill in the computer arts based on the functional descriptions contained herein and the flow charts illustrated in the drawings. The temperature controller, system interface and/or communications device may alternatively be implemented by any type of hardware and/or other processing circuitry, and may be available pre-programmed for immediate use. The various functions of the temperature controller, system interface, computer interface and communications device may be distributed in any manner among any quantity of software or hardware modules, computer systems, processors and/or circuitry. Further, any references herein of software performing various functions generally refer to computer systems or processors performing those functions under software control. The computer system may alternatively be implemented by hardware or other processing circuitry. The various functions of the present invention usage control may be distributed in any manner among any quantity (e.g., one or more) of hardware and/or software modules or units, computer or processing systems or circuitry, where the computer or processing systems may be disposed locally or remotely of each other and communicate via any suitable communications medium (e.g., LAN, WAN, Intranet, Internet, hardwire, modem connection, wireless, etc.). The software and/or processes described above and illustrated in the flow charts and diagrams may be modified in any manner that accomplishes the functions described herein.

Thermal treatment system 100 may be a stand-alone system or may be coupled to any number of workstation computers, server computers or data storage devices via any communications medium (e.g., network, modem, direct connection, etc.). Authorized use and control parameters can be transferred via a communications network or via transportable storage devices (e.g., floppy disk, CD ROM, DVD, zip drive disk, etc.).

Software used to access and display medical item thermal treatment system information bases may be installed upon local or remote devices and executed on a computer system in any conventional or other manner (e.g., an install program, copying files, entering an execute command, etc.). The functions associated with the present invention (e.g., storing/retrieving monitored information, updating authorized use and/or control parameters, etc.) may be performed on any quantity of computers or other processing systems. Further, the specific functions may be assigned to one or more of the computer systems in any desired fashion.

A user may interact with the medical item thermal treatment system and information device (e.g., related monitored/logged data, authorized use and control parameters, etc.) via any style of user interface (e.g., a command line interface, a menu, a database interface, graphical user interface, web site, etc.) on a local or remote computer or server system. The user interface may include any desired information arranged in any format or fashion. Access for information retrieval and/or processing may be controlled by any conventional or other techniques (e.g., accounts, subscriptions, passwords, identifications, etc.). Interfaces used can be commercially available interfaces or developed especially for use in connection with a medical item thermal treatment system and/or medical item thermal treatment system information base.

Thermal treatment system 100 can be implemented by any number of controllers, modules and/or units and is not limited to the architecture described above. Payment for use of the medical item thermal treatment system may be arranged in any fashion (e.g., telephone transaction, electronic transaction, billings by mail, online via a website or local or remote computer or server system, etc.) with a service provider or other party.

Temperature control system 700 and corresponding components may be of any size or shape and may be constructed of any suitable materials. The controller, fuses, power switches and labels may be disposed on the system at any suitable locations. The system may include any quantity of each component, while the components (e.g., cabinet, circuitry, drawers, etc.) may be arranged in any fashion. The temperature control system may include any quantity (e.g., at least one) of drawers with each drawer having any quantity (e.g., at least one) of sub-compartments. The drawers may be of any size or shape and may be constructed of any suitable materials. The drawers may include any conventional or other handle disposed at any location, and may include any conventional or other pivoting or sliding mechanisms to facilitate placement and removal of drawers and items within the systems. The drawer sub-compartments may be of any quantity, size or shape, while the drawers and sub-compartments may each contain any quantity of any types of medical items. The drawers may include a window of any shape or size, or be implemented without a window. The window may include any type of transparent or translucent material, and may be defined at any suitable locations on the drawer, door or cabinet. Further, the drawers may be implemented by any types of drawers that are capable of being placed and removed within the system (e.g., substantially horizontal drawers, such as those in common desks), while the system may include any quantity or combination of different types of drawers. Moreover, the drawers, sub-compartments or other receptacles may be disposed within the cabinet interior chambers on shelves or other structures for receiving the medical items.

The temperature sensor of system 700 may be implemented by any conventional resistive or other type of temperature sensing device, and may be disposed at any location on the drawer or cabinet interior. The heating element may include any type of configuration covering the entirety or a portion of the drawer bottom wall (e.g., strips, bars, segments, include various openings, etc.). The heating element may be implemented by any quantity of conventional or other types of heating devices (e.g., heating coils, conduction, convection, microwave or other radiation, etc.), and may be disposed on the drawer at any locations. The heating element may include any type of conventional or other connector to facilitate heating element connections, and may be fastened to the drawer via any conventional or other fastening techniques (e.g., adhesives, brackets, etc.).

The control circuit components (e.g., power switch, relays, fuses, controller, power source, connection terminal, etc.) of system 700 may be implemented by any quantity of any conventional or other electrical components arranged in any fashion and performing the functions described above. The circuits may be disposed at any location on or within the housings and may be arranged in any fashion to control heating of the drawers as described above. The relays may be implemented by any conventional solid state or other type of relay device. Similarly, the cut-out switch may be implemented by any conventional or other type of switching or power-limiting device. The fuses may be implemented by any conventional or other fuses or limiting devices configured for any desired current level, while the power switch may be implemented by any conventional or other switching devices (e.g., momentary, button, etc.) The system may include any quantity of controllers, each controlling any quantity of drawers and accommodating any quantity of set points. The controllers may each be implemented by any conventional or other microprocessor or controller. Software for the controller may be implemented in any desired computer language and could be developed by one of ordinary skill in the computer arts based on the functional descriptions contained herein. The controller may alternatively be implemented by any type of hardware, software and/or other processing circuitry, and may be available pre-programmed for immediate use. The various functions of the controller may be distributed in any manner among any quantity of software modules, processors and/or circuitry. The algorithms and/or processes described above may be modified in any manner that accomplishes the functions described herein.

An intravenous pole and/or other equipment may be disposed at any locations on the temperature control system. The pole and/or equipment may include any quantity of temperature control systems attached to the pole and/or equipment.

The temperature sensing strip may be implemented by any conventional or other types of temperature strips. The temperature sensing strip may be of any shape or size, may sense and/or display any desired temperatures in any temperature scale (e.g., Fahrenheit, Celsius, etc.), and may include any type of indicators (e.g., alphanumeric or other characters) arranged in any fashion and representing any temperature intervals or other information for any desired temperature range. The temperature strip may utilize any color scheme to illuminate the indicators or to indicate whether or not the solution temperature is within particular ranges (e.g., above, within, or below a particular temperature range). Any quantity of temperature strips may be disposed on, attached to or formed integral with the system at any location having sufficient proximity to the item being measured via any conventional or other fastening techniques. The system may be implemented with or without the temperature sensing strips and/or labels.

The temperature sensing device may alternatively be implemented by any type of temperature measuring device (e.g., preferably those capable of measuring temperature without directly contacting container contents) and/or display. For example, the temperature sensing device may be implemented by a temperature sensor in combination with a liquid crystal (LCD) or other display to measure and display item temperature. This mechanism may include a battery and operate on direct current (DC) voltage, and/or include a power cord for connection to a common wall outlet jack and utilize alternating current (AC). Further, the temperature sensing device may be implemented by a temperature sensor and a voice or speech synthesizer to indicate temperature or to specify that an item is below or exceeds a predetermined temperature (e.g., provide an audio indication, such as "too hot", "too cold", etc.). Moreover, the temperature sensing device may employ an analog or infrared temperature sensor, or devices measuring temperature via sound, ultra-sonic or other waves, and convey that temperature in any of the manners described above.

The timer switch of system 700 may be implemented by any quantity of any type of pressure or other switch and/or switch/sensor combination for detecting the presence of a medical solution container or other item and actuating or disabling a circuit. The timer switch may include any types of mechanical, electrical and/or chemical switching mechanisms or any combinations thereof. The timer switch may be positioned at any location within the system or sub-compartment to detect the presence of a medical solution container or other item.

System 700 may be used at any suitable locations (e.g., hospital or other medical facility, emergency medical or other vehicles, etc.) with any types of power sources (e.g., AC, DC, wall outlet jack, batteries, vehicle power system, etc.) to heat any quantity of any type of medical solution container or other item. The system may be mounted on or supported by any type of support structure (e.g., wall, cart, table, floor, stand, etc.) via any conventional or other fastening mechanisms (e.g., brackets, hooks, welded, integral with system, etc.).

The timer of system 700 may be implemented by any conventional or other timing or timer devices (e.g., processors, hardware or other circuitry and/or software, etc.). The timer may be disposed at any suitable locations on or in proximity to the system. The timer may include any type of conventional or other display (e.g., LED, LCD, monitor, etc.) integral with or remote from the timer or system.

The timer of system 700 may be initiated by the timer switch and/or manually by a user via control or input devices (e.g., keys, buttons, etc.). The timer may increment or decrement time to measure elapsed time and may measure and/or display the time in any desired format or time units (e.g., hours, minutes, seconds, etc.). The timer or system may further include visual or audio alarms to notify a user when a particular time interval expired, or disable heating upon expiration of that time interval. Further, the timer may be combined with or implemented by the system controller. The timer reset line may perform a reset based on any type of signal (e.g., high or low). The reset typically causes the display to display an initial value, preferably zero, however the initial value may be set to any desired time or value. The system may include any quantity of timers, where the timers may each be associated with any quantity of sub-compartments and/or measure and/or display various time intervals (e.g., timer to measure residence time within the system or drawer, timer to measure residence time within a sub-compartment, etc.).

The reset relay may be implemented by any conventional or other relays or circuitry. The reset relay may provide any signal to the timer to facilitate a reset. The power source may be implemented by any conventional or other power source or circuitry and may provide any desired power signal (e.g., 12V DC, AC, voltage, current, etc.).

System 700 may store residence time or any other information (e.g., temperature, etc.) in memory in order to recover and maintain residence time measurements and/or heating in the event of a power failure or other interruption of power (e.g., power off, etc.). The system may further detect the temperature of a newly placed item prior to commencing heating. If the item has a temperature above a threshold indicating the item has been previously warmed, heating may be disabled and/or a user may be notified of the prior warming and/or that the residence time does not include the prior warming.

The sub-compartments and timers may include any identifiers (e.g., symbols, characters, numbers, etc.) to associate a sub-compartment with a corresponding timer. The sub-compartments and/or drawers may be individually controlled to heat corresponding medical items to the same or different desired temperatures.

The housings and housing components of systems 800, 900 (e.g., panels, walls, etc.) may be of any size, shape or configuration and may be constructed of any suitable materials including, but not limited to, electrogalvanized steel. The housing components may be connected via any conventional fastening techniques (e.g., welding, nuts and bolts, etc.). Any portion of the housings may be constructed of a transparent material. The heating, storage and housing compartments may be of any quantity, shape or size and may hold any quantity of medical solution containers or other items (e.g., one or more containers or items). The doors may be of any quantity, shape or size, may be constructed of any suitable materials, and may be connected to the housings at any suitable locations in any fashion to pivot in any desired direction and/or manner (e.g. hinged doors, sliding doors, removable panel doors, etc.). The top wall or doors may be connected to the housing at any suitable locations in any fashion to pivot in any desired direction and/or manner (e.g. hinged doors, sliding doors, removable panel doors, etc.). Further, the doors and top wall may include a window of any size or shape, while the doors, top wall and/or window may be constructed of any translucent, transparent or other materials. The doors and top wall may include any quantity of any type of handle or latching mechanism disposed at any suitable locations. The housing open portions may be of any shape or size and may be disposed at any suitable locations. The housings may include any types of openings, mechanisms, devices or other techniques to provide access to the housing interior.

Systems 800, 900 may warm any quantity of any type of medical solution container or other item to any desired temperature. The controllers of these systems may be implemented by any conventional or other microprocessor or controller. Software for the controllers may be implemented in any desired computer language and could be developed by one of ordinary skill in the computer arts based on the functional descriptions contained herein. The controllers may alternatively be implemented by any type of hardware, software and/or other processing circuitry, and may be available pre-programmed for immediate use. The various functions of the controllers may be distributed in any manner among any quantity of software modules, processors and/or circuitry. The algorithms and/or processes described above may be modified in any manner that accomplishes the functions described herein.

The controllers may be disposed on or within the systems at any suitable locations. The controllers may control the heater to any desired temperature. The controllers or systems may include any quantity of any type of input device (e.g., keys, buttons, mouse, voice, touch screen, etc.) to facilitate entry of any desired temperatures or any other information. The controllers may include or control any quantity of any type of display of any shape or size to convey any desired information. The display may be integral with or detached from the controllers or systems and may include an LED, LCD or monitor type display, indicator lights, or any other mechanism for indicating desired and/or measured temperature or any other information. Further, the display may include any type of buttons or data entry devices to program the controller in any manner. The controllers may employ any conventional or other control algorithms (e.g., fuzzy logic, PID, etc.). The systems may include any quantity of controllers to accommodate any quantity of heating assemblies, or a single controller may accommodate plural heating assemblies.

The heating plate may be of any quantity, shape, size or configuration to heat a medical solution or other item. The heating plate may include any quantity of conducting and/or non-conducting walls of any shape or size and may be constructed of any suitable materials. The heater of systems 800, 900 may be implemented by any quantity of any conventional heater or other heating device (e.g., conduction, convection, microwave or other radiation, etc.). The heating plate may include any quantity of heaters of any shape or size arranged in any configuration (e.g., strips, annular, segments, etc.) and disposed at any suitable locations for applying heat. The heater may be attached to the heating plate via any conventional or other fastening technique (e.g., pressure sensitive or other adhesives, etc.). The systems may alternatively include any quantity of heaters of any shape or size disposed at any suitable locations on the heating plate or within the systems.

The temperature sensors of systems 800, 900 may be implemented by any quantity of any type of conventional or other temperature measuring device (e.g., RTD, infrared, etc.) and may be disposed at any suitable locations on the arm, heating plate or within the systems. The cut-out switch may be implemented by any quantity of any type of conventional or other limiting device and may be utilized for any desired temperature or threshold. The cut-out switch may be utilized in combination with the additional temperature sensor to facilitate disablement of the heater in response to any desired temperature or temperature range. The cut-out switch and/or additional sensor may be disposed at any locations on the arm, heating plate or within the systems and may measure the temperature of any system objects (e.g., heating plate, medical item, heater, etc.). Alternatively, a single temperature sensor may be employed to facilitate control of the heater in response to measured medical item and excessive heater temperatures.

The limit switch of systems 800, 900 may be implemented by any quantity of any type of pressure or other switch and/or switch/sensor combination for detecting the presence of a medical solution container or other item and actuating or disabling a circuit. The limit switch may include any types of mechanical, electrical and/or chemical switching mechanisms or any combinations thereof. The limit switch may be positioned at any location proximate the heating plate or within the systems to detect the presence of a medical solution container or other item. The limit switch components (e.g., housing, arm, support member, contact member, etc.) may be of any shape or size and may be constructed of any suitable materials. The arm may support any quantity of any types of sensing devices. The switching circuitry may include any conventional or other circuitry or mechanical and/or electrical components that accommodate the contact member to establish or remove a circuit connection (e.g., open or close a circuit).

The control circuits of systems 800, 900 may utilize any conventional or other connectors or wiring to transfer power and other signals to system components. Further, the components of the control circuits (e.g., power switch, relay, fuses, controllers, boards, power sources, back light, connection terminal, etc.) may be implemented by any quantity of any conventional or other electrical components arranged in any fashion and performing the functions described above. The circuits may be disposed at any location on or within the housings and may be arranged in any fashion. The fuses may be implemented by any conventional or other fuses or limiting devices configured for any desired current level. The power switch, controllers, displays, input devices and indicators may be disposed at any suitable locations on or within the housings.

Systems 800, 900 may be used at any suitable locations (e.g., hospital or other medical facility, emergency medical or other vehicles, etc.) with any types of power sources (e.g., AC, DC, wall outlet jack, batteries, vehicle power system, etc.) to heat any quantity of any type of medical solution container or other item. The systems preferably heat items to desired temperatures within the approximate range of 80° F. -150° F., but may be utilized to heat the items to any desired temperatures or temperature ranges.

Systems 800, 900 may be mounted on or supported by any type of support structure (e.g., wall, cart, table, floor, stand, etc.). The stand may be of any type, shape or size, may be constructed of any suitable materials and may be utilized with any of the above-described systems. The stand may be connected to the systems at any desired locations via any conventional or other fastening mechanisms (e.g., brackets, hooks, welded, integral with system, etc.). The stand components (e.g., hub, post, legs, etc.) may be of any quantity, shape or size, may be constructed of any suitable materials and may be arranged in any desired fashion. The stand may include any quantity of any type of wheels or rollers disposed at any suitable locations to facilitate transport of the system.

The storage compartment and door window may be of any shape or size and may be disposed at any suitable locations. The window may be constructed of any suitable materials (e.g., glass, plastic, etc.) and include any desired degree of transparency.

The timer of systems 800, 900 may be implemented by any conventional or other timing or timer devices (e.g., processors, hardware or other circuitry and/or software, etc.). The timer may be utilized with any of the above-described systems and may be disposed at any suitable locations on or in proximity to the systems. The timer may include any type of conventional or other display (e.g., LED, LCD, etc.) integral with or remote from the timer or systems. The timer or heat controller may be initiated by the limit switch and/or manually by a user via control or input devices (e.g., keys, buttons, etc.) to initiate time measurement. The timer or heat controller may increment or decrement time to measure elapsed time and may measure and/or display the time in any desired format or time units (e.g., hours, minutes, seconds, etc.). The systems may further include visual or audio alarms to notify a user when a particular time interval expired, or disable heating upon expiration of that time interval. Further, a timer may be combined with or implemented by any of the above-described controllers. The timer reset line may perform a reset based on any type of signal (e.g., high or low). A time reset typically causes the timer or other display to display an initial value, preferably zero, however the initial value may be set to any desired time or value. Further, a time reset may facilitate display of any type of indicator (e.g., reload or empty indication, etc.) The systems may include any quantity of timers or controllers to measure and/or display various time intervals (e.g., timer to measure residence time within the system or storage compartment, timer to measure residence time on heating plate, etc.).

The various relays (e.g., time delay, reset, etc.) may be implemented by any conventional or other relays or circuitry. The reset relay may provide any signal to the timer to facilitate a reset. The time delay reset or heat controller may be set to provide any desired time delay in any desired time units (e.g., minutes, seconds, etc.). The power sources may be implemented by any conventional or other power sources or circuitry and may provide any desired power signal (e.g., 12V DC, AC, voltage, current, etc.).

The guides may be of any quantity, shape or size, and may be constructed of any suitable materials (e.g., foam, plastic, etc.). The guides may be disposed in the system in any quantity and in any desired fashion. The guide components (e.g., leg, foot, etc.) may be of any shape or size and may be connected in any fashion (e.g., at any desired angle, etc.). The guides may be configured in any fashion (e.g., without legs) for use with the systems described above (e.g., with or without a storage compartment) to align the medical item.

The trays may be of any quantity, shape or size, and may be constructed of any suitable materials. The trays may be oriented at any desired angle and may be mounted within the system housing in any desired fashion via any conventional or other mounting mechanisms (e.g., rails, brackets, ledges, etc.). System 900 may include any quantity of trays, with each tray including any quantity of heating assemblies. The trays may include any quantity of dividers, where the dividers may be of any shape or size. The heating assemblies may be placed adjacent each other on a tray without dividers. Alternatively, any quantity of heating plates may be formed within a continuous sheet of heat conducting material.

The system controller may directly control any quantity of heating assemblies without use of the heat controllers. The system controller may further communicate in any fashion with the heat controllers via any suitable protocols. The system controller may receive any desired information from a user, transfer any desired information to the heat controllers and may utilize any quantity of any type of indicators (e.g., visual, audio, LEDs, display, etc.) to indicate system conditions (e.g., power on, attainment of set point temperature, etc.). The display may display any information arranged in any fashion. The heating assemblies may include any identifiers (e.g., symbols, characters, numbers, etc.) to associate a heating assembly with displayed information.

The heat controllers may control any quantity of heating assemblies and may transfer and receive any desired information from the system controller. The heat controllers may store residence time or any other information (e.g., temperature, etc.) in memory in order to recover and maintain residence time measurements and/or heating in the event of a power failure or other interruption of power (e.g., power off, etc.). The heat controllers may further detect the temperature of a newly placed item prior to commencing heating. If the item has a temperature above a threshold indicating the item has been previously warmed, heating may be disabled and/or a user may be notified of the prior warming and/or that the residence time does not include the prior warming. The heat controllers may detect any conditions and provide the information to the system controller. The heat controller may illuminate the assembly indicator when the item temperature is within any desired range of the set point temperature. The assembly indicator may be disposed at any location on the heating assembly, housing or tray and may be implemented by any visual (LED, etc.) or audio device. The heat controllers may communicate with the system controller synchronously or asynchronously and at any desired time or time intervals. The functions of the system and heat controllers may be distributed in any fashion among those controllers (e.g., the system may operate without one of those controllers). The heating assemblies may be individually controlled to heat corresponding medical items to the same or different desired temperatures.

Systems 800, 900 and/or the limit switch may be responsive to a particular weight of or pressure exerted by a medical item (e.g., to initiate heating, residence time measurements, etc.). For example, the limit switch may enter a closed state in response to a medical item having at least a desired weight or exerting at least a certain pressure against the switch. This enables the system to accommodate and discriminate between particular medical items (e.g., a system for heating three liter medical solution bags does not operate for one liter medical solution bags).

The marking device may be powered by any conventional or other power source (e.g., AC, DC, wall outlet jack, batteries, etc.). The marking device may be of any quantity, may be implemented by any conventional or other marking device and may be utilized in combination with any quantity of thermal treatment or other systems. The marking device may be implemented as a stand-alone device or may be attached to or integral with the thermal treatment or other system. The marking device is preferably disposed within the proximity of the thermal treatment or other system, but may be disposed in any fashion relative to that system.

The marking device housing may be of any shape or size and may be constructed of any suitable materials. The marking device may be securable (either alone or in combination with the thermal treatment or other system) to any type of support structure (e.g., wall, pole, stand, etc.) via any conventional or other securing techniques (e.g., brackets, etc.). The marking device components (e.g., processor, switch, display, input devices, printing unit, etc.) may be disposed and arranged on and/or in the housing in any desired fashion. The marking area may be disposed at any location on the housing and may be of any shape or size to accommodate marking of any desired items.

The marking device switch may be disposed in the marking area or at any other locations suitable to engage the item and initiate marking. The marking device processor may be implemented by any quantity of any conventional or other microprocessor or controller (e.g., chip, card, processor, circuitry, etc.). The marking device may include any quantity of any desired input devices (e.g., buttons, keypad, voice recognition, touch screen, etc.) disposed at any locations. The marking device may employ any type of conventional or other sensor or switch to indicate the presence of an item for marking. Alternatively, the marking device may include a marking key or button for manual control of marking by a user (e.g., the key is actuated by a user in response to proper positioning of the item for marking).

The marking device may mark any types of medical or other items (e.g., solution containers or bags, cassettes, lines, labels, instruments, fabrics, cards, materials, paper products, etc.) at any locations on the items. The items may be transported or presented to the marking device by a user for marking. Alternatively, the marking device may store items therein and provide to a user an item with time stamp information. For example, the marking device may store blank labels or labels pre-printed with descriptive information. When a user actuates a marking device key or button, the marking device retrieves a stored label and places the time stamp information thereon. The label with time stamp information is provided to the user for attachment to a medical item.

The marking device may maintain and/or provide any desired information for placement on an item (e.g., start date and time of solution or other item heating/cooling, the time interval the solution or other item was heated/cooled, the temperature the solution or other item attained during heating/cooling, temperature of the solution or other item when the solution was removed from the system, amount or quantity of solution or other item residing, placed in or removed from the system, partial or complete history of time and solution or other item temperature measured at any desired time intervals, facility information, patient information, doctor information, type of procedure, solution information, type of instruments or other item being heated/cooled, amount or quantity of solution or other item being heated/cooled, etc.) from any desired sources (e.g., thermal treatment system, user, memory device, another computer or device, etc.). The processor may maintain the time stamp information internally or utilize any desired external circuitry (e.g., a timer, memory, etc.). The marking device may further maintain the time stamp information provided to articles to provide a report of medical item or procedure activity for any desired time interval.

The time stamp information may be arranged in any fashion and include any desired information. The date, time and other information may be in any desired format (e.g., month, day and year, hours and minutes, text, numeric, icons, etc.). The time stamp information may be arranged and/or presented (e.g., printed, displayed, etc.) in any desired formats and in any order or arrangement. The time stamp information may alternatively be stored in a local or remote database or memory device (e.g., local memory, removable memory, etc.) for later retrieval. The printed or marked time stamp information may include a pre-arranged format or may be programmable or selected by a user via marking device input devices. The time stamp information may be placed at any suitable location on an item. The marking device display may be of any quantity, shape or size, may be disposed at any location on or remote from the marking device, may be implemented by any conventional or other displays (e.g., LED, LCD, etc.) and may display any desired information. The information displayed may be selected via marking device input devices, or the display may include display controls (e.g., buttons, keys, etc.).

The marking device printing unit may be implemented by any conventional or other printing or impression device and may transfer the time stamp information on any desired medium (e.g., paper, labels, medical items, etc.). The time stamp information may be placed directly on the article (e.g., item or label) via any conventional or other techniques (e.g., a physical impression on the article (with or without ink), a printed indicator by dot matrix, laser printing or thermal techniques, etc.). The marking device and thermal treatment system may include any conventional or other communications device or module (e.g., modem, etc.) to communicate with each other or other devices. For example, placement of time stamp information on a medical item may enable the marking device to communicate with the thermal treatment system to start and/or cease operation. Further, the marking device may download or transfer an electronic form of the time stamp information to any desired device (e.g., PDA, computer, another marking device, thermal treatment system, etc.) at any specific time or in response to user entered information (e.g., transmit command or key). The marking device may further be networked to enable retrieval of information from a station or other devices (e.g., thermal treatment system, another marking device, etc.) coupled to the network. Any desired information may be transmitted between the marking device components (e.g., processor, switch, display, input devices, printing unit, etc.) via any conventional or other communications medium or protocols (e.g., hardwire, wireless, network, etc.).

The label for the time stamp information may be of any size or shape and may be of any type of printing material (e.g., paper, thermal paper, fabric, etc.). The label may include any quantity of areas or fields at any suitable locations to receive specific time stamp information from the marking device (e.g., entry time into the thermal treatment system, removal time, date, facility name, type of solution, etc.). The fields may include any type of descriptive information. Alternatively, the labels may be blank, where the marking device provides the time stamp and descriptive information. The descriptive information may be provided pre-printed on the label or by the marking device in any combination.

The labels may be adhered to the medical item at any suitable locations via any conventional or other techniques (e.g., adhesive, fastener, self-adhesive label, etc.). The label adhesive may be sufficiently strong to prevent removal of the label from the bag and/or label tampering, or the strength of the label adhesive may enable a user to remove the label from the bag for attachment to other items (e.g., patient or other chart or record, etc.). Alternatively, the medical item may include the label already attached and be presented to the marking device to receive the time stamp information. In addition, the medical item may include any descriptive information and/or fields and may directly receive the time stamp information from the marking device (e.g., via printing or impression techniques) at any desired locations.

The label may be any type of label enabling any quantity of time stamp information to be placed thereon. Further, the label may include or be partitioned into any quantity of individual sections, each of which may receive time stamp information at different instances and may be individually adhesive. For example, a label may include or be partitioned into two sections. The label is presented to or supplied by the marking device, where a first section receives time stamp information pertaining to insertion of a medical item into a thermal treatment system. The label is adhered to a medical item (e.g., with the first section adhering to the medical item and the second section in a non-adhering state) prior to insertion of the medical item into the thermal treatment system. When the medical item is removed from the thermal treatment system, the medical item is transported to the marking device to enable the second section of the label (e.g., which is not adhered to the medical item) to be presented to the marking device to receive time stamp information pertaining to removal of the medical item from the thermal treatment system. The second label section is subsequently placed in an adhering state for adherence to the medical item.

Software for the marking device processor may be implemented in any desired computer language and could be developed by one of ordinary skill in the computer arts based on the functional descriptions contained herein. The processor may alternatively be implemented by any type of hardware and/or other processing circuitry, and may be available pre-programmed for immediate use. The various functions of the processor may be distributed in any manner among any quantity of software modules, processors and/or circuitry. The algorithms and/or processes described above may be modified in any manner that accomplishes the functions described herein. Further, an item may be marked any quantity of times with time stamp information at any instances to provide a history of item activity and may include any quantity of labels. Moreover, an item may include time stamp information placed directly on the item, placed on a label adhered to the item, or placed on the item and label in any combination.

The thermal treatment systems described above may be used at any suitable locations (e.g., hospital or other medical facility, emergency medical or other vehicles, etc.) with any types of power sources (e.g., AC, DC, wall outlet jack, batteries, vehicle power system, etc.) to thermally treat any quantity of any type of medical solution container or other item. The systems preferably heat items to desired temperatures within the approximate range of 80° F.-150° F., but may be utilized to heat and/or cool the items to any desired temperatures or temperature ranges.

It is to be understood that the terms "top", "bottom", "front", "rear", "side", "height", "width", "length", "upper", "lower" and the like are used herein merely to describe points of reference and do not limit the present invention to any particular configuration or orientation.

From the foregoing description, it will be appreciated that the invention makes available novel medical item thermal treatment systems and method of monitoring medical items for compliance with prescribed requirements, wherein medical items may be monitored for compliance with prescribed requirements from item manufacture through item use and/or disposal.

Having described preferred embodiments of new and improved medical item thermal treatment systems and method of monitoring medical items for compliance with prescribed requirements, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A temperature control system for thermally treating medical items to desired temperatures comprising:
   a temperature control unit including:
      a unit housing;
      a thermal treatment unit disposed within said housing to thermally treat at least one medical item;
      a controller to facilitate entry of a desired temperature and to control a thermal output of said thermal treatment unit to thermally treat said at least one medical item to said entered desired temperature; and
      a usage control unit to confine operational usage of said temperature control unit by a user for thermally treating said at least one medical item to be within an authorized use interval for said user defined by usage parameters associated with said user, wherein said usage control unit disables operation of said temperature control unit by said user for thermally treating said at least one medical item outside said authorized use interval associated with said user and said usage parameters include at least one of a time interval for said operational usage of said temperature control unit to thermally treat said at least one medical item, a quantity of thermal cycles, a quantity of medical items to thermally treat, and a duration a medical item remains within said system.

2. The temperature control system of claim 1, wherein said thermal treatment unit heats said at least one medical item.

3. The temperature control system of claim 1, wherein said thermal treatment unit cools said at least one medical item.

4. The temperature control system of claim 1, wherein said temperature control unit further includes:
at least one temperature sensor to measure a temperature of a corresponding medical item, wherein said controller controls said thermal output of said thermal treatment unit to thermally treat said at least one medical item to said entered desired temperature based on said temperature measured by said corresponding temperature sensor.

5. The temperature control system of claim 4, wherein said temperature control unit further includes:
a timer to measure residence time of each medical item thermally treated by said thermal treatment unit.

6. The temperature control system of claim 1 further including:
an information storage device to store said usage parameters, wherein said information storage device is provided by said user to said temperature control unit.

7. The temperature control system of claim 6, wherein said information storage device includes at least one of a card, a memory device, a removable storage device, an integrated circuit and a chip.

8. The temperature control system of claim 6, wherein said usage control unit includes:
a system interface to transfer information with said information storage device.

9. The temperature control system of claim 8, wherein said system interface collects information pertaining to at least one of medical item conditions, system conditions, time, corresponding temperature information for at least one medical item, patient information, user information, doctor information and facility information.

10. The temperature control system of claim 9, wherein said system interface stores said collected information on said information storage device.

11. The temperature control system of claim 10, wherein said information storage device is provided to a service provider to retrieve said stored information from said information storage device and generate a report for said user.

12. The temperature control system of claim 10 further including:
an external interface to transfer information with said information storage device; and
an external processing device coupled to said external interface to enable transfer of information with said information storage device.

13. The temperature control system of claim 12, wherein said external processing device enables an authorized user to perform at least one of retrieval of information from said information storage device in the form of a report and adjust said usage parameters stored on said information storage device to enable further use of said temperature control unit.

14. The temperature control system of claim 12 further including:
a server system in communication with said external processing device to receive and store said information stored on said information storage device, wherein said server system includes a web site accessible by said user to perform at least one of retrieval of information from said information storage device in the form of a report and adjust said usage parameters stored on said information storage device to enable further use of said temperature control unit.

15. The temperature control system of claim 1, wherein said temperature control unit further includes:
a communications device to facilitate communications with an external device and to collect information pertaining to at least one of medical item conditions, system conditions, time, corresponding temperature information for at least one medical item, patient information, user information, doctor information and facility information.

16. The temperature control system of claim 15, wherein said external device includes a server system to transfer information with said communications device and to store said collected information.

17. The temperature control system of claim 16, wherein said server system communicates with said communication device via a network.

18. The temperature control system of claim 16, wherein said server system includes a web site accessible by said user via an end user device to perform at least one of retrieval of said collected information in the form of a report and adjustment of said usage parameters to enable further use of said temperature control system.

19. The temperature control system of claim 16, wherein said communications device transfers said collected information to said server system in real time to enable said user to access said transferred information via an end user device to remotely monitor a status of said temperature control unit.

20. The temperature control system of claim 19, wherein said end user device provides at least one alarm to indicate conditions exceeding prescribed requirements.

21. The temperature control system of claim 19, further including a plurality of said temperature control units, wherein said communications device of each temperature control unit transfers said collected information to said server system in real time to enable said user to access said transferred information via an end user device to remotely monitor a status of said temperature control units.

22. A temperature control system for thermally treating medical items to desired temperatures comprising:
a temperature control unit including:
a unit housing;
a thermal treatment unit disposed within said housing to thermally treat at least one medical item;
a controller to facilitate entry of a desired temperature and to control a thermal output of said thermal treatment unit to thermally treat said at least one medical item to said entered desired temperature; and
a usage control unit to control usage of said temperature control unit in accordance with usage parameters associated with a user;
an information storage device to store said usage parameters, wherein said information storage device is provided by said user to said temperature control unit and said usage parameters stored on said information storage device are adjusted by a service provider to enable further use of said temperature control unit.

23. A temperature control system for thermally treating medical items to desired temperatures comprising:
a temperature control unit including:
a unit housing;
a thermal treatment unit disposed within said housing to thermally treat at least one medical item;

a controller to facilitate entry of a desired temperature and to control a thermal output of said thermal treatment unit to thermally treat said at least one medical item to said entered desired temperature; and a usage control unit to control usage of said temperature control unit in accordance with usage parameters associated with a user;

an information storage device to store said usage parameters, wherein said information storage device is provided by said user to said temperature control unit;

wherein said usage control unit includes a system interface to transfer information with said information storage device, and wherein said system interface disables said controller in response to said usage parameters indicating completion of authorized use of said temperature control unit.

24. A temperature control system for thermally treating medical items to desired temperatures comprising:

a temperature control unit including:
  a unit housing;
  a thermal treatment unit disposed within said housing to thermally treat at least one medical item;
  a controller to facilitate entry of a desired temperature and to control a thermal output of said thermal treatment unit to thermally treat said at least one medical item to said entered desired temperature; and
  a usage control unit to control usage of said temperature control unit in accordance with usage parameters associated with a user;

an information storage device to store said usage parameters, wherein said information storage device is provided by said user to said temperature control unit;

wherein said usage control unit includes a system interface to transfer information with said information storage device, and wherein said system interface updates said usage parameters in accordance with use of said temperature control unit by said user.

25. The temperature control system of claim 24, wherein said temperature control unit further includes:

a display to display at least one of said updated usage parameters to inform said user of remaining authorized use of said temperature control unit.

26. A system for confining operational use of a temperature control unit that thermally treats medical items to desired temperatures to be within an authorized use interval in accordance with usage parameters associated with a user and defining said authorized use interval, wherein operation of said temperature control unit by said user for thermally treating at least one medical item is disabled outside said authorized use interval associated with said user, said system comprising:

a server computer system including a web site accessible by said user to modify said authorized use interval by adjusting said usage parameters to enable further use of said temperature control unit by said user, and wherein said usage parameters include at least one of a time interval for said operational usage of said temperature control unit to thermally treat said at least one medical item, a quantity of thermal cycles, a quantity of medical items to thermally treat, and a duration a medical item remains within said temperature control unit.

27. The system of claim 26 further including:

an information storage device to transfer information with said temperature control unit and store collected information;

an external interface to transfer information with said information storage device; and an external processing device coupled to said external interface to enable transfer of information between said information storage device and said server computer system.

28. The system of claim 27, wherein said information storage device stores said usage parameters to control use of said temperature control unit.

29. A system for controlling use of a temperature control unit that thermally treats medical items to desired temperatures in accordance with usage parameters associated with a user, said system comprising:

a server computer system to receive and store information collected by said temperature control unit, wherein said server computer system includes a web site accessible by said user to perform at least one of retrieval of said collected information in the form of a report and adjustment of said usage parameters to enable further use of said temperature control unit, wherein said server computer system communicates with said temperature control unit to receive said collected information and adjust said usage parameters.

30. The system of claim 29, wherein said server computer system communicates with said temperature control unit via a network.

31. The system of claim 29, wherein said temperature control unit transfers said collected information to said server computer system in real time to enable said user to access said transferred information via an end user device to remotely monitor a status of said temperature control unit.

32. A method of thermally treating medical items to desired temperatures comprising:

(a) receiving at least one medical item within a housing of a temperature control unit for thermal treatment by a thermal treatment unit;

(b) facilitating entry of a desired temperature and controlling a thermal output of said thermal treatment unit to thermally treat said at least one medical item to said entered desired temperature; and (c) confining operational usage of said temperature control unit by a user for thermally treating said at least one medical item to be within an authorized use interval for said user defined by usage parameters associated with said user, wherein operation of said temperature control unit by said user for thermally treating said at least one medical item is disabled outside said authorized use interval associated with said user and said usage parameters include at least one of a time interval for said operational usage of said temperature control unit to thermally treat said at least one medical item, a quantity of thermal cycles, a quantity of medical items to thermally treat, and a duration a medical item remains within said system.

33. The method of claim 32, wherein step (a) further includes:

(a.1) heating said at least one medical item.

34. The method of claim 32, wherein step (a) further includes:

(a.1) cooling said at least one medical item.

35. The method of claim 32, wherein step (b) further includes:

(b.1) measuring a temperature of a corresponding medical item and controlling said thermal output of said thermal treatment unit to thermally treat said at least one medical item to said entered desired temperature based on a corresponding measured temperature.

36. The method of claim 35, wherein step (b) further includes:
   (b.2) measuring residence time of each medical item thermally treated by said thermal treatment unit.

37. The method of claim 32, wherein step (c) further includes:
   (c.1) storing said usage parameters on an information storage device, wherein said information storage device is provided by said user to said temperature control unit.

38. The method of claim 37, wherein said information storage device includes at least one of a card, a memory device, a removable storage device, an integrated circuit and a chip.

39. The method of claim 37, wherein step (b) further includes:
   (b.1) collecting information pertaining to at least one of medical item conditions, unit conditions, time, corresponding temperature information for at least one medical item, patient information, user information, doctor information and facility information.

40. The method of claim 39, wherein step (c) further includes:
   (c.2) storing said collected information on said information storage device.

41. The method of claim 40 further including:
   (d) providing said information storage device to a service provider to retrieve said stored information from said information storage device and generate a report for said user.

42. The method of claim 40 further including:
   (d) performing, via an external processing device, at least one of retrieval of information from said information storage device in the form of a report and adjustment of said usage parameters stored on said information storage device to enable further use of said temperature control unit.

43. The method of claim 40, wherein an external device transfers information with said information storage device and is coupled to a server system with a web site, and said method further includes:
   (d) transferring said collected information from said information storage device to said server system; and
   (e) performing, via said web site of said server system, at least one of retrieval of said collected information from said server system in the form of a report and adjustment of said usage parameters stored on said information storage device to enable further use of said temperature control unit.

44. The method of claim 32, wherein step (b) further includes:
   (b.1) collecting information pertaining to at least one of medical item conditions, unit conditions, time, corresponding temperature information for at least one medical item, patient information, user information, doctor information and facility information; and
   (b.2) storing said collected information on a server system in communication with said temperature control unit.

45. The method of claim 44, wherein said server system communicates with said temperature control unit via a network.

46. The method of claim 44, wherein said server system includes a web site accessible by said user via an end user device, and said method further includes:
   (d) performing, via said web site of said server system, at least one of retrieval of said collected information in the form of a report and adjustment of said usage parameters to enable further use of said temperature control system.

47. The method of claim 44, wherein step (b.1) further includes:
   (b.1.1) transferring said collected information to said server system in real time; and
   said method further includes:
   (d) accessing said transferred information via an end user device to remotely monitor a status of said temperature control unit.

48. The method of claim 47, wherein step (d) further includes:
   (d.1) providing at least one alarm on said end user device to indicate conditions exceeding prescribed requirements.

49. A method of thermally treating medical items to desired temperatures comprising:
   (a) receiving at least one medical item within a housing of a temperature control unit for thermal treatment by a thermal treatment unit;
   (b) facilitating entry of a desired temperature and controlling a thermal output of said thermal treatment unit to thermally treat said at least one medical item to said entered desired temperature; and
   (c) controlling usage of said temperature control unit in accordance with usage parameters associated with a user, wherein step (c) further includes:
      (c.1) storing said usage parameters on an information storage device, wherein said information storage device is provided by said user to said temperature control unit; and
      (c.2) adjusting said usage parameters by a service provider to enable further use of said temperature control unit.

50. A method of thermally treating medical items to desired temperatures comprising:
   (a) receiving at least one medical item within a housing of a temperature control unit for thermal treatment by a thermal treatment unit;
   (b) facilitating entry of a desired temperature and controlling a thermal output of said thermal treatment unit to thermally treat said at least one medical item to said entered desired temperature; and
   (c) controlling usage of said temperature control unit in accordance with usage parameters associated with a user, wherein step (c) further includes:
      (c.1) storing said usage parameters on an information storage device, wherein said information storage device is provided by said user to said temperature control unit; and
      (c.2) transferring information with said information storage device and disabling said temperature control unit in response to said usage parameters indicating completion of authorized use of said temperature control unit.

51. A method of thermally treating medical items to desired temperatures comprising:
   (a) receiving at least one medical item within a housing of a temperature control unit for thermal treatment by a thermal treatment unit;
   (b) facilitating entry of a desired temperature and controlling a thermal output of said thermal treatment unit to thermally treat said at least one medical item to said entered desired temperature; and (c) controlling usage of said temperature control unit in accordance with usage parameters associated with a user, wherein step (c) further includes:
(c.1) storing said usage parameters on an information storage device, wherein said information storage device is provided by said user to said temperature control unit; and
(c.2) updating said usage parameters in accordance with use of said temperature control unit by said user.

52. The method of claim 51, wherein step (c) further includes:
(c.3) displaying at least one of said updated usage parameters to inform said user of remaining authorized use of said temperature control unit.

53. A method of confining operational use of a temperature control unit that thermally treats medical items to desired temperatures to be within an authorized use interval in accordance with usage parameters associated with a user and defining said authorized use interval, wherein operation of said temperature control unit by said user for thermally treating at least one medical item is disabled outside said authorized use interval associated with said user, said method comprising:
(a) receiving and storing information collected by said temperature control unit on a server computer system including a web site accessible by said user; and
(b) modifying said authorized use interval by adjusting said usage parameters, via said web site, to enable further use of said temperature control unit by said user, wherein said usage parameters include at least one of a time interval for said operational usage of said temperature control unit to thermally treat said at least one medical item, a quantity of thermal cycles, a quantity of medical items to thermally treat, and a duration a medical item remains within said temperature control unit.

54. The method of claim 53, wherein step (a) further includes:
(a.1) storing said collected information on an information storage device;
(a.2) transferring information between said information storage device and said temperature control unit; and
(a.3) transferring information between said information storage device and said server computer system.

55. The method of claim 54, wherein step (a.1) further includes:
(a.1.1) storing said usage parameters on said information storage device to control use of said temperature control unit.

56. A method of controlling use of a temperature control unit that thermally treats medical items to desired temperatures in accordance with usage parameters associated with a user, said method comprising:
(a) receiving and storing information collected by said temperature control unit on a server computer system including a web site accessible by said user, wherein said server computer system conununicates with said temperature control unit, and step (a) further includes:
(a.1) receiving said collected information from said temperature control unit and adjusting said usage parameters via said server computer system;
(b) performing, via said web site, at least one of retrieval of said collected information in the form of a report and adjustment of said usage parameters to enable further use of said temperature control unit.

57. The method of claim 56, wherein said server computer system communicates with said temperature control unit via a network.

58. The method of claim 56, wherein step (a.1) further includes:
(a.1.1) transferring said collected information from said temperature control unit to said server computer system in real time; and
said method further includes:
(c) accessing said transferred information via an end user device to remotely monitor a status of said temperature control unit.

59. A system for controlling usage of a medical device comprising:
a medical device; and
a usage control unit to confine operational usage of said medical device by a user to be within an authorized use interval for said user defined by usage parameters associated with said user, wherein said usage control unit disables operation of said medical device by said user outside said authorized use interval associated with said user and said usage parameters include at least one of a time interval for said operational usage of said medical device and a quantity of operational cycles.

60. The system of claim 59, wherein said medical device collects information pertaining to at least one of system conditions, time, patient information, user information, doctor information and facility information.

61. The system of claim 60 further including:
an information storage device to store at least one of said usage parameters and said collected information, wherein said information storage device is provided by said user to said medical device.

62. The system of claim 61, wherein said information storage device includes at least one of a card, a memory device, a removable storage device, an integrated circuit and a chip.

63. The system of claim 61, wherein said information storage device is provided to a service provider to retrieve said stored information from said information storage device and generate a report for said user.

64. The system of claim 60 further including:
a server computer system to receive and store said collected information, wherein said server computer system includes a web site accessible by said user to perform at least one of retrieval of said collected information in the form of a report and adjustment of said usage parameters to enable further use of said medical device.

65. A method of controlling use of a medical device comprising:
(a) confining operational usage of said medical device by a user to be within an authorized use interval for said user defined by usage parameters associated with said user, wherein operation of said medical device by said user is disabled outside said authorized use interval associated with said user and said usage parameters include at least one of a time interval for said operational usage of said medical device and a quantity of operational cycles.

66. The method of claim 65, wherein step (a) further includes:
(a.1) collecting information, via said medical device, pertaining to at least one of system conditions, time, patient information, user information, doctor information and facility information.

67. The method of claim 66, wherein step (a) further includes:
  (a.2) storing at least one of said usage parameters and said collected information on an information storage device, wherein said information storage device is provided by said user to said medical device.

68. The method of claim 67, wherein said information storage device includes at least one of a card, a memory device, a removable storage device, an integrated circuit and a chip.

69. The method of claim 67, wherein step (a) further includes:
  (a.3) providing said information storage device to a service provider to retrieve said stored information from said information storage device and generate a report for said user.

70. The method of claim 66, wherein step (a) further includes:
  (a.2) receiving and storing said collected information on a server computer system, wherein said server computer system includes a web site accessible by said user; and
  (a.3) performing, via said web site, at least one of retrieval of said collected information in the form of a report and adjustment of said usage parameters to enable further use of said medical device.

71. The method of claim 65, wherein step (a) further includes:
  (a.1) leasing said medical device to said user, wherein said usage parameters include values to control use of said medical device in accordance with an associated leasing arrangement.

72. The method of claim 65, wherein step (a) further includes:
  (a.1) renting said medical device to said user, wherein said usage parameters include values to control use of said medical device in accordance with an associated rental arrangement.

* * * * *